(12) United States Patent
Koenemann et al.

(10) Patent No.: US 8,088,922 B2
(45) Date of Patent: Jan. 3, 2012

(54) DIBENZORYLENETETRACARBOXIMIDES AS INFRARED ABSORBERS

(75) Inventors: Martin Koenemann, Mannheim (DE); Arno Boehm, Mannheim (DE); Yuri Avlasevic, Mainz (DE); Klaus Muellen, Cologne (DE)

(73) Assignees: BASF Aktiengesellschaft, Ludwigshafen (DE); Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 323 days.

(21) Appl. No.: 12/302,836

(22) PCT Filed: May 29, 2007

(86) PCT No.: PCT/EP2007/055194
§ 371 (c)(1),
(2), (4) Date: Nov. 28, 2008

(87) PCT Pub. No.: WO2007/138051
PCT Pub. Date: Dec. 6, 2007

(65) Prior Publication Data
US 2010/0048904 A1 Feb. 25, 2010

(30) Foreign Application Priority Data
May 30, 2006 (EP) .................... 06114685

(51) Int. Cl.
*C07D 401/08* (2006.01)
*H01L 21/331* (2006.01)

(52) U.S. Cl. ............ 546/26; 438/483; 438/779; 546/31; 546/41; 546/81

(58) Field of Classification Search ............... 546/26, 546/31, 41, 81; 438/483, 779
See application file for complete search history.

(56) References Cited

U.S. PATENT DOCUMENTS
2009/0236591 A1 9/2009 Konemann et al.

FOREIGN PATENT DOCUMENTS
WO 2005 102672 11/2005

OTHER PUBLICATIONS

U.S. Appl. 12/738,947, filed Apr. 20, 2010, Koenemann, et al.
U.S. Appl. No. 12/673,908, filed Feb. 17, 2010, Koenemann, et al.
Desilets, D. et al., "Design and Synthesis of Near-Infrared Absorbing Pigments. I. Use of Pariser-Parr-Pople Molecular Orbital Calculations for the Identification of Near-Infrared Absorbing Pigment Candidates", Canadian Journal of Chemistry, vol. 73, No. 3, pp. 319-324 (1995) XP-002447201.
Adachi, M. et al., "Design of Near-Infrared Dyes Based on π-Conjugation System Extension 2. Theoretical Elucidation of Framework Extended Derivatives of Perylene Chromophore, Chemistry of Materials", vol. 13, No. 2, pp. 662-669 (2001) XP-002447202.
Mueller, S. et al., "Facile Synthetic Approach to Novel Core-Extended Perylene Carboximide Dyes", Chemical Communications, vol. 32, pp. 4045-4046 (2005) XP-002447203.
Desilets, D. et al., "Design and Synthesis of Near-Infrared Absorbing Pigments. II. Structure Determination of Acenanthrene Green and Derivatives", Canadian Journal of Chemistry, vol. 73, No. 3, pp. 325-335 (1995) XP-002447204.
Avlasevich, Y. et al., "Dibenzopentarylenebis (dicarboximide)s: Novel Near-Infrared Absorbing Dyes", Chemical Communications, vol. 42, pp. 4440-4442 (2006) XP-002447205.
U.S. Appl. No. 12/666,127, filed Dec. 22, 2009, Koenemann, et al.

*Primary Examiner* — Charanjit Aulakh
(74) *Attorney, Agent, or Firm* — Oblon, Spivak, McClelland, Maier & Neustadt, L.L.P.

(57) ABSTRACT

Dibenzorylenetetracarboximides of the general formula I

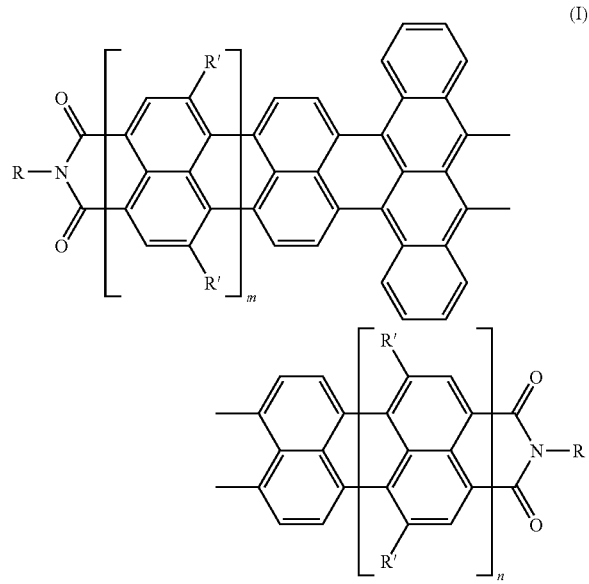

in which the variables are each defined as follows:
R' are identical or different radicals:
  hydrogen; optionally substituted aryloxy, arylthio, hetaryloxy or hetarylthio;
R are identical or different radicals:
  hydrogen; optionally substituted $C_1$-$C_{30}$-alkyl, $C_3$-$C_8$-cycloalkyl, aryl or hetaryl;
m, n are each independently 0 or 1.

19 Claims, 1 Drawing Sheet

DIBENZORYLENETETRACARBOXIMIDES AS INFRARED ABSORBERS

The present invention relates to novel dibenzorylenetetracarboximides of the general formula I

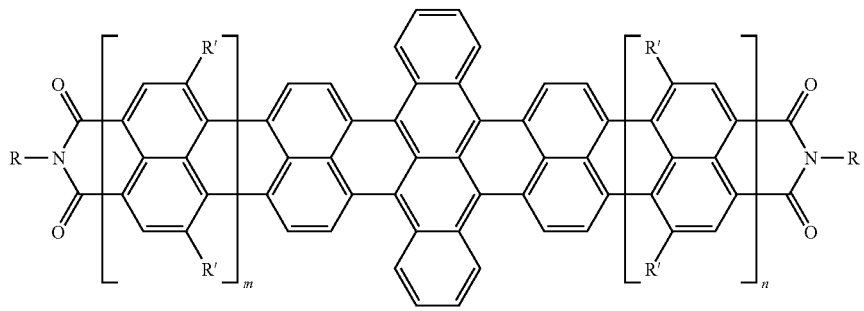

in which the variables are each defined as follows:

R' are identical or different radicals:
hydrogen;
aryloxy, arylthio, hetaryloxy or hetarylthio, to each of which may be fused further saturated or unsaturated 5- to 7-membered rings whose carbon skeleton may be interrupted by one or more —O—, —S—, —NR$^1$—, —N=CR$^1$—, —CO—, —SO— and/or —SO$_2$— moieties, where the entire ring system may be mono- or polysubstituted by the radicals (i), (ii), (iii), (iv) and/or (v):

(i) C$_1$-C$_{30}$-alkyl whose carbon chain may be interrupted by one or more —O—, —S—, —NR$^1$—, —N=CR$^1$—, —C≡C—, —CR$^1$=CR$^1$—, —CO—, —SO— and/or —SO$_2$— moieties and which may be mono- or polysubstituted by: C$_1$-C$_{12}$-alkoxy, C$_1$-C$_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, aryl and/or saturated or unsaturated C$_4$-C$_7$-cycloalkyl whose carbon skeleton may be interrupted by one or more —O—, —S—, —NR$^1$—, —N=CR$^1$—, —CR$^1$=CR$^1$—, —CO—, —SO— and/or —SO$_2$— moieties, where the aryl and cycloalkyl radicals may each be mono- or polysubstituted by C$_1$-C$_{18}$-alkyl and/or the above radicals specified as substituents for alkyl;

(ii) C$_3$-C$_8$-cycloalkyl whose carbon skeleton may be interrupted by one or more —O—, —S—, —NR$^1$—, —N=CR$^1$—, —CR$^1$=CR$^1$—, —CO—, —SO— and/or —SO$_2$— moieties and to which may be fused further saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties, where the entire ring system may be mono- or polysubstituted by: C$_1$-C$_{18}$-alkyl, C$_1$-C$_{12}$-alkoxy, C$_1$-C$_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$ and/or —SO$_3$R$^2$;

(iii) aryl or hetaryl, to which may be fused further saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties, where the entire ring system may be mono- or polysubstituted by: C$_1$-C$_{18}$-alkyl, C$_1$-C$_{12}$-alkoxy, C$_1$-C$_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, aryl and/or hetaryl, each of which may be mono- or polysubstituted by C$_1$-C$_{18}$-alkyl, C$_1$-C$_{12}$-alkoxy, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$ and/or —SO$_3$R$^2$;

(iv) a —U-aryl radical which may be mono- or polysubstituted by the above radicals specified as substituents for the aryl radicals (iii), where U is an —O—, —S—, —NR$^1$—, —CO—, —SO— or —SO$_2$— moiety;

(v) C$_1$-C$_{12}$-alkoxy, C$_1$-C$_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$ or —SO$_3$R$^2$, R are identical or different radicals:
hydrogen;
C$_1$-C$_{30}$-alkyl whose carbon chain may be interrupted by one or more —O—, —S—, —NR$^1$—, —N=CR$^1$—, —C≡C—, —CR$^1$=CR$^1$—, —CO—, —SO— and/or —SO$_2$— moieties and which may be mono- or polysubstituted by the (ii), (iii), (iv) and/or (v) radicals specified as substituents for the R' radicals;
C$_3$-C$_8$-cycloalkyl, to each of which may be fused further saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties, where the entire ring system may be mono- or polysubstituted by the (i), (ii), (iii), (iv) and/or (v) radicals specified as substituents for the R' radicals; aryl or hetaryl, to each of which may be fused further saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties, where the entire ring system may be mono- or polysubstituted by the (i), (ii), (iii), (iv), (v) radicals specified as substituents for the R' radicals, and/or aryl- and/or hetarylazo, each of which may be mono- or polysubstituted by C$_1$-C$_{10}$-alkyl, C$_1$-C$_6$-alkoxy and/or cyano;

R$^1$ is hydrogen or C$_1$-C$_{18}$-alkyl, where the R$^1$ radicals may be the same or different when they occur more than once;

R$^2$, R$^3$ are each independently:
hydrogen;
C$_1$-C$_{18}$-alkyl whose carbon chain may be interrupted by one or more —O—, —S—, —CO—, —SO— and/or —SO$_2$— moieties and which may be mono- or polysubstituted by $C_1$-$C_{12}$-alkoxy, $C_1$-$C_6$-alkylthio, hydroxyl, mercapto, halogen, cyano, nitro and/or —COOR$^1$;

aryl or hetaryl, to each of which may be fused further saturated or unsaturated 5- to 7-membered rings whose carbon skeleton may be interrupted by one or more —O—, —S—, —CO— and/or —SO$_2$— moieties, where the entire ring system may be mono- or polysubstituted by $C_1$-$C_{12}$-alkyl and/or the above radicals specified as substituents for alkyl;

m, n are each independently 0 or 1.

The present invention also relates to the preparation of the compounds of the formula I. The present invention further relates to the use of the compounds of the formula I for coloring high molecular weight organic and inorganic materials, as materials which absorb IR laser beams in the fusion treatment of plastics parts, for preparing aqueous polymer dispersions which absorb in the near infrared region of the electromagnetic spectrum, for obtaining markings and inscriptions which absorb infrared light but are invisible to the human eye, as infrared absorbers for heat management, and as active components in photovoltaics.

The invention further relates to the novel tetracene-5,11-bis(rylenedicarboximides) of the general formula IV

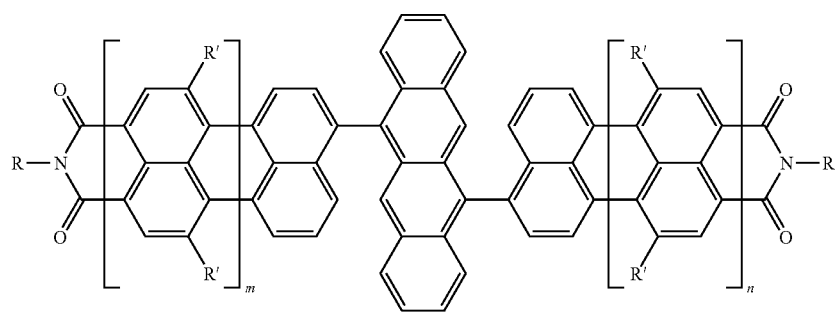

(IV)

and to novel bisrylene derivatives of the general formula V

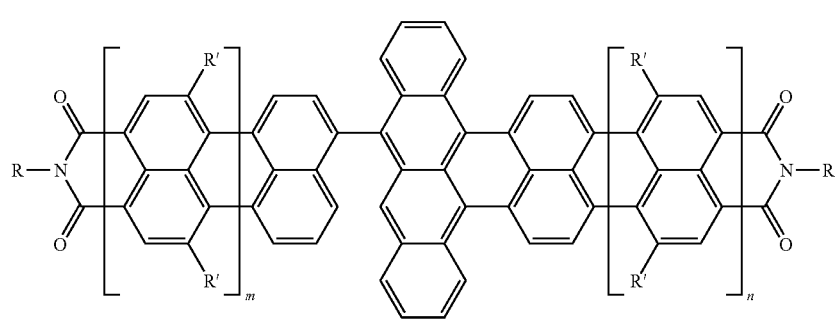

(V)

in which R and R' are each as defined above, as intermediates for the dibenzorylenetetracarboximides I.

BACKGROUND OF THE INVENTION

The fusion or cutting of plastics with laser beams is an advantageous method of manufacturing plastics articles with complex geometry. A prerequisite therefor is that the plastic to be treated absorbs the laser beam which, in the case of the commercial lasers, is at 808 nm, 940 to 980 nm and 1064 nm.

It therefore has to be additized or coated with substances which absorb at these wavelengths.

For this purpose, WO-A-2005/102 672 describes IR absorbers based on rylene compounds including quaterrylenetetracarboximides, and also doped tin oxides such as ATO and ITO (antimony tin oxide and indium tin oxide respectively), and metal hexaborides such as lanthanum hexaboride. The quaterrylenetetracarboximides can be used advantageously in combination with the lasers which emit at 808 nm; the longer wavelengths are obtainable with the inorganic absorbers.

For a series of applications, for example for applications in the outdoor sector and in the medical or foods sector, the inorganic absorbers, however, do not have the required stabilities.

The prior German patent application 102005018241.0 describes pentarylene- and hexarylenetetracarboximides whose absorption has been shifted bathochromically relative to the quaterrylenetetracarboximides and extends up to the region around 975 nm.

WO 2007/014902 describes polychromophores based on rylene.

In addition, there is a great need for organic compounds which are suitable as organic semiconductors, in particular n-type semiconductors, and especially for use in organic field-effect transistors and solar cells.

The unpublished PCT/EP2006/070143 describes compounds of the general formula

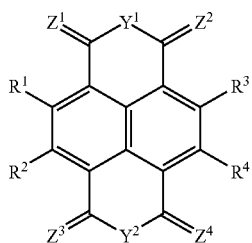

where
at least one of the $R^1$, $R^2$, $R^3$ and $R^4$ radicals is Br, F or CN,
$Y^1$ and $Y^2$ are each O or $NR^i$ where $R^i$ is hydrogen or an organyl radical,
$Z^1$, $Z^2$, $Z^3$ and $Z^4$ are each independently O or $NR^{ii}$ where $R^{ii}$ is an organyl radical, where, in the case that $Y^1$ and/or $Y^2$ is $NR^i$ and at least one of the $Z^1$ to $Z^4$ radicals is $NR^{ii}$, $R^i$ together with an $R^{ii}$ radical may also be a bridging group having 2 to 5 atoms between the flanking bonds,
and their use as n-semiconductors in organic field-effect transistors.

The unpublished PCT/EP2007/051532 describes the use of compounds of the general formula

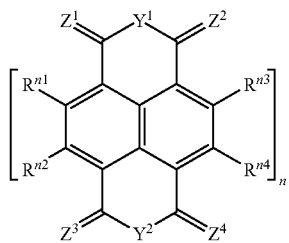

where
n is 2, 3 or 4,
at least one of the $R^{n1}$, $R^{n2}$, $R^{n3}$ and $R^{n4}$ radicals is fluorine, if appropriate at least one further $R^{n1}$, $R^{n2}$, $R^{n3}$ and $R^{n4}$ radical is a substituent which is selected independently from Cl and Br, and the remaining radicals are each hydrogen,
$Y^1$ and $Y^2$ are each O or $NR^i$ where $R^i$ is hydrogen or an organyl radical,
$Z^1$, $Z^2$, $Z^3$ and $Z^4$ are each O,
where, in the case that $Y^1$ and/or $Y^2$ is $NR^i$, one of the $Z^1$ to $Z^4$ radicals may also be $NR^{ii}$, where the $R^i$ and $R^{ii}$ radicals together are a bridging group having from 2 to 5 atoms between the flanking bonds,
as semiconductors, especially n-semiconductors, in organic electronics, especially for organic field-effect transistors, solar cells and organic light-emitting diodes.

The unpublished PCT/EP2007/053330 describes the use of compounds of the general formulae I and II

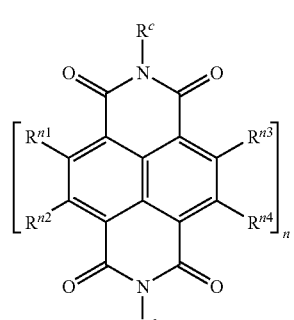

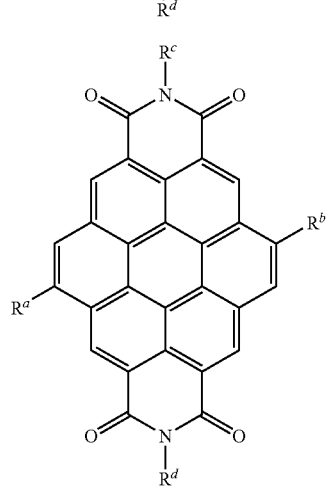

where
n is 1, 2, 3 or 4,
the $R^{n1}$, $R^{n2}$, $R^{n3}$ and $R^{n4}$ radicals, when n=1 or 2, are each independently selected from hydrogen, F, Cl, Br and CN, and, when n=3 or 4, are each independently selected from hydrogen, F, Cl and Br,
the $R^a$ and $R^b$ radicals are each independently selected from hydrogen and alkyl,
the $R^c$ and $R^d$ radicals are each independently selected from groups of the formulae II.1 to II.5:

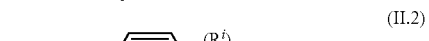

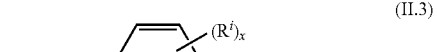

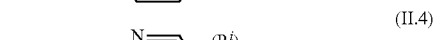

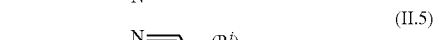

in which
is the site of attachment to the imide nitrogen atom,
p is 0 or 1,
x is 2 or 3,
A, where present, is a $C_1$-$C_{10}$-alkylene group which may be interrupted by one or more nonadjacent groups selected from —O— and —S—,
the $R^i$ radicals are each independently selected from $C_4$-$C_{30}$-alkyl which may be interrupted by one or more nonadjacent oxygen atom(s), where at least one of the $R^i$ radicals in the compounds of the formula II.1 may also be $C_4$-$C_{30}$-alkyloxy or $C_4$-$C_{30}$-alkylthio,
as n-semiconductors for organic field-effect transistors or solar cells.

K. Müllen et al. describe, in an article in Chem. Mater. 2006, 18, 3715-3725, the use of rylenetetracarboximides and coronenetetracarboximides with branched alkyl radicals on the imide nitrogens as n-semiconductors for organic field-effect transistors and in photovoltaic cells.

K. Müllen and Y. Avlasevich describe, in an article in Chem. Commun., 2006, 4440-4442 which had not been published at the priority date of the present application, dibenzopentarylenetetracarboximides as ring-extended rylene chromophores and their use as NIR-absorbing dyes.

It was an object of the present invention to provide organic compounds which absorb at a particularly long wavelength and can therefore also be used advantageously in combination with lasers which emit at high wavelengths (from 940 to 980 or in particular 1064 nm). It is a further object of the present invention to provide such compounds for use in organic electronics and photovoltaics, especially as semiconductors in excitonic solar cells.

BRIEF SUMMARY OF THE INVENTION

We have accordingly found the dibenzorylenetetracarboximides of the formula I defined at the outset.

The present invention therefore firstly provides compounds of the formula I

—CO—, —SO— and/or —SO$_2$— moieties and which may be mono- or polysubstituted by: $C_1$-$C_{12}$-alkoxy, $C_1$-$C_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, aryl and/or saturated or unsaturated $C_4$-$C_7$-cycloalkyl whose carbon skeleton may be interrupted by one or more —O—, —S—, —NR$^1$—, —N=CR$^1$—, —CR$^1$=CR$^1$—, —CO—, —SO— and/or —SO$_2$— moieties, where the aryl and cycloalkyl radicals may each be mono- or polysubstituted by $C_1$-$C_{18}$-alkyl, $C_1$-$C_{12}$-alkoxy, $C_1$-$C_6$-alkylthio, —C≡CR$^1$, —CR$^1$=CR$^1{}_2$, and/or the above radicals specified as substituents for alkyl;

(ii) $C_3$-$C_8$-cycloalkyl whose carbon skeleton may be interrupted by one or more —O—, —S—, —NR$^1$—, —N=CR$^1$—, —CR$^1$=CR$^1$—, —CO—, —SO— and/or —SO$_2$— moieties and to which may be fused further saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$ and/or —SO$_3$R$^2$;

(iii) aryl or hetaryl, to which may be fused further saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡CR$^1$, —CR$^1$=CR$^1{}_2$,

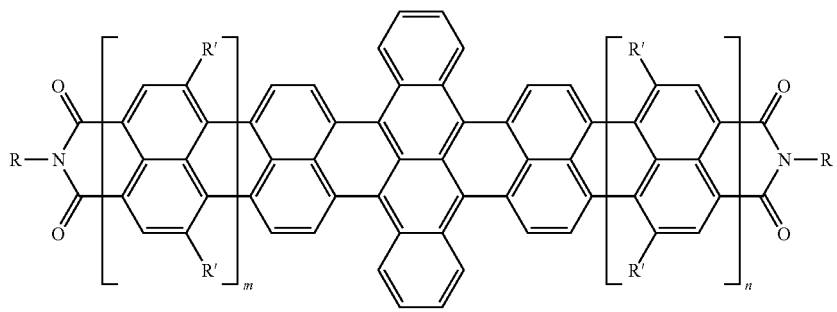

(I)

in which the variables are each defined as follows:
R' are identical or different radicals:
  hydrogen;
  aryloxy, arylthio, hetaryloxy or hetarylthio, to each of which may be fused further saturated or unsaturated 5- to 7-membered rings whose carbon skeleton may be interrupted by one or more —O—, —S—, —NR$^1$—, —N=CR$^1$—, —CO—, —SO— and/or —SO$_2$— moieties, where the entire ring system may be mono- or polysubstituted by the radicals (i), (ii), (iii), (iv) and/or (v):
  (i) $C_1$-$C_{30}$-alkyl whose carbon chain may be interrupted by one or more —O—, —S—, —NR$^1$—, —N=CR$^1$—, —C≡C—, —CR$^1$=CR$^1$—, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, aryl and/or hetaryl, each of which may be mono- or polysubstituted by $C_1$-$C_{18}$-alkyl, $C_1$-$C_{12}$-alkoxy, hydroxyl, mercapto, halogen, cyano, nitro, —NR$^2$R$^3$, —NR$^2$COR$^3$, —CONR$^2$R$^3$, —SO$_2$NR$^2$R$^3$—COOR$^2$ and/or —SO$_3$R$^2$;

(iv) a —U-aryl radical which may be mono- or polysubstituted by the above radicals specified as substituents for the aryl radicals (iii), where U is an —O—, —S—, —NR$^1$—, —CO—, —SO— or —SO$_2$— moiety;

(v) $C_1$-$C_{12}$-alkoxy, $C_1$-$C_6$-alkylthio, —C≡CR$^1$, —CR$^1$=CR$^1{}_2$, hydroxyl, mercapto, halogen, cyano, nitro, —NR²R³, —NR²COR³, —CONR²R³, —SO₂NR²R³, —COOR² or —SO₃R²;

R are identical or different radicals:
- hydrogen;
- $C_1$-$C_{30}$-alkyl whose carbon chain may be interrupted by one or more —O—, —S—, —NR¹—, —N=CR¹—, —C≡C—, —CR¹=CR¹—, —CO—, —SO— and/or —SO₂— moieties and which may be mono- or polysubstituted by the (ii), (iii), (iv) and/or (v) radicals specified as substituents for the R' radicals—hydroxyl, mercapto, halogen, cyano, nitro, —NR²R³, —NR²COR³, —CONR²R³, —SO₂NR²R³, —COOR² and/or —SO₃R²;
- $C_3$-$C_8$-cycloalkyl, to which may be fused further saturated or unsaturated 5- to 7-membered rings whose carbon skeleton may be interrupted by one or more —O—, —S—, —NR¹—, —N=CR¹—, —CR¹=CR¹—, —CO—, —SO— and/or —SO₂— moieties, where the entire ring system may be mono- or polysubstituted by the (i), (ii), (iii), (iv) and/or (v) radicals specified as substituents for the R' radicals;
- aryl or hetaryl, to each of which may be fused further saturated or unsaturated 5- to 7-membered rings whose carbon skeleton may be interrupted by one or more —O—, —S—, —NR¹—, —N=CR¹—, —CR¹=CR¹—, —CO—, —SO— and/or —SO₂— moieties, where the entire ring system may be mono- or polysubstituted by the (i), (ii), (iii), (iv), (v) radicals specified as substituents for the R' radicals, and/or aryl- and/or hetarylazo, each of which may be mono- or polysubstituted by $C_1$-$C_{10}$-alkyl, $C_1$-$C_6$-alkoxy and/or cyano;

R¹ is hydrogen or $C_1$-$C_{18}$-alkyl, where the R¹ radicals may be the same or different when they occur more than once;

R², R³ are each independently:
- hydrogen;
- $C_1$-$C_{18}$-alkyl whose carbon chain may be interrupted by one or more —O—, —S—, —CO—, —SO— and/or —SO₂— moieties and which may be mono- or polysubstituted by $C_1$-$C_{12}$-alkoxy, $C_1$-$C_6$-alkylthio, hydroxyl, mercapto, halogen, cyano, nitro, aryl and/or —COOR¹;
- aryl or hetaryl, to each of which may be fused further saturated or unsaturated 5- to 7-membered rings whose carbon skeleton may be interrupted by one or more —O—, —S—, —CO— and/or —SO₂— moieties, where the entire ring system may be mono- or polysubstituted by $C_1$-$C_{12}$-alkyl and/or the above radicals specified as substituents for alkyl;
- $C_3$-$C_8$-cycloalkyl to which may be fused further saturated or unsaturated 5- to 7-membered rings whose carbon skeleton may be interrupted by one or more —O—, —S—, —NR¹—, —N=CR¹—, —CR¹=CR¹—, —CO—, —SO— and/or —SO₂— moieties, where the entire ring system may be mono- or polysubstituted by $C_1$-$C_{12}$-alkyl and/or the above radicals specified as substituents for alkyl;

m, n are each independently 0 or 1.

We have also found a process for preparing dibenzorylenetetracarboximides of the general formula Ia

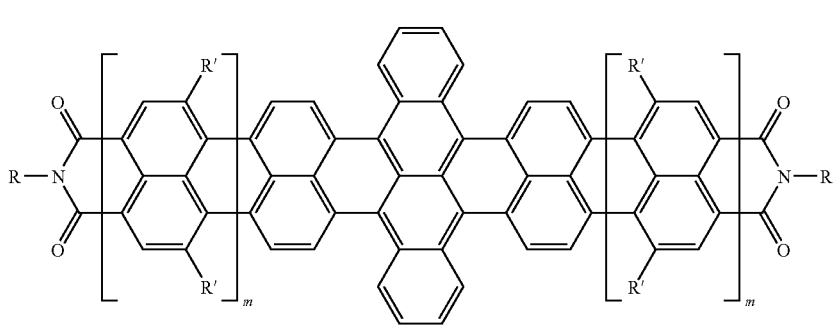

(Ia)

in which R, R¹ and m are each as defined at the outset, which comprises a) subjecting a peri-(dioxaborolan-2-yl)rylenedicarboximide of the general formula IIa

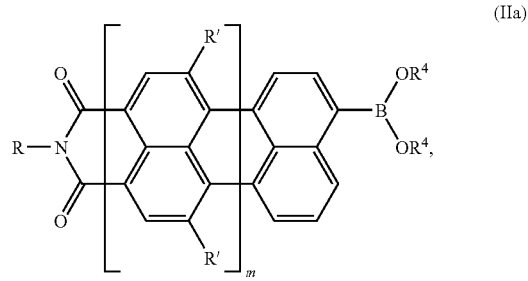

(IIa)

in which R⁴ are the same or different and are each independently hydrogen, $C_1$-$C_{30}$-alkyl, $C_5$-$C_8$-cycloalkyl, aryl or heteroaryl, and where two OR⁴ radicals bonded to the same boron atom together may also be —OCH₂CH₂O—, in which 1, 2, 3 or 4 hydrogen atoms may also be replaced by $C_1$-$C_{30}$-alkyl, $C_5$-$C_8$-cycloalkyl, aryl or heteroaryl groups, in the presence of an organic solvent, if desired in a mixture with water, and of a transition metal catalyst and of a base, to a Suzuki coupling reaction with 5,11-dibromotetracene of the formula III

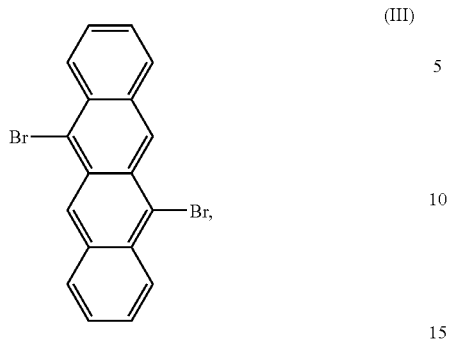

(III)

b) subjecting the tetracene-5,11-bis(rylenedicarboximide) of the general formula IVa formed in step a)

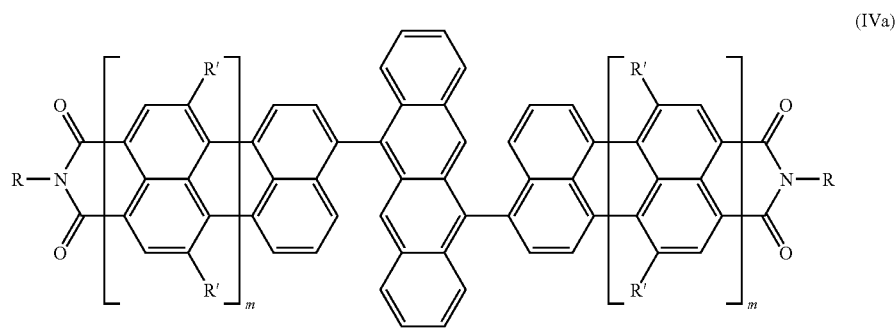

(IVa)

to a first cyclodehydrogenation in the presence of an inert organic solvent and of a Lewis acid and c) cyclodehydrogenating the bisrylene derivative of the general formula Va formed in step b)

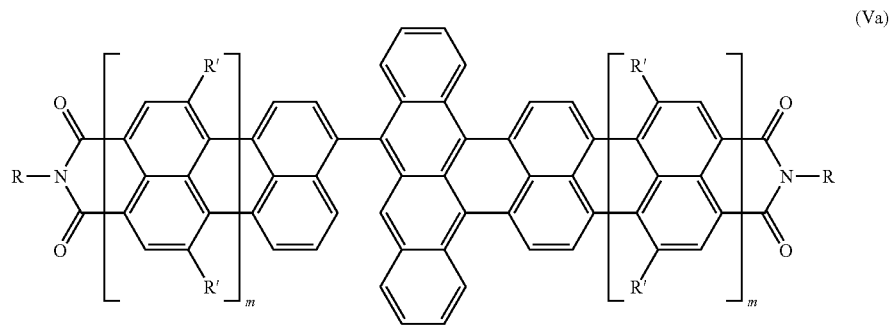

(Va)

in an organic reaction medium which has hydroxyl and amino functions and comprises an essentially undissolved base further to give the dibenzorylenetetracarboximide Ia.

We have also found a process for preparing dibenzorylenetetracarboximides of the general formula Ib (Ib)

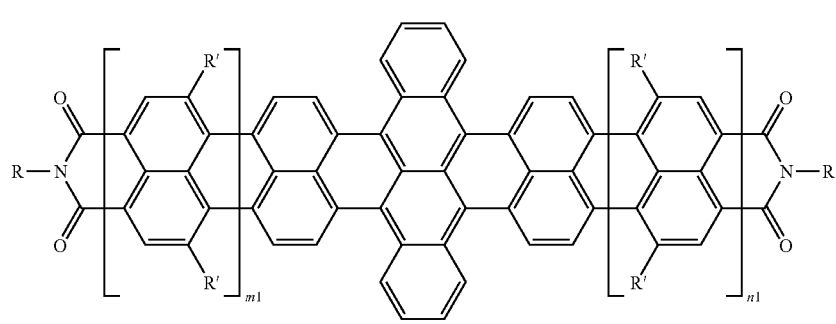

in which R and R' are each as defined at the outset, m1 and n1 are different from one another and are each 0 or 1, which comprises a1) subjecting a peri-(dioxaborolan-2-yl)rylenedicarboximide of the general formula IIb1

(IIb1)

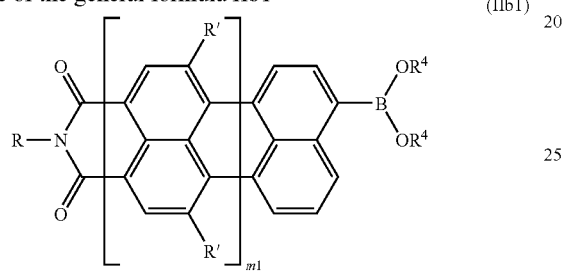

in which $R^4$ are the same or different and are each independently hydrogen, $C_1$-$C_{30}$-alkyl, $C_5$-$C_8$-cycloalkyl, aryl or heteroaryl, and where two $OR^4$ radicals bonded to the same boron atom together may also be —$OCH_2CH_2O$—, in which 1, 2, 3 or 4 hydrogen atoms may also be replaced by $C_1$-$C_{30}$-alkyl, $C_5$-$C_8$-cycloalkyl, aryl or heteroaryl groups, to a first Suzuki coupling reaction with 5,11-dibromotetracene (III) and a2) subjecting the 5-bromotetracene-11-rylenedicarboximide of the general formula III' formed in step a1)

(III')

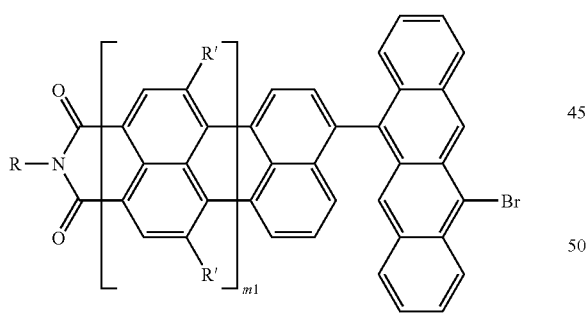

to a second Suzuki coupling reaction with a peri-(dioxaborolan-2-yl)rylene-dicarboximide of the general formula IIb2

(IIb2)

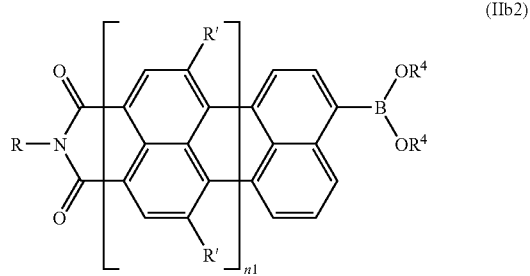

in the presence of an organic solvent, if desired in a mixture with water, and of a transition metal catalyst and of a base, b) subjecting the tetracene-5,11-bis(rylenedicarboximide) of the general formula IVb formed in step a2)

(IVb)

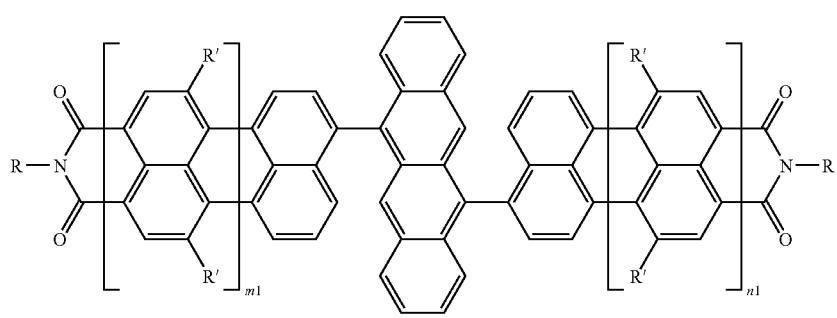

to a first cyclodehydrogenation in the presence of an inert organic solvent and of a Lewis acid and c) cyclodehydrogenating the bisrylene derivative of the general formula Vb formed in step b)

(Vb)

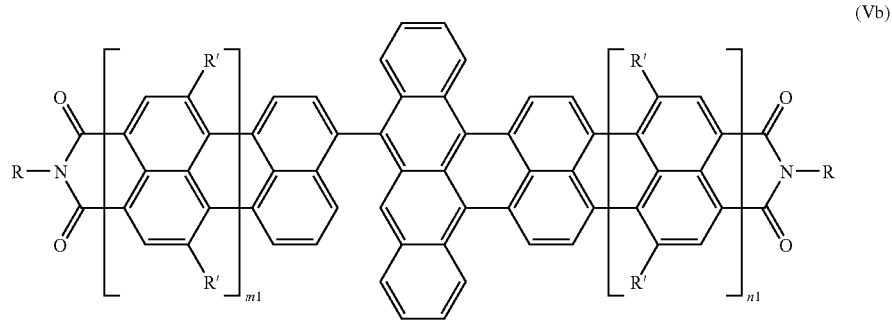

in an organic reaction medium which has hydroxyl and amino functions and comprises an essentially undissolved base further to give the dibenzorylenetetracarboximide Ib.

Not least, we have found the tetracene-5,11-bis(rylenedicarboximides) of the general formula IV (IV)

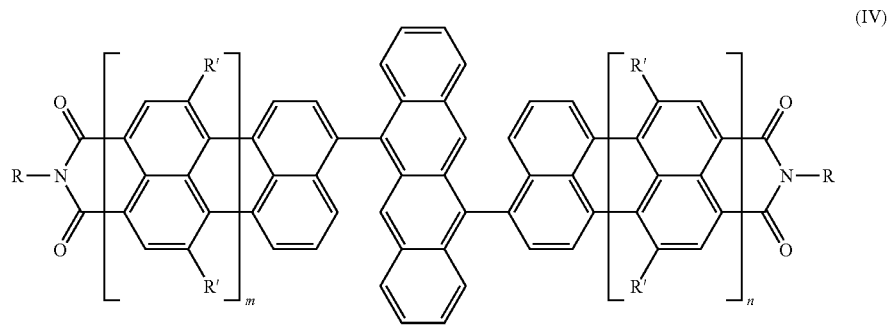

and bisrylene derivatives of the general formula V (V)

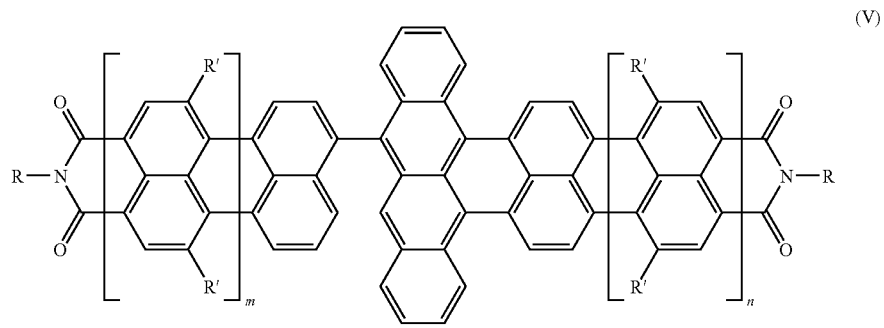

which occur as intermediates in these processes.

DETAILED DESCRIPTION OF THE INVENTION

Figure 1:
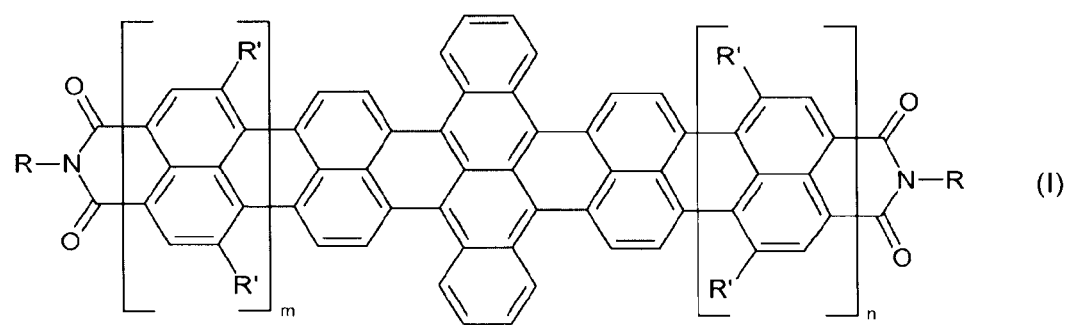
FIG. 1 depicts a novel dibenzorylenetetracarboximide of formula (I).

In the context of the present invention, the expression "alkyl" comprises straight-chain or branched alkyl having from 1 to 30 carbon atoms ($C_1$-$C_{30}$-alkyl), especially $C_1$-$C_{20}$-alkyl. Examples of alkyl groups are especially methyl, ethyl, propyl, isopropyl, n-butyl, isobutyl, sec-butyl, tert-butyl, n-pentyl, 2-methylbutyl, 3-methylbutyl, 1,2-dimethylpropyl, 1,1-dimethylpropyl, 2,2-dimethylpropyl, 1-ethylpropyl, n-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, 1,1,3,3-tetramethylbutyl, nonyl, decyl, n-undecyl, n-dodecyl, n-tridecyl, isotridecyl, n-tetradecyl, n-hexadecyl, n-octadecyl, 1-hexylheptyl, 1-heptyloctyl, 1-octylnonyl, 1-nonyldecyl and n-eicosyl.

The expression "alkyl" also comprises alkyl radicals whose carbon chain may be interrupted by one or more moieties, for example 1, 2, 3, 4 or more than 4 nonadjacent —O—, —S—, —NR$^1$—, —N=CR$^1$—, —C≡C—, —CR$^1$=CR$^1$—, —C(=O)—, —SO— and/or —SO$_2$— moieties, i.e. the termini of the alkyl group are formed by carbon atoms. R$^1$ is hydrogen or C$_1$-C$_{18}$-alkyl. Suitable alkyl radicals which are interrupted by one or more —C≡C— moieties are also referred to hereinafter as alkynyl. Suitable alkyl radicals which are interrupted by one or more —CR$^1$=CR$^1$— moieties are also referred to hereinafter as alkenyl.

Alkyl radicals whose carbon skeleton is interrupted by one or more —O— moieties have, in a formal sense, an alkyl moiety with one or more C$_1$-C$_{12}$-alkoxy substituents.

Examples of alkyl whose carbon chain is interrupted by one or more —O— moieties, for example one, two, three, four or more than four nonadjacent —O— moieties, are as follows:
methoxymethyl, diethoxymethyl, 2-methoxyethyl, 2-ethoxyethyl, 2-propoxyethyl, diethoxyethyl, 2-butoxyethyl, 2-octyloxyethyl, 2-methoxypropyl, 3-methoxypropyl, 3-ethoxypropyl, 3-propoxypropyl, 2-isopropoxyethyl, 2-butoxypropyl, 3-butoxypropyl, 4-methoxybutyl, 4-ethoxybutyl, 4-propoxybutyl, 6-methoxyhexyl, 3,6-dioxaheptyl (5-methoxy-3-oxapentyl), 3,6-dioxaoctyl (7-methoxy-4-oxaheptyl), 4,8-dioxanonyl (7-methoxy-4-oxaheptyl), 3,7-dioxaoctyl, 3,7-dioxanonyl, 4,7-dioxaoctyl, 4,7-dioxanonyl, 2- and 4-butoxybutyl, 4,8-dioxadecyl, 9-ethoxy-5-oxanonyl, 3,6,9-trioxadecyl, 3,6,9-trioxaundecyl, 3,6,9-trioxadodecyl, 4,8,12-trioxamidecyl (11-methoxy-4,8-dioxaundecyl), 4,8,12-trioxatetradecyl, 14-methoxy-5,10-dioxa-tetradecyl, 5,10,15-trioxaheptadecyl, 3,6,9,12-tetraoxamidecyl, 3,6,9,12-tetraoxa-tetradecyl, 4,8,12,16-tetraoxaheptadecyl (15-methoxy-4,8,12-trioxapentadecyl), 4,8,12,16-tetraoxaoctadecyl and the like.

Alkyl radicals whose carbon skeleton is interrupted by one or more —S— moieties have, in a formal sense, an alkyl moiety with one or more C$_1$-C$_6$-alkylthio substituents.

Examples of alkyl whose carbon chain is interrupted by one or more —S— moieties, for example 1, 2, 3, 4 or more than 4 nonadjacent —S— moieties, are as follows: butylthiomethyl, 2-methylthioethyl, 2-ethylthioethyl, 2-propylthioethyl, 2-butylthioethyl, 2-dodecylthioethyl, 3-methylthiopropyl, 3-ethylthiopropyl, 3-propylthiopropyl, 3-butylthiopropyl, 4-methylthiobutyl, 4-ethylthiobutyl, 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiamidecyl and 3,6,9,12-tetrathiatetradecyl.

Examples of alkyl whose carbon chain is interrupted by one or more —NR$^1$— moieties, for example one, two, three, four or more than four nonadjacent —NR$^1$— moieties, where R$^1$ is as defined above, are as follows:
2-monomethyl- and 2-monoethylaminoethyl, 2-dimethylaminoethyl, 3-methylamino-propyl, 2- and 3-dimethylaminopropyl, 3-monoisopropylaminopropyl, 2- and 4-monopropylaminobutyl, 2- and 4-dimethylaminobutyl, 6-methylaminohexyl, 6-dimethyl-aminohexyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazamidecyl, 3,6,9,12-tetramethyl-3,6,9,12-tetraazamidecyl and the like.

Examples of alkyl whose carbon chain is interrupted by one or more —N=CR$^1$-moieties, for example one, two, three, four or more than four nonadjacent —N=CR$^1$— moieties, where R$^1$ is as defined above, are as follows: (1-ethylethylidene)aminoethylene, (1-ethylethylidene)aminopropylene, (1-ethylethylidene)aminobutylene, (1-ethylethylidene)aminodecylene and (1-ethylethylidene)aminododecylene.

Examples of alkyl whose carbon chain is interrupted by —C(=O)— are as follows:
2-oxopropyl, 2-oxobutyl, 3-oxobutyl, 1-methyl-2-oxopropyl, 2-oxopentyl, 3-oxopentyl, 1-methyl-2-oxobutyl, 1-methyl-3-oxobutyl, 2-oxohexyl, 3-oxohexyl, 4-oxohexyl, 2-ethyl-3-oxopentyl, 2-oxoheptyl, 3-oxoheptyl, 4-oxoheptyl, 4-oxoheptyl and the like.

Examples of alkyl whose carbon chain is interrupted by —S(=O)— (sulfinyl group, which is also referred to hereinafter as the sulfoxido group) are as follows: 2-methylsulfinylethyl, 2-ethylsulfinylethyl, 2-propylsulfinylethyl, 2-isopropylsulf-oxidoethyl, 2-butylsulfinylethyl, 2- and 3-methylsulfinylpropyl, 2- and 3-ethylsulfoxidopropyl, 2- and 3-propylsulfinylpropyl, 2- and 3-butylsulfinylpropyl, 2- and 4-methylsulfinylbutyl, 2- and 4-ethylsulfinylbutyl, 2- and 4-propylsulfinylbutyl and 4-butylsulfinylbutyl.

Examples of alkyl whose carbon chain is interrupted by —SO$_2$— (sulfonyl group) are as follows:
2-methylsulfonylethyl, 2-ethylsulfonylethyl, 2-propylsulfonylethyl, 2-isopropylsulfonyl-ethyl, 2-butylsulfonylethyl, 2-methylsulfonylpropyl, 3-methylsulfonylpropyl, 2-ethylsulfonylpropyl, 3-ethylsulfonylpropyl, 2-propylsulfonylpropyl, 3-propylsulfonylpropyl, 2-butylsulfonylpropyl, 3-butylsulfonylpropyl, 2-methylsulfonylbutyl, 4-methylsulfonylbutyl, 2-ethylsulfonylbutyl, 4-ethylsulfonylbutyl, 2-propylsulfonylbutyl, 4-propylsulfonylbutyl and 4-butylsulfonylbutyl.

The expression "alkyl" also comprises substituted alkyl radicals. Substituted alkyl groups may, depending on the length of the alkyl chain, be mono- or polysubstituted, for example mono-, di-, tri-, tetra-, penta- or more than pentasubstituted, as defined above.

Examples of substituted alkyl radicals are as follows:
alkyl which is substituted by hydroxyl, for example 2-hydroxyethyl, 2-hydroxypropyl, 3-hydroxypropyl, 3-hydroxybutyl, 4-hydroxybutyl, 2-hydroxy-2-methylpropyl, 5-hydroxy-3-oxapentyl, 6-hydroxyhexyl, 7-hydroxy-4-oxaheptyl, 8-hydroxy-4-oxaoctyl, 8-hydroxy-3,6-dioxaoctyl, 9-hydroxy-5-oxanonyl, 11-hydroxy-4,8-dioxaundecyl, 11-hydroxy-3,6,9-trioxaundecyl, 14-hydroxy-5,10-dioxatetradecyl, 15-hydroxy-4,8,12-trioxapentadecyl and the like.

Alkyl which is substituted by mercapto, for example 2-mercaptoethyl, 2-mercaptopropyl, 3-mercaptopropyl, 3-mercaptobutyl, 4-mercaptobutyl, 2-hydroxy-2-methylpropyl.

Alkyl which is substituted by halogen as defined below, where some or all of the hydrogen atoms in the alkyl group may be replaced by halogen atoms, such as C$_1$-C$_{30}$-fluoroalkyl, e.g. trifluoromethyl, difluoromethyl, fluoromethyl, pentafluoroethyl, heptafluoropropyl, heptafluoroisopropyl, nonafluorobutyl, nonafluoroisobutyl, undecylfluoropentyl, undecylfluoroisopentyl and the like, C$_1$-C$_{30}$-chloroalkyl, e.g. chloromethyl, dichloromethyl, trichloromethyl, 2-chloroethyl, 2- and 3-chloropropyl, 2-, 3- and 4-chlorobutyl, 1,1-dimethyl-2-chloroethyl and the like, C$_1$-C$_{30}$-bromoalkyl, e.g. bromoethyl, 2-bromoethyl, 2- and 3-bromopropyl and 2-, 3- and 4-bromobutyl and the like.

Alkyl which is substituted by cyano, for example 2-cyanoethyl, 3-cyanopropyl, 3-cyanobutyl and 4-cyanobutyl and the like.

Alkyl which is substituted by nitro, for example 2-nitroethyl, 2- and 3-nitropropyl and 2-, 3- and 4-nitrobutyl and the like.

Alkyl which is substituted by amino, for example 2-aminoethyl, 2-aminopropyl, 3-aminopropyl, 4-aminobutyl, 6-aminohexyl and the like.

Alkyl which is substituted by carboxyl, for example carboxymethyl, 2-carboxyethyl, 3-carboxypropyl, 4-carboxybutyl, 5-carboxypentyl, 6-carboxyhexyl, 7-carboxyheptyl, 8-carboxyoctyl, 9-carboxynonyl, 10-carboxydecyl, 12-carboxydodecyl and 14-carboxytetradecyl.

Alkyl which is substituted by alkoxycarbonyl, for example methoxycarbonylmethyl, ethoxycarbonylmethyl, n-butoxycarbonylmethyl, 2-methoxycarbonylethyl, 2-ethoxycarbonylethyl, 2-methoxycarbonylpropyl, 2-ethoxycarbonylpropyl, 2-(n-butoxycarbonyl)propyl, 2-(4-n-butoxycarbonyl)propyl, 3-methoxycarbonylpropyl, 3-ethoxycarbonylpropyl, 3-(n-butoxycarbonyl)propyl, 3-(4-n-butoxycarbonyl)propyl and the like.

Alkyl which is substituted by aminocarbonyl, for example aminocarbonylmethyl, aminocarbonylethyl, aminocarbonylpropyl and the like.

Alkyl which is substituted by alkylaminocarbonyl, such as methylaminocarbonylmethyl, methylaminocarbonylethyl, ethylcarbonylmethyl, ethylcarbonylethyl and the like.

Alkyl which is substituted by dialkylaminocarbonyl, for example dimethylamino-carbonylmethyl, dimethylaminocarbonylethyl, dimethylcarbonylpropyl, diethylaminocarbonylmethyl, diethylaminocarbonylethyl, diethylcarbonylpropyl and the like.

Alkyl which is substituted by $C_4$-$C_7$-cycloalkyl, for example cyclobutylmethyl, cyclo-butylethyl, cyclopentylmethyl, 2-cyclopentylethyl, 3-cyclopentylpropyl, cyclohexylmethyl, 2-cyclohexylethyl, 3-cyclohexylpropyl, 2-cyclopentyl-1,1-dimethylethyl, 2-cyclohexyl-1,1-dimethylethyl, 2-cycloheptyl-1,1-dimethylethyl, and the like.

Alkyl which is substituted by $C_4$-$C_7$-cycloalkyl, whose carbon skeleton is interrupted by one or more —O—, —S—, —NR$^1$—, —N=CR$^1$—, —CR$^1$=CR$^1$—, —CO—, —SO— and/or —SO$_2$— moieties, such as 2-(cyclopentenyl)ethyl, 2-(cyclohexenyl)ethyl, 2-(cycloheptenyl)ethyl, 2-(4-morpholinyl)ethyl, 1,1-dimethyl-2-(4-morpholinyl)ethyl, 2-(4-thiomorpholinyl)ethyl, 1,1-dimethyl-2-(4-thiomorpholinyl)ethyl, 2-(tetrahydrofuran-2-yl)ethyl, 2-(tetra-hydrofuran-3-yl)ethyl, 2-(tetrahydrothiophen-2-yl)ethyl, 2-(tetrahydrothiophen-3-yl)ethyl, 2-(piperidin-1-yl)ethyl, 2-(piperidin-2-yl)ethyl, 2-(piperidin-3-yl)ethyl, 2-(piperidin-4-yl)ethyl, 2-(piperazin-1-yl)ethyl, 2-(piperazin-2-yl)ethyl, 2-(pyrrolidin-1-yl)ethyl, 2-(pyrrolidin-2-yl)ethyl, 2-(pyrrolidin-3-yl)ethyl, 2-(pyrazolidin-3-yl)ethyl, 2-(pyrazolidin-4-yl)ethyl and the like. When alkyl bears $C_4$-$C_7$-cycloalkyl whose carbon skeleton is interrupted by one or more —NR$^1$— moieties as a substituent, R$^1$ may also represent the bond to the alkyl radical.

Alkyl which is substituted by aryl, for example phenyl-$C_1$-$C_{10}$-alkyl, for example benzyl, 1-phenethyl, 2-phenethyl, 1-phenprop-1-yl, 2-phenprop-1-yl, 3-phenprop-1-yl, 1-phenbut-1-yl, 2-phenbut-1-yl, 3-phenbut-1-yl, 4-phenbut-1-yl, 1-phenbut-2-yl, 2-phenbut-2-yl, 3-phenbut-2-yl, 4-phenbut-2-yl, 1-(phenmeth)eth-1-yl, 1-(phenmethyl)-1-(methyl)eth-1-yl or 1-(phenmethyl)-1-(methyl)prop-1-yl, 2-(naphthalen-1-yl)ethyl, 2-(naphthalen-2-yl)ethyl and the like.

In the context of the present invention, the expression "alkenyl" comprises $C_1$-$C_{30}$-alkyl radicals whose carbon chain may be interrupted by one or more —CR$^1$=CR$^1$— moieties. Depending on the chain length, the carbon chain may then be interrupted by 1, 2, 3, 4 or more than 4-CR$^1$=CR$^1$— moieties. The expression "alkenyl" also comprises $C_1$-$C_{30}$-alkyl radicals whose carbon chain is interrupted by one or more —CR$^1$=CR$^1$— moieties and may be mono- or polysubstituted, for example mono-, di-, tri-, tetra- or more than tetra-substituted. Suitable substituents are those mentioned above for alkyl. The expression "alkenyl" further comprises radicals of the formula —CR$^1$=CR$^1{}_2$ in which R$^1$ is as defined above.

Suitable alkenyl radicals are ethenyl (vinyl), 1-propenyl, 2-propenyl, 1-methylethenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, penta-1,3-dien-1-yl, hexa-1,4-dien-1-yl, hexa-1,4-dien-3-yl, hexa-1,4-dien-6-yl, hexa-1,5-dien-1-yl, hexa-1,5-dien-3-yl, hexa-1,5-dien-4-yl, hepta-1,4-dien-1-yl, hepta-1,4-dien-3-yl, hepta-1,4-dien-6-yl, hepta-1,4-dien-7-yl, hepta-1,5-dien-1-yl, hepta-1,5-dien-3-yl, hepta-1,5-dien-4-yl, hepta-1,5-dien-7-yl, hepta-1,6-dien-1-yl, hepta-1,6-dien-3-yl, hepta-1,6-dien-4-yl, hepta-1,6-dien-5-yl, hepta-1,6-dien-2-yl, octa-1,4-dien-1-yl, octa-1,4-dien-2-yl, octa-1,4-dien-3-yl, octa-1,4-dien-6-yl, octa-1,4-dien-7-yl, octa-1,5-dien-1-yl, octa-1,5-dien-3-yl, octa-1,5-dien-4-yl, octa-1,5-dien-7-yl, octa-1,6-dien-1-yl, octa-1,6-dien-3-yl, octa-1,6-dien-4-yl, octa-1,6-dien-5-yl, octa-1,6-dien-2-yl, deca-1,4-dienyl, deca-1,5-dienyl, deca-1,6-dienyl, deca-1,7-dienyl, deca-1,8-dienyl, deca-2,5-dienyl, deca-2,6-dienyl, deca-2,7-dienyl, deca-2,8-dienyl and the like.

In the context of the present invention, the expression "alkynyl" comprises $C_1$-$C_{30}$-alkyl radicals whose carbon chain may be interrupted by one or more —C≡C— moieties. Depending on the chain length, the carbon chain may then be interrupted by 1, 2, 3, 4 or more than 4-C≡C— moieties. The expression "alkynyl" also comprises $C_1$-$C_{30}$-alkyl radicals whose carbon chain is interrupted by one or more —CR$^1$=CR$^1$— moieties and may be mono- or polysubstituted, for example mono-, di-, tri- or tetra- or more than tetrasubstituted. Suitable substituents are those mentioned above for alkyl. The expression "alkynyl" further comprises radicals of the formula —C≡CR$^1$ in which R$^1$ is as defined above.

Suitable alkynyl radicals are ethynyl, 1- and 2-propynyl, 1-, 2- and 3-butynyl, 1-, 2-, 3- and 4-pentynyl, 1-, 2-, 3-, 4- and 5-hexynyl, 1-, 2-, 3-, 4-, 5-, 6-, 7-, 8- and 9-decynyl, 1-, 2-, 3-, 4-, 5-, 6-, 7-, 8-, 9-, 10- and 11-dodecynyl and 1-, 2-, 3-, 4-, 5-, 6-, 7-, 8-, 9-, 10-, 11-, 12-, 13-, 14-, 15-, 16- and 17-octadecynyl.

In the context of the present invention, the expression "cycloalkyl" comprises unsubstituted and also substituted cycloalkyl groups having generally from 3 to 8 carbon ring members. The carbon ring skeleton may be interrupted by one or more, for example one or two, —C(=O)— moieties. Examples of $C_3$-$C_8$-cycloalkyl are cyclopropyl, cyclobutyl, cyclopentyl, cyclohexyl, cycloheptyl or cyclooctyl. Suitable substituents are generally selected from $C_1$-$C_{18}$-alkyl, $C_1$-$C_{12}$-alkoxy, $C_1$-$C_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$ and/or —SO$_3$R$^2$, in which R$^1$, R$^2$ and R$^3$ are each as defined above. Substituted cycloalkyl groups may have one or more (e.g. 1, 2, 3, 4, 5 or more than 5) substituents, where, in the case of halogen, the cycloalkyl radical is substituted partly or fully by halogen. In addition, one or more, for example one or two, further saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties may be fused to cycloalkyl, so as to form a bicyclic or tricyclic ring system. Examples of fused rings are cyclopentane, cyclohexane, cycloheptane, piperidine, piperazine, morpholine, thiomorpholine, 1,3-dioxolane, 1,3-dioxolan-2-one or 4H-1,3-oxazine.

Examples of cycloalkyl are cyclopentyl, 2- and 3-methylcyclopentyl, 2- and 3-ethylcyclopentyl, chloropentyl, dichloropentyl, dimethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, chlorohexyl, dimethylcyclohexyl, diethylcyclohexyl, methoxy-cyclohexyl, dimethoxycyclohexyl, diethoxycyclohexyl, butoxycyclohexyl, methylthiocyclohexyl, chlorocyclohexyl, dichlorocyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl, 3-, 4- and 5-propylcyclooctyl.

In the context of the present invention, the expression "cycloalkenyl" comprises substituted and unsubstituted $C_3$-$C_8$-cycloalkyl radicals whose carbon ring skeleton is interrupted by one or more, e.g. 1, 2, 3 or 4, —CR$^1$=CR$^1$— moieties. Suitable examples comprise cyclopent-1-en-1-yl, cyclopent-2-en-1-yl, cyclopent-3-en-1-yl, cyclohex-1-en-1-yl, cyclohex-2-en-1-yl, cyclohex-3-en-1-yl, cyclohexa-2,5-dien-1-yl, 1-, 2- and 3-cycloheptenyl and 1-, 2-, 3- and 4-cyclooctenyl and the like. Suitable substituents are those mentioned above for cycloalkyl.

In the context of the present invention, the expression "heterocyclyl (heterocycloalkyl)" comprises saturated, partly saturated or unsaturated $C_3$-$C_8$-cycloalkyl whose carbon skeleton is interrupted by one or more moieties, for example 1, 2, 3 or 4 identical or different —O—, —S—, —NR$^1$—, —N=CR$^1$—, —SO— and/or —SO$_2$— moieties and optionally has one or more, for example 1 or 2, —C(=O)— moiety/moieties. Nitrogen-containing heterocyclo-alkyl may in principle be bonded either via a carbon atom or via a nitrogen atom. In this case, R$^1$ in the —NR$^1$— moiety is a bond. Examples of heterocyclic groups are pyrrolidinyl, piperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, dihydrothien-2-yl, tetrahydrofuranyl, dihydrofuran-2-yl, tetrahydropyranyl, 1,2-oxazolin-5-yl, 1,3-oxazolin-2-yl, dioxanyl, 1,2-dihydropyrazin-1-yl, 1,4-dihydropyrimidin-1-yl and 3,4-dihydropyrimidin-3-yl.

In the context of the present invention, the expression "aryl" comprises mono- or polycyclic aromatic hydrocarbon radicals which may be unsubstituted or substituted. Aryl generally represents hydrocarbon radicals having from 6 to 10, to 14 or to 18 carbon ring members, preferably from 6 to 10 carbon ring members. Aryl is preferably unsubstituted or substituted phenyl, naphthyl, anthracenyl, phenanthrenyl, naphthacenyl, chrysenyl, pyrenyl, etc., and is more preferably phenyl or naphthyl. Depending on the number and size of their ring systems, substituted aryls may have one or more (e.g. 1, 2, 3, 4, 5 or more than 5) substituents. In addition, further rings whose carbon skeleton may be interrupted by one or more —O—, —S—, —NR$^1$—, —N=CR$^1$—, —CR$^1$=CR$^1$—, —CO—, —SO— and/or —SO$_2$— moieties may be fused to aryl. For example, one, two or three saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties may be fused to aryl. Examples of fused rings are cyclopentane, cyclohexane, cycloheptane, piperidine, piperazine, morpholine, thiomorpholine, 1,3-dioxolane, 1,3-dioxolan-2-one or 4H-1,3-oxazine.

Aryl which bears one or more radicals is, for example, 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl, 2,4,6-tri-tert-butylphenyl and 2-, 3-, 4-dodecylphenyl; 2-, 3- and 4-methoxyphenyl, 2,4-, 2,5-, 3,5- and 2,6-dimethoxyphenyl, 2,4,6-trimethoxyphenyl, 2-, 3- and 4-ethoxyphenyl, 2,4-, 2,5-, 3,5- and 2,6-diethoxyphenyl, 2,4,6-triethoxyphenyl, 2-, 3- and 4-propoxy-phenyl, 2,4-, 2,5-, 3,5- and 2,6-dipropoxyphenyl, 2-, 3- and 4-isopropoxyphenyl, 2,4-, 2,5-, 3,5- and 2,6-diisopropoxyphenyl, 2-, 3- and 4-butoxyphenyl, 2-, 3-, 4-hexyloxy-phenyl; 2-, 3-, 4-chlorophenyl, 2,4-, 2,5-, 3,5- and 2,6-dichlorophenyl, trichlorophenyl, 2-, 3-, 4-fluorophenyl, 2,4-, 2,5-, 3,5- and 2,6-difluorophenyl, trifluorophenyl, for example 2,4,6-trifluorophenyl, tetrafluorophenyl, pentafluorophenyl, 2-, 3- and 4-cyanophenyl; 2-nitrophenyl, 4-nitrophenyl, 2,4-dinitrophenyl, 2,6-dinitrophenyl; 4-dimethylaminophenyl; 4-acetylphenyl; methoxyethylphenyl, ethoxymethylphenyl; methylthiophenyl, isopropylthiophenyl or tert-butylthiophenyl; methylnaphthyl; isopropylnaphthyl or ethoxynaphthyl.

In the context of the present invention, the expression "aryloxy" represents aryl as defined above bonded via an oxygen atom.

In the context of the present invention, the expression "hetaryl (heteroaryl)" comprises unsubstituted or substituted, heteroaromatic, mono- or polycyclic groups having generally from 5 to 14 ring atoms, preferably 5 or 6 ring atoms, in which 1, 2, 3 or 4 of the ring carbon atoms are replaced by one, two, three or four heteroatoms selected from O, N and S, such as furyl, thienyl, oxazolyl, isoxazolyl, thiazolyl, isothiazolyl, benzofuranyl, benzthiazolyl, benzimidazolyl, pyridyl, quinolinyl, acridinyl, pyridazinyl, pyrimidinyl, pyrazinyl, pyrrolyl, imidazolyl, pyrazolyl, indolyl, purinyl, indazolyl, benzotriazolyl, 1,2,3-triazolyl, 1,3,4-triazolyl and carbazolyl, where these heterocycloaromatic groups, in the case of substitution, may generally bear 1, 2, 3, 4 or more than 4 substituents. Suitable substituents are those mentioned above.

Halogen is fluorine, chlorine, bromine or iodine.

$C_1$-$C_{12}$-alkoxy is a $C_1$-$C_{12}$-alkyl group bonded via an oxygen atom. Examples of alkoxy are: methoxy, ethoxy, n-propoxy, 1-methylethoxy, butoxy, 1-methylpropoxy, 2-methylpropoxy, 1,1-dimethylethoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy.

$C_1$-$C_6$-alkylthio is a $C_1$-$C_6$-alkyl group bonded via a sulfur atom. Examples of alkylthio are methylthio, ethylthio, propylthio, butylthio, pentylthio and hexylthio.

The inventive dibenzorylenetetracarboximides I may have a symmetrical ring system which corresponds to a pentarylene or terrylene skeleton extended by two fused benzene rings (m=n=1 or 0) (dibenzorylenetetracarboximides Ia).

The dibenzorylenetetracarboximides I may also have an asymmetrical ring system which corresponds to a quaterrylene skeleton extended by two fused benzene rings (m≠n) (dibenzorylenetetracarboximides Ib).

Preference is given to the dibenzorylenetetracarboximides Ia, particular preference being given to the dibenzopentarylenetetracarboximides Ia (m=n=1).

The substituents R on the imide nitrogen atoms of the dibenzorylenetetracarboximides I may be the same or different. Dibenzorylenetetracarboximides Ia with two different substituents R may be obtained analogously to the dibenzorylenetetracarboximides Ib by stepwise Suzuki coupling of 5,11-dibromotetracene with two peri-(dioxaborolan-2-yl)rylenedicarboximides II having the particular R radical. However, the substituents R are preferably the same.

The two R radicals are preferably each independently selected from groups of the formulae II.1 to II.5:

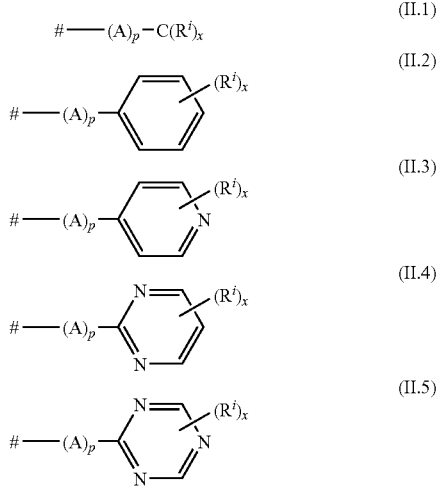

in which
\# is the site of attachment to the imide nitrogen atom,
p is 0 or 1,
x is 2 or 3 in the compounds of the formula II.1, is 1, 2 or 3 in the compounds of the formulae II.2, II.3 and II.4, and is 1 or 2 in the compounds of the formula II.5,
A, where present, is a $C_1$-$C_{10}$-alkylene group which may be interrupted by one or more nonadjacent groups selected from —O— and —S—,
where, in the case that x is 2 in the compounds of the formula II.1, the carbon atom which bears the $R^i$ radicals additionally bears a hydrogen atom,
the $R^i$ radicals are each independently selected from $C_1$-$C_{30}$-alkyl which may be interrupted by one or more nonadjacent oxygen atom(s), where at least one of the $R^i$ radicals in the compounds of the formula II.1 may also be $C_1$-$C_{30}$-alkyloxy or $C_1$-$C_{30}$-alkylthio.

In a preferred embodiment, x in the compounds of the formulae II.1 to II.4 is 2 or 3, especially 2, and, in the compounds of the formula II.5, is 2.

A further embodiment of the invention is that of compounds of the formula (I) where the $R^i$ radicals are each independently selected from $C_3$-$C_{30}$-alkyl which may be interrupted by one or more nonadjacent oxygen atom(s), where at least one of the $R^i$ radicals in the compounds of the formula II.1 may also be $C_3$-$C_{30}$-alkyloxy or $C_3$-$C_{30}$-alkylthio.

In a compound of the formula I, the R groups may have identical or different definitions. The R groups in a compound of the formula I preferably have the same definition.

One embodiment of the invention is that of compounds of the formula (I) where the R groups are groups of the formula (II.1) (so-called swallowtail radicals). In the groups of the formula (II.1), the $R^i$ radicals are preferably selected from $C_1$-$C_{12}$-alkyl, more preferably $C_4$-$C_8$-alkyl. The R groups are then preferably each a group of the formula

in which
\# represents the site of attachment to the imide nitrogen atom, and
the $R^i$ radicals are selected from $C_1$-$C_{12}$-alkyl, preferably $C_4$-$C_8$-alkyl, more preferably $C_5$-$C_7$-alkyl. The $R^i$ radicals are then especially linear alkyl radicals which are not interrupted by oxygen atoms.

A further embodiment of the invention is that of compounds of the formula (I) where the R groups are each independently selected from groups of the formulae II.2 to II.5. A preferred embodiment is that of the use of compounds of the formula (I) where the R groups are each independently selected from groups of the formula II.2 and x in the groups of the formula II.2 is 2.

The different $R^i$ radicals may each have identical or different definitions. Preferably, all $R^i$ radicals in one compound of the formula I have the same definition.

The $R^i$ radicals are each independently selected from linear or branched $C_1$-$C_{30}$-alkyl which may be interrupted by one or more nonadjacent oxygen atom(s). Preference is given to linear alkyl radicals. Preference is further given to $C_3$-$C_{18}$-alkyl, such as $C_4$-$C_{12}$-alkyl.

In a preferred embodiment, the aforementioned R groups have no alkylene group A. In a further preferred embodiment, the aforementioned R groups have a $C_1$-$C_4$-alkylene group A which may be interrupted by 1, 2 or 3 nonadjacent groups selected from —O— and —S—.

Specific examples of suitable R groups include:
radicals of the formula A:

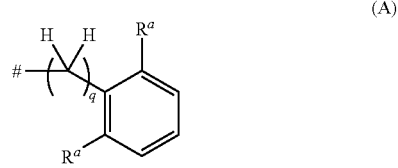

in which \# is the site of attachment to the imide nitrogen atom of the rylenetetracarboximide, q is an integer of 0, 1, 2, 3 or 4, and $R^a$ is $C_1$-$C_{30}$-alkyl.

Radicals of the formula A comprise those in which q is 0, for example
2,6-di(methyl)phenyl, 2,6-di(ethyl)phenyl, 2,6-di(n-propyl) phenyl, 2,6-di(isopropyl)phenyl, 2,6-di(n-butyl)phenyl, 2,6-di(n-pentyl)phenyl, 2,6-di(n-hexyl)phenyl, 2,6-di(n-heptyl) phenyl, 2,6-di(n-octyl)phenyl, 2,6-di(n-nonyl)phenyl, 2,6-di(n-decyl)phenyl, 2,6-di(n-undecyl)phenyl, 2,6-di(n-dodecyl) phenyl, 2,6-di(n-tridecyl)phenyl, 2,6-di(n-tetradecyl)phenyl, 2,6-di(n-pentadecyl)phenyl, 2,6-di(n-hexadecyl)phenyl, 2,6-di(n-heptadecyl)phenyl, 2,6-di(n-octadecyl)phenyl, 2,6-di (nonadecyl)phenyl, 2,6-di(eicosyl)phenyl, 2,6-di(docosanyl) phenyl, 2,6-di(tricosanyl)phenyl, 2,6-di(tetracosanyl)phenyl, 2,6-di(octacosanyl)phenyl;
in which q is 1, for example
2,6-di(methyl)benzyl, 2,6-di(ethyl)benzyl, 2,6-di(n-propyl) benzyl, 2,6-di(isopropyl)benzyl, 2,6-di(n-butyl)benzyl, 2,6-di(n-pentyl)benzyl, 2,6-di(n-hexyl)benzyl, 2,6-di(n-heptyl) benzyl, 2,6-di(n-octyl)benzyl, 2,6-di(n-nonyl)benzyl, 2,6-di (n-decyl)benzyl, 2,6-di(n-undecyl)benzyl, 2,6-di(n-dodecyl) benzyl, 2,6-di(n-tridecyl)benzyl, 2,6-di(n-tetradecyl)benzyl, 2,6-di(n-pentadecyl)benzyl, 2,6-di(n-hexadecyl)benzyl, 2,6-di(n-heptadecyl)benzyl, 2,6-di(n-octadecyl)benzyl, 2,6-di (nonadecyl)benzyl, 2,6-di(eicosyl)benzyl, 2,6-di(docosanyl) benzyl, 2,6-di(tricosanyl)benzyl, 2,6-di(tetradecosanyl)benzyl, 2,6-di(octacosanyl)benzyl;
in which q is 2, for example
2,6-di(methyl)phenethyl, 2,6-di(ethyl)phenethyl, 2,6-di(n-propyl)phenethyl, 2,6-di(isopropyl)phenethyl, 2,6-di(n-butyl)phenethyl, 2,6-di(n-pentyl)phenethyl, 2,6-di(n-hexyl) phenethyl, 2,6-di(n-heptyl)phenethyl, 2,6-di(n-octyl) phenethyl, 2,6-di(n-nonyl)phenethyl, 2,6-di(n-decyl) phenethyl, 2,6-di(n-undecyl)phenethyl, 2,6-di(n-dodecyl) phenethyl, 2,6-di(n-tridecyl)phenethyl, 2,6-di(n-tetradecyl) phenethyl, 2,6-di(n-pentadecyl)phenethyl, 2,6-di(n-hexadecyl)phenethyl, 2,6-di(n-heptadecyl)phenethyl, 2,6-di (n-octadecyl)phenethyl, 2,6-di(nonadecyl)phenethyl, 2,6-di (eicosyl)phenethyl, 2,6-di(docosanyl)phenethyl, 2,6-di (tricosanyl)phenethyl, 2,6-di(tetracosanyl)phenethyl, 2,6-di (octacosanyl)phenethyl;
in which q is 3, for example
3-(2,6-di(methyl)phenyl)propyl, 3-(2,6-di(ethyl)phenyl)propyl, 3-(2,6-di(n-propyl)phenyl)propyl, 3-(2,6-di(isopropyl) phenyl)propyl, 3-(2,6-di(n-butyl)phenyl)propyl, 3-(2,6-di(n-pentyl)phenyl)propyl, 3-(2,6-di(n-hexyl)phenyl)propyl, 3-(2,6-di(n-heptyl)phenyl)propyl, 3-(2,6-di(n-octyl)phenyl) propyl, 3-(2,6-di(n-nonyl)phenyl)propyl, 3-(2,6-di(n-decyl) phenyl)propyl, 3-(2,6-di(n-undecyl)phenyl)propyl, 3-(2,6-di (n-dodecyl)phenyl)propyl, 3-(2,6-di(n-tridecyl)phenyl) propyl, 3-(2,6-di(n-tetradecyl)phenyl)propyl, 3-(2,6-di(n-pentadecyl)phenyl)propyl, 3-(2,6-di(n-hexadecyl)phenyl) propyl, 3-(2,6-di(n-heptadecyl)phenyl)propyl, 3-(2,6-di(n-octadecyl)phenyl)propyl, 3-(2,6-di(nonadecyl)phenyl) propyl, 3-(2,6-di(eicosyl)phenyl)propyl, 3-(2,6-di (docosanyl)phenyl)propyl, 3-(2,6-di(tricosanyl)phenyl) propyl, 3-(2,6-di(tetracosanyl)phenyl)propyl, 3-(2,6-di (octacosanyl)phenyl)propyl;
in which q is 4, for example
4-(2,6-di(methyl)phenyl)butyl, 4-(2,6-di(ethyl)phenyl)butyl, 4-(2,6-di(n-propyl)phenyl)butyl, 4-(2,6-di(isopropyl)phenyl)butyl, 4-(2,6-di(n-butyl)phenyl)butyl, 4-(2,6-di(n-pentyl)phenyl)butyl, 4-(2,6-di(n-hexyl)phenyl)butyl, 4-(2,6-di(n-heptyl)phenyl)butyl, 4-(2,6-di(n-octyl)phenyl)butyl, 4-(2,6-di(n-nonyl)phenyl)butyl, 4-(2,6-di(n-decyl)phenyl)butyl, 4-(2,6-di(n-undecyl)phenyl)butyl, 4-(2,6-di(n-dodecyl)phenyl)butyl, 4-(2,6-di(n-tridecyl)phenyl)butyl, 4-(2,6-di(n-tetradecyl)phenyl)butyl, 4-(2,6-di(n-pentadecyl)phenyl)butyl, 4-(2,6-di(n-hexadecyl)phenyl)butyl, 4-(2,6-di(n-heptadecyl) phenyl)butyl, 4-(2,6-di(n-octadecyl)phenyl)butyl, 4-(2,6-di (nonadecyl)phenyl)butyl, 4-(2,6-di(eicosyl)phenyl)butyl, 4-(2,6-di(docosanyl)phenyl)butyl, 4-(2,6-di(tricosanyl)phenyl)butyl, 4-(2,6-di(tetracosanyl)phenyl)butyl, 4-(2,6-di(octacosanyl)phenyl)butyl;

and additionally radicals of the formula B:

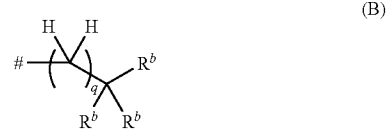

in which # is the site of attachment to the imide nitrogen atom of the rylenetetracarboximide, q is an integer of 0, 1, 2, 3, 4, 5 or 6, and $R^b$ is $C_4$-$C_{30}$-alkyl.

Examples of suitable radicals of the formula B comprise the formulae B-0.a, B-0.b, B-0.c, B-1.a, B-1.b, B-1.c, B-2.a, B-2.b, B-2.c, B-3.a, B-3.b, B-3.c, B-4.a, B-4.b, B-4.c, B-5.a, B-5.b, B-5.c, B-6.a, B-6.b, B-6.c

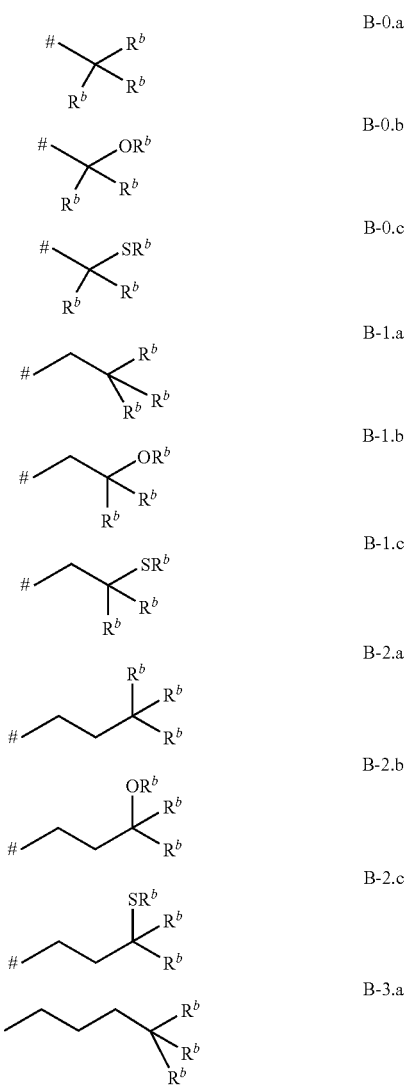

-continued

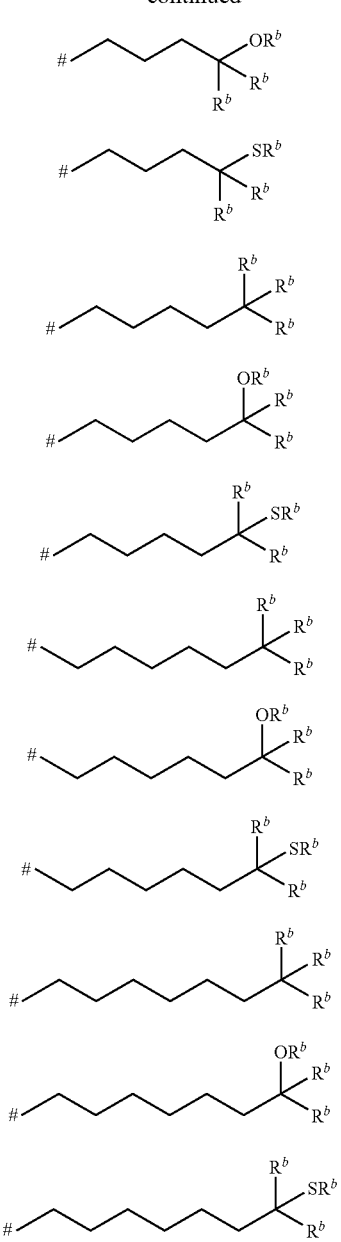

in which # is the site of attachment to the imide nitrogen atom of the rylenetetracarboximide, and $R^b$ is independently n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-docosanyl, n-tricosanyl, n-tetracosanyl, n-octacosanyl, and additionally compounds of the formula C:

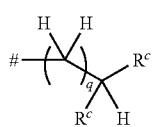
(C)

in which # is the site of attachment to the imide nitrogen atom of the rylenetetracarboximide, q is an integer of 0, 1, 2, 3, 4, 5 or 6, and $R^c$ is $C_4$-$C_{30}$-alkyl, $C_4$-$C_{30}$-alkylthio or $C_4$-$C_{30}$-alkoxy.

Radicals of the formula H comprise those in which q is 0, for example 1-ethylpropyl, 1-methylpropyl, 1-propylbutyl, 1-ethylbutyl, 1-methylbutyl, 1-butylpentyl, 1-propylpentyl, 1-ethylpentyl, 1-methylpentyl, 1-pentylhexyl, 1-butylhexyl, 1-propylhexyl, 1-ethylhexyl, 1-methylhexyl, 1-hexylheptyl, 1-pentylheptyl, 1-butylheptyl, 1-propylheptyl, 1-ethylheptyl, 1-methylheptyl, 1-heptyloctyl, 1-hexyloctyl, 1-pentyloctyl, 1-butyloctyl, 1-propyloctyl, 1-ethyloctyl, 1-methyloctyl, 1-octylnonyl, 1-heptylnonyl, 1-hexylnonyl, 1-pentylnonyl, 1-butylnonyl, 1-propylnonyl, 1-ethylnonyl, 1-methylnonyl, 1-nonyldecyl, 1-octyldecyl, 1-heptyldecyl, 1-hexyldecyl, 1-pentyldecyl, 1-butyldecyl, 1-propyldecyl, 1-ethyldecyl, 1-methyldecyl, 1-decylundecyl, 1-nonylundecyl, 1-octylundecyl, 1-heptylundecyl, 1-hexylundecyl, 1-pentylundecyl, 1-butylundecyl, 1-propylundecyl, 1-ethylundecyl, 1-methylundecyl, 1-undecyldodecyl, 1-decyldodecyl, 1-nonyldodecyl, 1-octyldodecyl, 1-heptyldodecyl, 1-hexyldodecyl, 1-pentyldodecyl, 1-butyldodecyl, 1-propyldodecyl, 1-ethyldodecyl, 1-methyldodecyl, 1-dodecyltridecyl, 1-undecyltridecyl, 1-decyltridecyl, 1-nonyltridecyl, 1-octyltridecyl, 1-heptyltridecyl, 1-hexyltridecyl, 1-pentyltridecyl, 1-butyltridecyl, 1-propyltridecyl, 1-ethyltridecyl, 1-methyltridecyl, 1-tridecyltetradecyl, 1-undecyltetradecyl, 1-decyltetradecyl, 1-nonyltetradecyl, 1-octyltetradecyl, 1-heptyltetradecyl, 1-hexyltetradecyl, 1-pentyltetradecyl, 1-butyltetradecyl, 1-propyltetradecyl, 1-ethyltetradecyl, 1-methyltetradecyl, 1-pentadecylhexadecyl, 1-tetradecylhexadecyl, 1-tridecylhexadecyl, 1-dodecylhexadecyl, 1-undecylhexadecyl, 1-decylhexadecyl, 1-nonylhexadecyl, 1-octylhexadecyl, 1-heptylhexadecyl, 1-hexylhexadecyl, 1-pentylhexadecyl, 1-butylhexadecyl, 1-propylhexadecyl, 1-ethylhexadecyl, 1-methylhexadecyl, 1-hexadecyloctadecyl, 1-pentadecyloctadecyl, 1-tetradecyloctadecyl, 1-tridecyloctadecyl, 1-dodecyloctadecyl, 1-undecyloctadecyl, 1-decyloctadecyl, 1-nonyloctadecyl, 1-octyloctadecyl, 1-heptyloctadecyl, 1-hexyloctadecyl, 1-pentyloctadecyl, 1-butyloctadecyl, 1-propyloctadecyl, 1-ethyloctadecyl, 1-methyloctadecyl, 1-nonadecyleicosanyl, 1-octadecyleicosanyl, 1-heptadecyleicosanyl, 1-hexadecyleicosanyl, 1-pentadecyleicosanyl, 1-tetradecyleicosanyl, 1-tridecyleicosanyl, 1-dodecyleicosanyl, 1-undecyleicosanyl, 1-decyleicosanyl, 1-nonyleicosanyl, 1-octyleicosanyl, 1-heptyleicosanyl, 1-hexyleicosanyl, 1-pentyleicosanyl, 1-butyleicosanyl, 1-propyleicosanyl, 1-ethyleicosanyl, 1-methyleicosanyl, 1-eicosanyidocosanyl, 1-nonadecyldocosanyl, 1-octadecyldocosanyl, 1-heptadecyldocosanyl, 1-hexadecyldocosanyl, 1-pentadecyldocosanyl, 1-tetradecyldocosanyl, 1-tridecyldocosanyl, 1-undecyldocosanyl, 1-decyldocosanyl, 1-nonyldocosanyl, 1-octyldocosanyl, 1-heptyidocosanyl, 1-hexyldocosanyl, 1-pentyldocosanyl, 1-butyldocosanyl, 1-propyldocosanyl, 1-ethyldocosanyl, 1-methyldocosanyl, 1-tricosanyltetracosanyl, 1-docosanyltetracosanyl, 1-nonadecyltetracosanyl, 1-octadecyltetracosanyl, 1-heptadecyltetracosanyl, 1-hexadecyltetracosanyl, 1-pentadecyltetracosanyl, 1-pentadecyltetracosanyl, 1-tetradecyltetracosanyl, 1-tridecyltetracosanyl, 1-dodecyltetracosanyl, 1-undecyltetracosanyl, 1-decyltetracosanyl, 1-nonyltetracosanyl, 1-octyltetracosanyl, 1-heptyltetracosanyl, 1-hexyltetracosanyl, 1-pentyltetracosanyl, 1-butyltetracosanyl, 1-propyltetracosanyl, 1-ethyltetracosanyl, 1-methyltetracosanyl, 1-heptacosanyloctacosanyl, 1-hexacosanyloctacosanyl, 1-pentacosanyloctacosanyl, 1-tetracosanyloctacosanyl, 1-tricosanyloctacosanyl, 1-docosanyloctacosanyl, 1-nonadecyloctacosanyl, 1-octadecyloctacosanyl, 1-heptadecyloctacosanyl, 1-hexadecyloctacosanyl, 1-hexadecyloctacosanyl, 1-pentadecyloctacosanyl, 1-tetradecyloctacosanyl, 1-tridecyloctacosanyl, 1-dodecyloctacosanyl, 1-undecyloctacosanyl, 1-decyloctacosanyl, 1-nonyloctacosanyl, 1-octyloctacosanyl, 1-heptyloctacosanyl, 1-hexyloctacosanyl, 1-pentyloctacosanyl, 1-butyloctacosanyl, 1-propyloctacosanyl, 1-ethyloctacosanyl, 1-methyloctacosanyl; 1-ethyloxypropyl, 1-methyloxypropyl, 1-propylbutyl, 1-ethyloxybutyl, 1-methyloxybutyl, 1-butyloxypentyl, 1-propylpentyl, 1-ethyloxypentyl, 1-methyloxypentyl, 1-pentyloxyhexyl, 1-butyloxyhexyl, 1-propylhexyl, 1-ethyloxyhexyl, 1-methyloxyhexyl, 1-hexyloxyheptyl, 1-pentyloxyheptyl, 1-butyloxyheptyl, 1-propylheptyl, 1-ethyloxyheptyl, 1-methyloxyheptyl, 1-heptyloctyl, 1-hexyloxyoctyl, 1-pentyloxyoctyl, 1-butyloxyoctyl, 1-propyloctyl, 1-ethyloxyoctyl, 1-methyloxyoctyl, 1-octyloxynonyl, 1-heptylnonyl, 1-hexyloxynonyl, 1-pentyloxynonyl, 1-butyloxynonyl, 1-propylnonyl, 1-ethyloxynonyl, 1-methyloxynonyl, 1-nonyloxydecyl, 1-octyloxydecyl, 1-heptyldecyl, 1-hexyloxydecyl, 1-pentyloxydecyl, 1-butyloxydecyl, 1-propyldecyl, 1-ethyloxydecyl, 1-methyloxydecyl, 1-decyloxyundecyl, 1-nonyloxyundecyl, 1-octyloxyundecyl, 1-heptylundecyl, 1-hexyloxyundecyl, 1-pentyloxyundecyl, 1-butyloxyundecyl, 1-propylundecyl, 1-ethyloxyundecyl, 1-methyloxyundecyl, 1-undecyloxydodecyl, 1-decyloxydodecyl, 1-nonyloxydodecyl, 1-octyloxydodecyl, 1-heptyidodecyl, 1-hexyloxydodecyl, 1-pentyloxydodecyl, 1-butyloxydodecyl, 1-propyldodecyl, 1-ethyloxydodecyl, 1-methyloxydodecyl, 1-dodecyloxytridecyl, 1-undecyloxytridecyl, 1-decyloxytridecyl, 1-nonyloxytridecyl, 1-octyloxytridecyl, 1-heptyltridecyl, 1-hexyloxytridecyl, 1-pentyloxytridecyl, 1-butyloxytridecyl, 1-propyltridecyl, 1-ethyloxytridecyl, 1-methyloxytridecyl, 1-tridecyloxytetradecyl, 1-undecyloxytetradecyl, 1-decyloxytetradecyl, 1-nonyloxytetradecyl, 1-octyloxytetradecyl, 1-heptyltetradecyl, 1-hexyloxytetradecyl, 1-pentyltetradecyl, 1-butyloxytetradecyl, 1-propyltetradecyl, 1-ethyloxytetradecyl, 1-methyloxytetradecyl, 1-pentadecyloxyhexadecyl, 1-tetradecyloxyhexadecyl, 1-tridecyloxyhexadecyl, 1-dodecyloxyhexadecyl, 1-undecyloxyhexadecyl, 1-decyloxyhexadecyl, 1-nonyloxyhexadecyl, 1-octyloxyhexadecyl, 1-heptylhexadecyl, 1-hexyloxyhexadecyl, 1-pentyloxyhexadecyl, 1-butyloxyhexadecyl, 1-propylhexadecyl, 1-ethyloxyhexadecyl, 1-methyloxyhexadecyl, 1-hexadecyloxyoctadecyl, 1-pentadecyloxyoctadecyl, 1-tetradecyloxyoctadecyl, 1-tridecyloxyoctadecyl, 1-dodecyloxyoctadecyl, 1-undecyloxyoctadecyl, 1-decyloxyoctadecyl, 1-nonyloxyoctadecyl, 1-octyloxyoctadecyl, 1-heptyloctadecyl, 1-hexyloxyoctadecyl, 1-pentyloxyoctadecyl, 1-butyloxyoctadecyl, 1-propyloctadecyl, 1-ethyloxyoctadecyl, 1-methyloxyoctadecyl, 1-nonadecyloxyeicosanyl, 1-octadecyloxyeicosanyl, 1-heptadecyloxyeicosanyl, 1-hexadecyloxyeicosanyl, 1-pentadecyloxyeicosanyl, 1-tetradecyloxyeicosanyl, 1-tridecyloxyeicosanyl, 1-dodecyloxyeicosanyl, 1-undecyloxyeicosanyl, 1-decyloxyeicosanyl, 1-nonyloxyeicosanyl, 1-octyloxyeicosanyl, 1-heptyleicosanyl, 1-hexyloxyeicosanyl, 1-pentyloxyeicosanyl, 1-butyloxyeicosanyl, 1-propyleicosanyl, 1-ethyloxyeicosanyl, 1-methyleicosanyl, 1-eicosanyloxydocosanyl, 1-nonadecyloxydocosanyl, 1-octadecyloxydocosanyl, 1-heptadecyloxydocosanyl, 1-hexadecyloxydocosanyl, 1-pentadecyloxydocosanyl, 1-tetradecyloxydocosanyl, 1-tridecyloxydocosanyl, 1-undecyloxydocosanyl, 1-decyloxydocosanyl, 1-nonyloxydocosanyl, 1-octyloxydocosanyl, 1-heptyldocosanyl, 1-hexyloxydocosanyl, 1-pentyloxydocosanyl, 1-butyloxydocosanyl, 1-propyldocosanyl, 1-ethyloxydocosanyl, 1-methyloxydocosanyl, 1-tricosanyloxytetracosanyl, 1-docosanyloxytetracosanyl, 1-nonadecyloxytetracosanyl, 1-octadecyloxytetracosanyl, 1-heptadecyloxytetracosanyl, 1-hexadecyloxytetracosanyl, 1-pentadecyloxytetracosanyl, 1-pentadecyloxytetracosanyl, 1-tetradecyloxytetracosanyl, 1-tridecyloxytetracosanyl, 1-dodecyloxytetracosanyl, 1-undecyloxytetracosanyl, 1-decyloxytetracosanyl, 1-nonyloxytetracosanyl, 1-octyloxytetracosanyl, 1-heptyltetracosanyl, 1-hexyloxytetracosanyl, 1-pentyloxytetracosanyl, 1-butyloxytetracosanyl, 1-propyltetracosanyl, 1-ethyloxytetracosanyl, 1-methyloxytetracosanyl, 1-heptacosanyloxyoctacosanyl, 1-hexacosanyloxyoctacosanyl, 1-pentacosanyloxyoctacosanyl, 1-tetracosanyloxyoctacosanyl, 1-tricosanyloxyoctacosanyl, 1-docosanyloxyoctacosanyl, 1-nonadecyloxyoctacosanyl, 1-octadecyloxyoctacosanyl, 1-heptadecyloxyoctacosanyl, 1-hexadecyloxyoctacosanyl, 1-hexadecyloxyoctacosanyl, 1-pentadecyloxyoctacosanyl, 1-tetradecyloxyoctacosanyl, 1-tridecyloxyoctacosanyl, 1-dodecyloxyoctacosanyl, 1-undecyloxyoctacosanyl, 1-decyloxyoctacosanyl, 1-nonyloxyoctacosanyl, 1-octyloxyoctacosanyl, 1-heptyloctacosanyl, 1-hexyloxyoctacosanyl, 1-pentyloxyoctacosanyl, 1-butyloxyoctacosanyl, 1-propyloxyoctacosanyl, 1-ethyloxyoctacosanyl, 1-methyloxyoctacosanyl; 1-ethylthiopropyl, 1-methylthiopropyl, 1-propylbutyl, 1-ethylthiobutyl, 1-methylthiobutyl, 1-butylthiopentyl, 1-propylpentyl, 1-ethylthiopentyl, 1-methylthiopentyl, 1-pentylthiohexyl, 1-butylthiohexyl, 1-propylhexyl, 1-ethylthiohexyl, 1-methylthiohexyl, 1-hexylthioheptyl, 1-pentylthioheptyl, 1-butylthioheptyl, 1-propylheptyl, 1-ethylthioheptyl, 1-methylthioheptyl, 1-heptyloctyl, 1-hexylthiooctyl, 1-pentylthiooctyl, 1-butylthiooctyl, 1-propyloctyl, 1-ethylthiooctyl, 1-methylthiooctyl, 1-octylthiononyl, 1-heptylnonyl, 1-hexylthiononyl, 1-pentylthiononyl, 1-butylthiononyl, 1-propylnonyl, 1-ethylthiononyl, 1-methylthiononyl, 1-nonylthiodecyl, 1-octylthiodecyl, 1-heptyldecyl, 1-hexylthiodecyl, 1-pentylthiodecyl, 1-butylthiodecyl, 1-propyldecyl, 1-ethylthiodecyl, 1-methylthiodecyl, 1-decylthioundecyl, 1-nonylthioundecyl, 1-octylthioundecyl, 1-heptylundecyl, 1-hexylthioundecyl, 1-pentylthioundecyl, 1-butylthioundecyl, 1-propylundecyl, 1-ethylthioundecyl, 1-methylthioundecyl, 1-undecylthiododecyl, 1-decylthiododecyl, 1-nonylthiododecyl, 1-octylthiododecyl, 1-heptyidododecyl, 1-hexylthiododecyl, 1-pentylthiododecyl, 1-butylthiododecyl, 1-propyldodecyl, 1-ethylthiododecyl, 1-methylthiododecyl, 1-dodecylthiotridecyl, 1-undecylthiotridecyl, 1-decylthiotridecyl, 1-nonylthiotridecyl, 1-octylthiotridecyl, 1-heptyltridecyl, 1-hexylthiotridecyl, 1-pentylthiotridecyl, 1-butylthiotridecyl, 1-propyltridecyl, 1-ethylthiotridecyl, 1-methylthiotridecyl, 1-tridecylthiotetradecyl, 1-undecylthiotetradecyl, 1-decylthiotetradecyl, 1-nonylthiotetradecyl, 1-octylthiotetradecyl, 1-heptyltetradecyl, 1-hexylthiotetradecyl, 1-pentyltetradecyl, 1-butylthiotetradecyl, 1-propyltetradecyl, 1-ethylthiotetradecyl, 1-methylthiotetradecyl, 1-pentadecylthiohexadecyl, 1-tetradecylthiohexadecyl, 1-tridecylthiohexadecyl, 1-dodecylthiohexadecyl, 1-undecylthiohexadecyl, 1-decylthiohexadecyl, 1-nonylthiohexadecyl, 1-octylthiohexadecyl, 1-heptylhexadecyl, 1-hexylthiohexadecyl, 1-pentylthiohexadecyl, 1-butylthiohexadecyl, 1-propylhexadecyl, 1-ethylthiohexadecyl, 1-methylthiohexadecyl, 1-hexadecylthiooctadecyl, 1-pentadecylthiooctadecyl, 1-tetradecylthiooctadecyl, 1-tridecylthiooctadecyl, 1-dodecylthiooctadecyl, 1-undecylthiooctadecyl, 1-decylthiooctadecyl, 1-nonylthiooctadecyl, 1-octylthiooctadecyl, 1-heptyloctadecyl, 1-hexylthiooctadecyl, 1-pentylthiooctadecyl, 1-butylthiooctadecyl, 1-propyloctadecyl, 1-ethylthiooctadecyl, 1-methylthiooctadecyl, 1-nonadecylthioeicosanyl, 1-octadecylthioeicosanyl, 1-heptadecylthioeicosanyl, 1-hexadecylthioeicosanyl, 1-pentadecylthioeicosanyl, 1-tetradecylthioeicosanyl, 1-tridecylthioeicosanyl, 1-dodecylthioeicosanyl, 1-undecylthioeicosanyl, 1-decylthioeicosanyl, 1-nonylthioeicosanyl, 1-octylthioeicosanyl, 1-heptyleicosanyl, 1-hexylthioeicosanyl, 1-pentylthioeicosanyl, 1-butylthioeicosanyl, 1-propyleicosanyl, 1-ethylthioeicosanyl, 1-methyleicosanyl, 1-eicosanylthiodocosanyl, 1-nonadecylthiodocosanyl, 1-octadecylthiodocosanyl, 1-heptadecylthiodocosanyl, 1-hexadecylthiodocosanyl, 1-pentadecylthiodocosanyl, 1-tetradecylthiodocosanyl, 1-tridecylthiodocosanyl, 1-undecylthiodocosanyl, 1-decylthiodocosanyl, 1-nonylthiodocosanyl, 1-octylthiodocosanyl, 1-heptyldocosanyl, 1-hexylthiodocosanyl, 1-pentylthiodocosanyl, 1-butylthiodocosanyl, 1-propyldocosanyl, 1-ethylthiodocosanyl, 1-methylthiodocosanyl, 1-tricosanylthiotetracosanyl, 1-docosanylthiotetracosanyl, 1-nonadecylthiotetracosanyl, 1-octadecylthiotetracosanyl, 1-heptadecylthiotetracosanyl, 1-hexadecylthiotetracosanyl, 1-pentadecylthiotetracosanyl, 1-pentadecylthiotetracosanyl, 1-tetradecylthiotetracosanyl, 1-tridecylthiotetracosanyl, 1-dodecylthiotetracosanyl, 1-undecylthiotetracosanyl, 1-decylthiotetracosanyl, 1-nonylthiotetracosanyl, 1-octylthiotetracosanyl, 1-heptylthiotetracosanyl, 1-hexylthiotetracosanyl, 1-pentylthiotetracosanyl, 1-butylthiotetracosanyl, 1-propyltetracosanyl, 1-ethylthiotetracosanyl, 1-methylthiotetracosanyl, 1-heptacosanylthiooctacosanyl, 1-hexacosanylthiooctacosanyl, 1-pentacosanylthiooctacosanyl, 1-tetracosanylthiooctacosanyl, 1-tricosanylthiooctacosanyl, 1-docosanylthiooctacosanyl, 1-nonadecylthiooctacosanyl, 1-octadecylthiooctacosanyl, 1-heptadecylthiooctacosanyl, 1-hexadecylthiooctacosanyl, 1-hexadecylthiooctacosanyl, 1-pentadecylthiooctacosanyl, 1-tetradecylthiooctacosanyl, 1-tridecylthiooctacosanyl, 1-dodecylthiooctacosanyl, 1-undecylthiooctacosanyl, 1-decylthiooctacosanyl, 1-nonylthiooctacosanyl, 1-octylthiooctacosanyl, 1-heptyloctacosanyl, 1-hexylthiooctacosanyl, 1-pentylthiooctacosanyl, 1-butylthiooctacosanyl, 1-propylthiooctacosanyl, 1-ethylthiooctacosanyl, 1-methylthiooctacosanyl;

in which q is 1, for example
2-ethylpropyl, 2-methylpropyl, 2-propylbutyl, 2-ethylbutyl, 2-methylbutyl, 2-butylpentyl, 2-propylpentyl, 2-ethylpentyl, 2-methylpentyl, 2-pentylhexyl, 2-butylhexyl, 2-propylhexyl, 2-ethylhexyl, 2-methylhexyl, 2-hexylheptyl, 2-pentylheptyl, 2-butylheptyl, 2-propylheptyl, 2-ethylheptyl, 2-methylheptyl, 2-heptyloctyl, 2-hexyloctyl, 2-pentyloctyl, 2-butyloctyl, 2-propyloctyl, 2-ethyloctyl, 2-methyloctyl, 2-octylnonyl, 2-heptylnonyl, 2-hexylnonyl, 2-pentylnonyl, 2-butylnonyl, 2-propylnonyl, 2-ethylnonyl, 2-methylnonyl, 2-nonyldecyl, 2-octyldecyl, 2-heptyldecyl, 2-hexyldecyl, 2-pentyldecyl, 2-butyldecyl, 2-propyldecyl, 2-ethyldecyl, 2-methyldecyl, 2-decylundecyl, 2-nonylundecyl, 2-octylundecyl, 2-heptylundecyl, 2-hexylundecyl, 2-pentylundecyl, 2-butylundecyl, 2-propylundecyl, 2-ethylundecyl, 2-methylundecyl, 2-undecyldodecyl, 2-decyldodecyl, 2-nonyldodecyl, 2-octyldodecyl, 2-heptyldodecyl, 2-hexyldodecyl, 2-pentyldodecyl, 2-butyldodecyl, 2-propyldodecyl, 2-ethyldodecyl, 2-methyldodecyl, 2-dodecyltridecyl, 2-undecyltridecyl, 2-decyltridecyl, 2-nonyltridecyl, 2-octyltridecyl, 2-heptyltridecyl, 2-hexyltridecyl, 2-pentyltridecyl, 2-butyltridecyl, 2-propyltridecyl, 2-ethyltridecyl, 2-methyltridecyl, 2-tridecyltetradecyl, 2-undecyltetradecyl, 2-decyltetradecyl, 2-nonyltetradecyl, 2-octyltetradecyl, 2-heptyltetradecyl, 2-hexyltetradecyl, 2-pentyltetradecyl, 2-butyltetradecyl, 2-propyltetradecyl, 2-ethyltetradecyl, 2-methyltetradecyl, 2-pentadecylhexadecyl, 2-tetradecylhexadecyl, 2-tridecylhexadecyl, 2-dodecylhexadecyl, 2-undecylhexadecyl, 2-decylhexadecyl, 2-nonylhexadecyl, 2-octylhexadecyl, 2-heptylhexadecyl, 2-hexylhexadecyl, 2-pentylhexadecyl, 2-butylhexadecyl, 2-propylhexadecyl, 2-ethylhexadecyl, 2-methylhexadecyl, 2-hexadecyloctadecyl, 2-pentadecyloctadecyl, 2-tetradecyloctadecyl, 2-tridecyloctadecyl, 2-dodecyloctadecyl, 2-undecyloctadecyl, 2-decyloctadecyl, 2-nonyloctadecyl, 2-octyloctadecyl, 2-heptyloctadecyl, 2-hexyloctadecyl, 2-pentyloctadecyl, 2-butyloctadecyl, 2-propyloctadecyl, 2-ethyloctadecyl, 2-methyloctadecyl, 2-nonadecyleicosanyl, 2-octadecyleicosanyl, 2-heptadecyleicosanyl, 2-hexadecyleicosanyl, 2-pentadecyleicosanyl, 2-tetradecyleicosanyl, 2-tridecyleicosanyl, 2-dodecyleicosanyl, 2-undecyleicosanyl, 2-decyleicosanyl, 2-nonyleicosanyl, 2-octyleicosanyl, 2-heptyleicosanyl, 2-hexyleicosanyl, 2-pentyleicosanyl, 2-butyleicosanyl, 2-propyleicosanyl, 2-ethyleicosanyl, 2-methyleicosanyl, 2-eicosanyldocosanyl, 2-nonadecyldocosanyl, 2-octadecyldocosanyl, 2-heptadecyldocosanyl, 2-hexadecyldocosanyl, 2-pentadecyldocosanyl, 2-tetradecyldocosanyl, 2-tridecyldocosanyl, 2-undecyldocosanyl, 2-decyldocosanyl, 2-nonyldocosanyl, 2-octyidocosanyl, 2-heptyldocosanyl, 2-hexyldocosanyl, 2-pentyldocosanyl, 2-butyldocosanyl, 2-propyldocosanyl, 2-ethyldocosanyl, 2-methyldocosanyl, 2-tricosanyltetracosanyl, 2-docosanyltetracosanyl, 2-nonadecyltetracosanyl, 2-octadecyltetracosanyl, 2-heptadecyltetracosanyl, 2-hexadecyltetracosanyl, 2-pentadecyltetracosanyl, 2-pentadecyltetracosanyl, 2-tetradecyltetracosanyl, 2-tridecyltetracosanyl, 2-dodecyltetracosanyl, 2-undecyltetracosanyl, 2-decyltetracosanyl, 2-nonyltetracosanyl, 2-octyltetracosanyl, 2-heptyltetracosanyl, 2-hexyltetracosanyl, 2-pentyltetracosanyl, 2-butyltetracosanyl, 2-propyltetracosanyl, 2-ethyltetracosanyl, 2-methyltetracosanyl, 2-heptacosanyloctacosanyl, 2-hexacosanyloctacosanyl, 2-pentacosanyloctacosanyl, 2-tetracosanyloctacosanyl, 2-tricosanyloctacosanyl, 2-docosanyloctacosanyl, 2-nonadecyloctacosanyl, 2-octadecyloctacosanyl, 2-heptadecyloctacosanyl, 2-hexadecyloctacosanyl, 2-hexadecyloctacosanyl, 2-pentadecyloctacosanyl, 2-tetradecyloctacosanyl, 2-tridecyloctacosanyl, 2-dodecyloctacosanyl, 2-undecyloctacosanyl, 2-decyloctacosanyl, 2-nonyloctacosanyl, 2-octyloctacosanyl, 2-heptyloctacosanyl, 2-hexyloctacosanyl, 2-pentyloctacosanyl, 2-butyloctacosanyl, 2-propyloctacosanyl, 2-ethyloctacosanyl, 2-methyloctacosanyl;

in which q is 2, for example
3-ethylpropyl, 3-methylpropyl, 3-propylbutyl, 3-ethylbutyl, 3-methylbutyl, 3-butylpentyl, 3-propylpentyl, 3-ethylpentyl, 3-methylpentyl, 3-pentylhexyl, 3-butylhexyl, 3-propylhexyl, 3-ethylhexyl, 3-methylhexyl, 3-hexylheptyl, 3-pentylheptyl, 3-butylheptyl, 3-propylheptyl, 3-ethylheptyl, 3-methylheptyl, 3-heptyloctyl, 3-hexyloctyl, 3-pentyloctyl, 3-butyloctyl, 3-propyloctyl, 3-ethyloctyl, 3-methyloctyl, 3-octylnonyl, 3-heptylnonyl, 3-hexylnonyl, 3-pentylnonyl, 3-butylnonyl, 3-propylnonyl, 3-ethylnonyl, 3-methylnonyl, 3-nonyidecyl, 3-octyldecyl, 3-heptyldecyl, 3-hexyldecyl, 3-pentyldecyl, 3-butyldecyl, 3-propyldecyl, 3-ethyldecyl, 3-methyldecyl, 3-decylundecyl, 3-nonylundecyl, 3-octylundecyl, 3-heptylundecyl, 3-hexylundecyl, 3-pentylundecyl, 3-butylundecyl, 3-propylundecyl, 3-ethylundecyl, 3-methylundecyl, 3-undecyldodecyl, 3-decyldodecyl, 3-nonyldodecyl, 3-octyldodecyl, 3-heptyldodecyl, 3-hexyldodecyl, 3-pentyldodecyl, 3-butyldodecyl, 3-propyldodecyl, 3-ethyldodecyl, 3-methyldodecyl, 3-dodecyltridecyl, 3-undecyltridecyl, 3-decyltridecyl, 3-nonyltridecyl, 3-octyltridecyl, 3-heptyltridecyl, 3-hexyltridecyl, 3-pentyltridecyl, 3-butyltridecyl, 3-propyltridecyl, 3-ethyltridecyl, 3-methyltridecyl, 3-tridecyltetradecyl, 3-undecyltetradecyl, 3-decyltetradecyl, 3-nonyltetradecyl, 3-octyltetradecyl, 3-heptyltetradecyl, 3-hexyltetradecyl, 3-pentyltetradecyl, 3-butyltetradecyl, 3-propyltetradecyl, 3-ethyltetradecyl, 3-methyltetradecyl, 3-pentadecylhexadecyl, 3-tetradecylhexadecyl, 3-tridecylhexadecyl, 3-dodecylhexadecyl, 3-undecylhexadecyl, 3-decylhexadecyl, 3-nonyihexadecyl, 3-octylhexadecyl, 3-heptylhexadecyl, 3-hexylhexadecyl, 3-pentylhexadecyl, 3-butylhexadecyl, 3-propylhexadecyl, 3-ethylhexadecyl, 3-methylhexadecyl, 3-hexadecyloctadecyl, 3-pentadecyloctadecyl, 3-tetradecyloctadecyl, 3-tridecyloctadecyl, 3-dodecyloctadecyl, 3-undecyloctadecyl, 3-decyloctadecyl, 3-nonyloctadecyl, 3-octyloctadecyl, 3-heptyloctadecyl, 3-hexyloctadecyl, 3-pentyloctadecyl, 3-butyloctadecyl, 3-propyloctadecyl, 3-ethyloctadecyl, 3-methyloctadecyl, 3-nonadecyleicosanyl, 3-octadecyleicosanyl, 3-heptadecyleicosanyl, 3-hexadecyleicosanyl, 3-pentadecyleicosanyl, 3-tetradecyleicosanyl, 3-tridecyleicosanyl, 3-dodecyleicosanyl, 3-undecyleicosanyl, 3-decyleicosanyl, 3-nonyleicosanyl, 3-octyleicosanyl, 3-heptyleicosanyl, 3-hexyleicosanyl, 3-pentyleicosanyl, 3-butyleicosanyl, 3-propyleicosanyl, 3-ethyleicosanyl, 3-methyleicosanyl, 3-eicosanyldocosanyl, 3-nonadecyldocosanyl, 3-octadecyldocosanyl, 3-heptadecyldocosanyl, 3-hexadecyldocosanyl, 3-pentadecyldocosanyl, 3-tetradecyldocosanyl, 3-tridecyldocosanyl, 3-undecyldocosanyl, 3-decyldocosanyl, 3-nonyldocosanyl, 3-octyldocosanyl, 3-heptyldocosanyl, 3-hexyldocosanyl, 3-pentyldocosanyl, 3-butyldocosanyl, 3-propyldocosanyl, 3-ethyldocosanyl, 3-methyldocosanyl, 3-tricosanyltetracosanyl, 3-docosanyltetracosanyl, 3-nonadecyltetracosanyl, 3-octadecyltetracosanyl, 3-heptadecyltetracosanyl, 3-hexadecyltetracosanyl, 3-pentadecyltetracosanyl, 3-pentadecyltetracosanyl, 3-tetradecyltetracosanyl, 3-tridecyltetracosanyl, 3-dodecyltetracosanyl, 3-undecyltetracosanyl, 3-decyltetracosanyl, 3-nonyltetracosanyl, 3-octyltetracosanyl, 3-heptyltetracosanyl, 3-hexyltetracosanyl, 3-pentyltetracosanyl, 3-butyltetracosanyl, 3-propyltetracosanyl, 3-ethyltetracosanyl, 3-methyltetracosanyl, 3-heptacosanyloctacosanyl, 3-hexacosanyloctacosanyl, 3-pentacosanyloctacosanyl, 3-tetracosanyloctacosanyl, 3-tricosanyloctacosanyl, 3-docosanyloctacosanyl, 3-nonadecyloctacosanyl, 3-octadecyloctacosanyl, 3-heptadecyloctacosanyl, 3-hexadecyloctacosanyl, 3-hexadecyloctacosanyl, 3-pentadecyloctacosanyl, 3-tetradecyloctacosanyl, 3-tridecyloctacosanyl, 3-dodecyloctacosanyl, 3-undecyloctacosanyl, 3-decyloctacosanyl, 3-nonyloctacosanyl, 3-octyloctacosanyl, 3-heptyloctacosanyl, 3-hexyloctacosanyl, 3-pentyloctacosanyl, 3-butyloctacosanyl, 3-propyloctacosanyl, 3-ethyloctacosanyl, 3-methyloctacosanyl, in which q is 3, such as
4-butylpentyl, 4-propylpentyl, 4-ethylpentyl, 4-methylpentyl, 4-pentylhexyl, 4-butylhexyl, 4-propylhexyl, 4-ethylhexyl, 4-methylhexyl, 4-hexylheptyl, 4-pentylheptyl, 4-butylheptyl, 4-propylheptyl, 4-ethylheptyl, 4-methylheptyl, 4-heptyloctyl, 4-hexyloctyl, 4-pentyloctyl, 4-butyloctyl, 4-propyloctyl, 4-ethyloctyl, 4-methyloctyl, 4-octylnonyl, 4-heptylnonyl, 4-hexylnonyl, 4-pentylnonyl, 4-butylnonyl, 4-propylnonyl, 4-ethylnonyl, 4-methylnonyl, 4-nonyldecyl, 4-octyldecyl, 4-heptyldecyl, 4-hexyldecyl, 4-pentyldecyl, 4-butyldecyl, 4-propyldecyl, 4-ethyldecyl, 4-methyldecyl, 4-decylundecyl, 4-nonylundecyl, 4-octylundecyl, 4-heptylundecyl, 4-hexylundecyl, 4-pentylundecyl, 4-butylundecyl, 4-propylundecyl, 4-ethylundecyl, 4-methylundecyl, 4-undecyldodecyl, 4-decyldodecyl, 4-nonyldodecyl, 4-octyldodecyl, 4-heptyldodecyl, 4-hexyldodecyl, 4-pentyldodecyl, 4-butyldodecyl, 4-propyldodecyl, 4-ethyldodecyl, 4-methyldodecyl, 4-dodecyltridecyl, 4-undecyltridecyl, 4-decyltridecyl, 4-nonyltridecyl, 4-octyltridecyl, 4-heptyltridecyl, 4-hexyltridecyl, 4-pentyltridecyl, 4-butyltridecyl, 4-propyltridecyl, 4-ethyltridecyl, 4-methyltridecyl, 4-tridecyltetradecyl, 4-undecyltetradecyl, 4-decyltetradecyl, 4-nonyltetradecyl, 4-octyltetradecyl, 4-heptyltetradecyl, 4-hexyltetradecyl, 4-pentyltetradecyl, 4-butyltetradecyl, 4-propyltetradecyl, 4-ethyltetradecyl, 4-methyltetradecyl, 4-pentadecylhexadecyl, 4-tetradecylhexadecyl, 4-tridecylhexadecyl, 4-dodecylhexadecyl, 4-undecylhexadecyl, 4-decylhexadecyl, 4-nonylhexadecyl, 4-octylhexadecyl, 4-heptylhexadecyl, 4-hexylhexadecyl, 4-pentylhexadecyl, 4-butylhexadecyl, 4-propylhexadecyl, 4-ethylhexadecyl, 4-methylhexadecyl, 4-hexadecyloctadecyl, 4-pentadecyloctadecyl, 4-tetradecyloctadecyl, 4-tridecyloctadecyl, 4-dodecyloctadecyl, 4-undecyloctadecyl, 4-decyloctadecyl, 4-nonyloctadecyl, 4-octyloctadecyl, 4-heptyloctadecyl, 4-hexyloctadecyl, 4-pentyloctadecyl, 4-butyloctadecyl, 4-propyloctadecyl, 4-ethyloctadecyl, 4-methyloctadecyl, 4-nonadecyleicosanyl, 4-octadecyleicosanyl, 4-heptadecyleicosanyl, 4-hexadecyleicosanyl, 4-pentadecyleicosanyl, 4-tetradecyleicosanyl, 4-tridecyleicosanyl, 4-dodecyleicosanyl, 4-undecyleicosanyl, 4-decyleicosanyl, 4-nonyleicosanyl, 4-octyleicosanyl, 4-heptyleicosanyl, 4-hexyleicosanyl, 4-pentyleicosanyl, 4-butyleicosanyl, 4-propyleicosanyl, 4-ethyleicosanyl, 4-methyleicosanyl, 4-eicosanyldocosanyl, 4-nonadecyldocosanyl, 4-octadecyldocosanyl, 4-heptadecyldocosanyl, 4-hexadecyldocosanyl, 4-pentadecyldocosanyl, 4-tetradecyldocosanyl, 4-tridecyldocosanyl, 4-undecyldocosanyl, 4-decyldocosanyl, 4-nonyldocosanyl, 4-octyldocosanyl, 4-heptyldocosanyl, 4-hexyldocosanyl, 4-pentyldocosanyl, 4-butyldocosanyl, 4-propyldocosanyl, 4-ethyldocosanyl, 4-methyldocosanyl, 4-tricosanyltetracosanyl, 4-docosanyltetracosanyl, 4-nonadecyltetracosanyl, 4-octadecyltetracosanyl, 4-heptadecyltetracosanyl, 4-hexadecyltetracosanyl, 4-pentadecyltetracosanyl, 4-pentadecyltetracosanyl, 4-tetradecyltetracosanyl, 4-tridecyltetracosanyl, 4-dodecyltetracosanyl, 4-undecyltetracosanyl, 4-decyltetracosanyl, 4-nonyltetracosanyl, 4-octyltetracosanyl, 4-heptyltetracosanyl, 4-hexyltetracosanyl, 4-pentyltetracosanyl, 4-butyltetracosanyl, 4-propyltetracosanyl, 4-ethyltetracosanyl, 4-methyltetracosanyl, 4-heptacosanyloctacosanyl, 4-hexacosanyloctacosanyl, 4-pentacosanyloctacosanyl, 4-tetracosanyloctacosanyl, 4-tricosanyloctacosanyl, 4-docosanyloctacosanyl, 4-nonadecyloctacosanyl, 4-octadecyloctacosanyl, 4-heptadecyloctacosanyl, 4-hexadecyloctacosanyl, 4-hexadecyloctacosanyl, 4-pentadecyloctacosanyl, 4-tetradecyloctacosanyl, 4-tridecyloctacosanyl, 4-dodecyloctacosanyl, 4-undecyloctacosanyl, 4-decyloctacosanyl, 4-nonyloctacosanyl, 4-octyloctacosanyl, 4-heptyloctacosanyl, 4-hexyloctacosanyl, 4-pentyloctacosanyl, 4-butyloctacosanyl, 4-propyloctacosanyl, 4-ethyloctacosanyl, 4-methyloctacosanyl, in which q is 4, such as
5-pentylhexyl, 5-butylhexyl, 5-propylhexyl, 5-ethylhexyl, 5-methylhexyl, 5-hexylheptyl, 5-pentylheptyl, 5-butylheptyl, 5-propylheptyl, 5-ethylheptyl, 5-methylheptyl, 5-heptyloctyl, 5-hexyloctyl, 5-pentyloctyl, 5-butyloctyl, 5-propyloctyl, 5-ethyloctyl, 5-methyloctyl, 5-octylnonyl, 5-heptylnonyl, 5-hexylnonyl, 5-pentylnonyl, 5-butylnonyl, 5-propylnonyl, 5-ethylnonyl, 5-methylnonyl, 5-nonyldecyl, 5-octyldecyl, 5-heptyidecyl, 5-hexyldecyl, 5-pentyldecyl, 5-butyldecyl, 5-propyldecyl, 5-ethyldecyl, 5-methyldecyl, 5-decylundecyl, 5-nonylundecyl, 5-octylundecyl, 5-heptylundecyl, 5-hexylundecyl, 5-pentylundecyl, 5-butylundecyl, 5-propylundecyl, 5-ethylundecyl, 5-methylundecyl, 5-undecyldodecyl, 5-decyldodecyl, 5-nonyldodecyl, 5-octyldodecyl, 5-heptyidodecyl, 5-hexyldodecyl, 5-pentyldodecyl, 5-butyldodecyl, 5-propyldodecyl, 5-ethyldodecyl, 5-methyldodecyl, 5-dodecyltridecyl, 5-undecyltridecyl, 5-decyltridecyl, 5-nonyltridecyl, 5-octyltridecyl, 5-heptyltridecyl, 5-hexyltridecyl, 5-pentyltridecyl, 5-butyltridecyl, 5-propyltridecyl, 5-ethyltridecyl, 5-methyltridecyl, 5-tridecyltetradecyl, 5-undecyltetradecyl, 5-decyltetradecyl, 5-nonyltetradecyl, 5-octyltetradecyl, 5-heptyltetradecyl, 5-hexyltetradecyl, 5-pentyltetradecyl, 5-butyltetradecyl, 5-propyltetradecyl, 5-ethyltetradecyl, 5-methyltetradecyl, 5-pentadecylhexadecyl, 5-tetradecylhexadecyl, 5-tridecylhexadecyl, 5-dodecylhexadecyl, 5-undecylhexadecyl, 5-decylhexadecyl, 5-nonylhexadecyl, 5-octylhexadecyl, 5-heptylhexadecyl, 5-hexylhexadecyl, 5-pentylhexadecyl, 5-butylhexadecyl, 5-propylhexadecyl, 5-ethylhexadecyl, 5-methylhexadecyl, 5-hexadecyloctadecyl, 5-pentadecyloctadecyl, 5-tetradecyloctadecyl, 5-tridecyloctadecyl, 5-dodecyloctadecyl, 5-undecyloctadecyl, 5-decyloctadecyl, 5-nonyloctadecyl, 5-octyloctadecyl, 5-heptyloctadecyl, 5-hexyloctadecyl, 5-pentyloctadecyl, 5-butyloctadecyl, 5-propyloctadecyl, 5-ethyloctadecyl, 5-methyloctadecyl, 5-nonadecyleicosanyl, 5-octadecyleicosanyl, 5-heptadecyleicosanyl, 5-hexadecyleicosanyl, 5-pentadecyleicosanyl, 5-tetradecyleicosanyl, 5-tridecyleicosanyl, 5-dodecyleicosanyl, 5-undecyleicosanyl, 5-decyleicosanyl, 5-nonyleicosanyl, 5-octyleicosanyl, 5-heptyleicosanyl, 5-hexyleicosanyl, 5-pentyleicosanyl, 5-butyleicosanyl, 5-propyleicosanyl, 5-ethyleicosanyl, 5-methyleicosanyl, 5-eicosanyldocosanyl, 5-nonadecyldocosanyl, 5-octadecyldocosanyl, 5-heptadecyldocosanyl, 5-hexadecyldocosanyl, 5-pentadecyldocosanyl, 5-tetradecyldocosanyl, 5-tridecyldocosanyl, 5-undecyldocosanyl, 5-decyldocosanyl, 5-nonyldocosanyl, 5-octyldocosanyl, 5-heptyldocosanyl, 5-hexyldocosanyl, 5-pentyldocosanyl, 5-butyldocosanyl, 5-propyldocosanyl, 5-ethyldocosanyl, 5-methyldocosanyl, 5-tricosanyltetracosanyl, 5-docosanyltetracosanyl, 5-nonadecyltetracosanyl, 5-octadecyltetracosanyl, 5-heptadecyltetracosanyl, 5-hexadecyltetracosanyl, 5-pentadecyltetracosanyl, 5-pentadecyltetracosanyl, 5-tetradecyltetracosanyl, 5-tridecyltetracosanyl, 5-dodecyltetracosanyl, 5-undecyltetracosanyl, 5-decyltetracosanyl, 5-nonyltetracosanyl, 5-octyltetracosanyl, 5-heptyltetracosanyl, 5-hexyltetracosanyl, 5-pentyltetracosanyl, 5-butyltetracosanyl, 5-propyltetracosanyl, 5-ethyltetracosanyl, 5-methyltetracosanyl, 5-heptacosanyloctacosanyl, 5-hexacosanyloctacosanyl, 5-pentacosanyloctacosanyl, 5-tetracosanyloctacosanyl, 5-tricosanyloctacosanyl, 5-docosanyloctacosanyl, 5-nonadecyloctacosanyl, 5-octadecyloctacosanyl, 5-heptadecyloctacosanyl, 5-hexadecyloctacosanyl, 5-hexadecyloctacosanyl, 5-pentadecyloctacosanyl, 5-tetradecyloctacosanyl, 5-tridecyloctacosanyl, 5-dodecyloctacosanyl, 5-undecyloctacosanyl, 5-decyloctacosanyl, 5-nonyloctacosanyl, 5-octyloctacosanyl, 5-heptyloctacosanyl, 5-hexyloctacosanyl, 5-pentyloctacosanyl, 5-butyloctacosanyl, 5-propyloctacosanyl, 5-ethyloctacosanyl, 5-methyloctacosanyl in which q is 5, for example 6-hexylheptyl, 6-pentylheptyl, 6-butylheptyl, 6-propylheptyl, 6-ethylheptyl, 6-methylheptyl, 6-heptyloctyl, 6-hexyloctyl, 6-pentyloctyl, 6-butyloctyl, 6-propyloctyl, 6-ethyloctyl, 6-methyloctyl, 6-octylnonyl, 6-heptylnonyl, 6-hexylnonyl, 6-pentylnonyl, 6-butylnonyl, 6-propylnonyl, 6-ethylnonyl, 6-methylnonyl, 6-nonyldecyl, 6-octyldecyl, 6-heptyldecyl, 6-hexyldecyl, 6-pentyldecyl, 6-butyldecyl, 6-propyldecyl, 6-ethyldecyl, 6-methyldecyl, 6-decylundecyl, 6-nonylundecyl, 6-octylundecyl, 6-heptylundecyl, 6-hexylundecyl, 6-pentylundecyl, 6-butylundecyl, 6-propylundecyl, 6-ethylundecyl, 6-methylundecyl, 6-undecyldodecyl, 6-decyldodecyl, 6-nonyldodecyl, 6-octyldodecyl, 6-heptyldodecyl, 6-hexyldodecyl, 6-pentyldodecyl, 6-butyldodecyl, 6-propyldodecyl, 6-ethyldodecyl, 6-methyldodecyl, 6-dodecyltridecyl, 6-undecyltridecyl, 6-decyltridecyl, 6-nonyltridecyl, 6-octyltridecyl, 6-heptyltridecyl, 6-hexyltridecyl, 6-pentyltridecyl, 6-butyltridecyl, 6-propyltridecyl, 6-ethyltridecyl, 6-methyltridecyl, 6-tridecyltetradecyl, 6-undecyltetradecyl, 6-decyltetradecyl, 6-nonyltetradecyl, 6-octyltetradecyl, 6-heptyltetradecyl, 6-hexyltetradecyl, 6-pentyltetradecyl, 6-butyltetradecyl, 6-propyltetradecyl, 6-ethyltetradecyl, 6-methyltetradecyl, 6-pentadecylhexadecyl, 6-tetradecylhexadecyl, 6-tridecylhexadecyl, 6-dodecylhexadecyl, 6-undecylhexadecyl, 6-decylhexadecyl, 6-nonylhexadecyl, 6-octylhexadecyl, 6-heptylhexadecyl, 6-hexylhexadecyl, 6-pentylhexadecyl, 6-butylhexadecyl, 6-propylhexadecyl, 6-ethylhexadecyl, 6-methylhexadecyl, 6-hexadecyloctadecyl, 6-pentadecyloctadecyl, 6-tetradecyloctadecyl, 6-tridecyloctadecyl, 6-dodecyloctadecyl, 6-undecyloctadecyl, 6-decyloctadecyl, 6-nonyloctadecyl, 6-octyloctadecyl, 6-heptyloctadecyl, 6-hexyloctadecyl, 6-pentyloctadecyl, 6-butyloctadecyl, 6-propyloctadecyl, 6-ethyloctadecyl, 6-methyloctadecyl, 6-nonadecyleicosanyl, 6-octadecyleicosanyl, 6-heptadecyleicosanyl, 6-hexadecyleicosanyl, 6-pentadecyleicosanyl, 6-tetradecyleicosanyl, 6-tridecyleicosanyl, 6-dodecyleicosanyl, 6-undecyleicosanyl, 6-decyleicosanyl, 6-nonyleicosanyl, 6-octyleicosanyl, 6-heptyleicosanyl, 6-hexyleicosanyl, 6-pentyleicosanyl, 6-butyleicosanyl, 6-propyleicosanyl, 6-ethyleicosanyl, 6-methyleicosanyl, 6-eicosanyldocosanyl, 6-nonadecyldocosanyl, 6-octadecyldocosanyl, 6-heptadecyldocosanyl, 6-hexadecyldocosanyl, 6-pentadecyldocosanyl, 6-tetradecyldocosanyl, 6-tridecyldocosanyl, 6-undecyldocosanyl, 6-decyldocosanyl, 6-nonyldocosanyl, 6-octyldocosanyl, 6-heptyldocosanyl, 6-hexyldocosanyl, 6-pentyldocosanyl, 6-butyldocosanyl, 6-propyldocosanyl, 6-ethyldocosanyl, 6-methyldocosanyl, 6-tricosanyltetracosanyl, 6-docosanyltetracosanyl, 6-nonadecyltetracosanyl, 6-octadecyltetracosanyl, 6-heptadecyltetracosanyl, 6-hexadecyltetracosanyl, 6-pentadecyltetracosanyl, 6-pentadecyltetracosanyl, 6-tetradecyltetracosanyl, 6-tridecyltetracosanyl, 6-dodecyltetracosanyl, 6-undecyltetracosanyl, 6-decyltetracosanyl, 6-nonyltetracosanyl, 6-octyltetracosanyl, 6-heptyltetracosanyl, 6-hexyltetracosanyl, 6-pentyltetracosanyl, 6-butyltetracosanyl, 6-propyltetracosanyl, 6-ethyltetracosanyl, 6-methyltetracosanyl, 6-heptacosanyloctacosanyl, 6-hexacosanyloctacosanyl, 6-pentacosanyloctacosanyl, 6-tetracosanyloctacosanyl, 6-tricosanyloctacosanyl, 6-docosanyloctacosanyl, 6-nonadecyloctacosanyl, 6-octadecyloctacosanyl, 6-heptadecyloctacosanyl, 6-hexadecyloctacosanyl, 6-hexadecyloctacosanyl, 6-pentadecyloctacosanyl, 6-tetradecyloctacosanyl, 6-tridecyloctacosanyl, 6-dodecyloctacosanyl, 6-undecyloctacosanyl, 6-decyloctacosanyl, 6-nonyloctacosanyl, 6-octyloctacosanyl, 6-heptyloctacosanyl, 6-hexyloctacosanyl, 6-pentyloctacosanyl, 6-butyloctacosanyl, 6-propyloctacosanyl, 6-ethyloctacosanyl, 6-methyloctacosanyl, in which q is 6, for example 7-heptyloctyl, 7-hexyloctyl, 7-pentyloctyl, 7-butyloctyl, 7-propyloctyl, 7-ethyloctyl, 7-methyloctyl, 7-octylnonyl, 7-heptylnonyl, 7-hexylnonyl, 7-pentylnonyl, 7-butylnonyl, 7-propylnonyl, 7-ethylnonyl, 7-methylnonyl, 7-nonyldecyl, 7-octyldecyl, 7-heptyldecyl, 7-hexyldecyl, 7-pentyldecyl, 7-butyldecyl, 7-propyldecyl, 7-ethyldecyl, 7-methyldecyl, 7-decylundecyl, 7-nonylundecyl, 7-octylundecyl, 7-heptylundecyl, 7-hexylundecyl, 7-pentylundecyl, 7-butylundecyl, 7-propylundecyl, 7-ethylundecyl, 7-methylundecyl, 7-undecyldodecyl, 7-decyldodecyl, 7-nonyldodecyl, 7-octyldodecyl, 7-heptyldodecyl, 7-hexyldodecyl, 7-pentyldodecyl, 7-butyldodecyl, 7-propyldodecyl, 7-ethyldodecyl, 7-methyldodecyl, 7-dodecyltridecyl, 7-undecyltridecyl, 7-decyltridecyl, 7-nonyltridecyl, 7-octyltridecyl, 7-heptyltridecyl, 7-hexyltridecyl, 7-pentyltridecyl, 7-butyltridecyl, 7-propyltridecyl, 7-ethyltridecyl, 7-methyltridecyl, 7-tridecyltetradecyl, 7-undecyltetradecyl, 7-decyltetradecyl, 7-nonyltetradecyl, 7-octyltetradecyl, 7-heptyltetradecyl, 7-hexyltetradecyl, 7-pentyltetradecyl, 7-butyltetradecyl, 7-propyltetradecyl, 7-ethyltetradecyl, 7-methyltetradecyl, 7-pentadecylhexadecyl, 7-tetradecylhexadecyl, 7-tridecylhexadecyl, 7-dodecylhexadecyl, 7-undecylhexadecyl, 7-decylhexadecyl, 7-nonylhexadecyl, 7-octylhexadecyl, 7-heptylhexadecyl, 7-hexylhexadecyl, 7-pentylhexadecyl, 7-butylhexadecyl, 7-propylhexadecyl, 7-ethylhexadecyl, 7-methylhexadecyl, 7-hexadecyloctadecyl, 7-pentadecyloctadecyl, 7-tetradecyloctadecyl, 7-tridecyloctadecyl, 7-dodecyloctadecyl, 7-undecyloctadecyl, 7-decyloctadecyl, 7-nonyloctadecyl, 7-octyloctadecyl, 7-heptyloctadecyl, 7-hexyloctadecyl, 7-pentyloctadecyl, 7-butyloctadecyl, 7-propyloctadecyl, 7-ethyloctadecyl, 7-methyloctadecyl, 7-nonadecyleicosanyl, 7-octadecyleicosanyl, 7-heptadecyleicosanyl, 7-hexadecyleicosanyl, 7-pentadecyleicosanyl, 7-tetradecyleicosanyl, 7-tridecyleicosanyl, 7-dodecyleicosanyl, 7-undecyleicosanyl, 7-decyleicosanyl, 7-nonyleicosanyl, 7-octyleicosanyl, 7-heptyleicosanyl, 7-hexyleicosanyl, 7-pentyleicosanyl, 7-butyleicosanyl, 7-propyleicosanyl, 7-ethyleicosanyl, 7-methyleicosanyl, 7-eicosanyldocosanyl, 7-nonadecyldocosanyl, 7-octadecyldocosanyl, 7-heptadecyldocosanyl, 7-hexadecyldocosanyl, 7-pentadecyldocosanyl, 7-tetradecyldocosanyl, 7-tridecyldocosanyl, 7-undecyldocosanyl, 7-decyldocosanyl, 7-nonyidocosanyl, 7-octyidocosanyl, 7-heptyldocosanyl, 7-hexyldocosanyl, 7-pentyldocosanyl, 7-butyldocosanyl, 7-propyldocosanyl, 7-ethyldocosanyl, 7-methyldocosanyl, 7-tricosanyltetracosanyl, 7-docosanyltetracosanyl, 7-nonadecyltetracosanyl, 7-octadecyltetracosanyl, 7-heptadecyltetracosanyl, 7-hexadecyltetracosanyl, 7-pentadecyltetracosanyl, 7-pentadecyltetracosanyl, 7-tetradecyltetracosanyl, 7-tridecyltetracosanyl, 7-dodecyltetracosanyl, 7-undecyltetracosanyl, 7-decyltetracosanyl, 7-nonyltetracosanyl, 7-octyltetracosanyl, 7-heptyltetracosanyl, 7-hexyltetracosanyl, 7-pentyltetracosanyl, 7-butyltetracosanyl, 7-propyltetracosanyl, 7-ethyltetracosanyl, 7-methyltetracosanyl, 7-heptacosanyloctacosanyl, 7-hexacosanyloctacosanyl, 7-pentacosanyloctacosanyl, 7-tetracosanyloctacosanyl, 7-tricosanyloctacosanyl, 7-docosanyloctacosanyl, 7-nonadecyloctacosanyl, 7-octadecyloctacosanyl, 7-heptadecyloctacosanyl, 7-hexadecyloctacosanyl, 7-hexadecyloctacosanyl, 7-pentadecyloctacosanyl, 7-tetradecyloctacosanyl, 7-tridecyloctacosanyl, 7-dodecyloctacosanyl, 7-undecyloctacosanyl, 7-decyloctacosanyl, 7-nonyloctacosanyl, 7-octyloctacosanyl, 7-heptyloctacosanyl, 7-hexyloctacosanyl, 7-pentyloctacosanyl, 7-butyloctacosanyl, 7-propyloctacosanyl, 7-ethyloctacosanyl, 7-methyloctacosanyl.

The inventive dibenzorylenetetracarboximides I may be unsubstituted or substituted, at the positions in the rylene skeleton specified in formula I, by R' radicals selected from aryloxy, arylthio, hetaryloxy or hetarylthio.

The dibenzopentarylenetetracarboxamides Ia may accordingly bear up to 4 substituents and the dibenzoquaterrylenetetracarboximides Ib up to 2 R' substituents in the rylene skeleton.

The use of one substituted and one unsubstituted peri-(dioxaborolan-2-yl)perylene-dicarboximide II in the Suzuki coupling also allows disubstituted dibenzopentarylenetetracarboximides to be prepared selectively.

Dibenzopentarylenetetracarboximides Ia with two different R' radical pairs are obtainable analogously by the use of two differently substituted peri-(dioxaboralan-2-yl)perylenedicarboximides II.

The preferred (het)aryloxy and -thio radicals R' are in particular phenoxy, thiophenoxy, 2-naphthoxy, 2-naphthylthio, 2-, 3- and 4-pyridyloxy, 2-, 3- and 4-pyridylthio, 2-, 4- and 5-pyrimidyloxy and 2-, 4- and 5-pyrimidylthio radicals, particular preference being given to the phenoxy and thiophenoxy radicals and very particular preference to the phenoxy radicals.

The (het)aryloxy and -thio radicals R' may themselves each be substituted by the radicals specified in claim 1, 2 and 3.

The particularly preferred (thio)phenoxy radicals R' may be mono-ortho-, -meta- or preferably -para-substituted. They may also be di-, tri-, tetra- or pentasubstituted, all conceivable substitution patterns being possible.

Particularly preferred R' radicals are (thio)phenoxy radicals which are substituted in the para position by a tert-alkyl radical such as tert-butyl or in particular a tert-alkyl radical of the formula

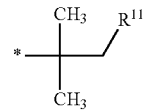

in which * is the bonding site to the benzene ring and $R^{ii}$ is defined as follows:

hydrogen;

$C_1$-$C_8$-alkyl whose carbon chain may be interrupted by one or more —O—, —S—, —NR$^1$—, —CO— and/or —SO$_2$— moieties and which may be mono- or polysubstituted by $C_1$-$C_6$-alkoxy and/or a 5- to 7-membered heterocyclic radical which is bonded via a nitrogen atom and may contain further heteroatoms and be aromatic;

$C_5$-$C_8$-cycloalkyl whose carbon skeleton may be interrupted by one or more —O—, —S—, —NR$^1$—, —CO— and/or —SO$_2$— moieties and which may be mono- or poly-$C_1$-$C_6$-alkyl-substituted, where $R^1$ is hydrogen or $C_1$-$C_6$-alkyl.

In a preferred embodiment, $R^{II}$ is hydrogen. In a further preferred embodiment, $R^{II}$ is $C_1$-$C_6$-alkyl which has 1 or 2 nonadjacent tertiary or quaternary carbon atoms. Particularly preferred R' radicals are then phenoxy radicals and thiophenoxy radicals which are para-substituted by

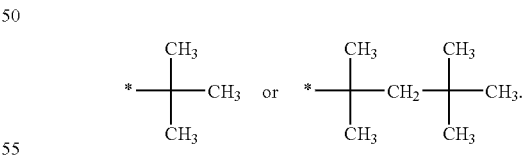

Specific examples of very particularly preferred para-substituted (thio)phenoxy radicals R' are:

4-(1,1-dimethylpropyl)phenoxy, 4-(1,1-dimethylbutyl)phenoxy, 4-(1,1-dimethylpentyl)-phenoxy, 4-(1,1,3,3-tetramethylbutyl)phenoxy, 4-(2-cyclopentyl-1,1-dimethylethyl)-phenoxy, 4-(2-cyclohexyl-1,1-dimethylethyl)phenoxy, 4-(2-cycloheptyl-1,1-dimethyl-ethyl)phenoxy and 4-[1,1-dimethyl-2-(4-morpholinyl)ethyl]phenoxy;

4-(1,1-dimethylpropyl)thiophenoxy, 4-(1,1-dimethylbutyl)thiophenoxy, 4-(1,1-dimethyl-pentyl)thiophenoxy, 4-(1,1,3,3-tetramethylbutyl)thiophenoxy, 4-(2-cyclopentyl-1,1-dimethylethyl)thiophenoxy, 4-(2-cyclohexyl-1,1-dimethylethyl) thiophenoxy, 4-(2-cyclo-heptyl-1,1-dimethylethyl) thiophenoxy and 4-[1,1-dimethyl-2-(4-morpholinyl)ethyl] thio-phenoxy.

Particularly preferred R' radicals are also ortho,ortho'-disubstituted (thio)phenoxy radicals of the formula

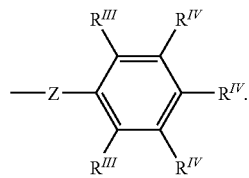

The $R^{III}$ radicals in the two ortho-positions may be the same or different, but they are preferably the same.

The (thio)phenoxy radicals R' may also be substituted in one, two or all three further ring positions by identical or nonidentical $R^{IV}$ radicals other than hydrogen.

The (thio)phenoxy radicals R' are preferably substituted only in the ortho- and ortho'-position or additionally in the para-position.

In particular, the variables in the abovementioned formula are each defined as follows:

Z is —O— or —S—, preferably —O—;
$R^{III}$ are identical or different radicals:
(i) $C_1$-$C_{18}$-alkyl whose carbon chain may be interrupted by one or more —O—, —S—, —$NR^1$— and/or —CO— moieties and which may be mono- or polysubstituted by $C_1$-$C_{12}$-alkoxy, hydroxyl and/or halogen, where at most one of the R''' radicals may have a tertiary carbon atom in the 1-position;
(ii) $C_3$-$C_8$-cycloalkyl which may be mono- or polysubstituted by $C_1$-$C_{18}$-alkyl and/or $C_1$-$C_{12}$-alkoxy, where at most one of the R''' radicals may have a tertiary carbon atom in the 1-position;
(iii) aryl or hetaryl, each of which may be mono- or polysubstituted by $C_1$-$C_{18}$-alkyl, $C_1$-$C_{12}$-alkoxy, hydroxyl and/or halogen;
(iv) a —U-aryl radical which may be mono- or polysubstituted by the above radicals specified as substituents for the aryl radicals (iii), where U is an —O—, —S— or —$NR^1$— moiety;
(v) $C_1$-$C_{12}$-alkoxy, hydroxyl, halogen or cyano;
$R^{IV}$ are identical or different radicals:
hydrogen;
one of the (i), (ii), (iii), (iv) and (v) radicals mentioned for R''', preferably $C_4$-$C_{18}$-alkyl radicals which may comprise a tertiary carbon atom in the 1-position;
$R^1$ is hydrogen or $C_1$-$C_6$-alkyl.

Preferred $R^{III}$ radicals are alkyl, cycloalkyl and phenyl radicals, in particular alkyl radicals having a secondary or primary carbon atom in the 1-position, and also methyl and cycloalkyl radicals having a secondary carbon atom in the 1-position, and particular emphasis should be given to the alkyl and cycloalkyl radicals having a secondary carbon atom in the 1-position.

Specific examples of these very particularly preferred (thio)phenoxy radicals R' include:

2,6-dimethylphenoxy, 2,6-diethylphenoxy, 2,6-diisopropylphenoxy, 2,6-di(2-butyl)-phenoxy, 2,6-di(n-butyl)phenoxy, 2,6-di(2-hexyl)phenoxy, 2,6-di(n-hexyl)phenoxy, 2,6-di(2-dodecyl)phenoxy, 2,6-di(n-dodecyl)phenoxy, 2,6-dicyclohexylphenoxy, 2,6-diphenylphenoxy, 2,6-di-methyl-4-(n-butyl)phenoxy, 2,6-diethyl-4-(n-butyl)phenoxy, 2,6-diisopropyl-4-(n-butyl)-phenoxy, 2,6-di(2-butyl)-4-(n-butyl) phenoxy, 2,4,6-tri(n-butyl)phenoxy, 2,6-di(2-hexyl)-4-(n-butyl)phenoxy, 2,6-di(n-hexyl)-4-(n-butyl)phenoxy, 2,6-di(2-dodecyl)-4-(n-butyl)phenoxy, 2,6-di(n-dodecyl)-4-(n-butyl)phenoxy, 2,6-dicyclohexyl-4-(n-butyl)phenoxy, 2,6-diphenyl-4-(n-butyl)phenoxy, 2,6-dimethyl-4-(n-nonyl) phenoxy, 2,6-diethyl-4-(n-nonyl)phenoxy, 2,6-diisopropyl-4-(n-nonyl)phenoxy, 2,6-di(2-butyl)-4-(n-nonyl)phenoxy, 2,6-di(2-butyl)-4-(n-nonyl)phenoxy, 2,6-di(2-hexyl)-4-(n-nonyl)phenoxy, 2,6-di(n-hexyl)-4-(n-nonyl)phenoxy, 2,6-di(2-dodecyl)-4-(n-nonyl)phenoxy, 2,6-di(n-dodecyl)-4-(n-nonyl)phenoxy, 2,6-dicyclohexyl-4-(n-nonyl)phenoxy, 2,6-diphenyl-4-(n-nonyl)phenoxy, 2,6-dimethyl-4-(n-octadecyl) phenoxy, 2,6-diethyl-4-(n-octadecyl)phenoxy, 2,6-diisopropyl-4-(n-octadecyl)phenoxy, 2,6-di(2-butyl)-4-(n-octadecyl)phenoxy, 2,6-di(2-butyl)-4-(n-octadecyl)phenoxy, 2,6-di(2-hexyl)-4-(n-octadecyl)phenoxy, 2,6-di(n-hexyl)-4-(n-octadecyl)phenoxy, 2,6-di(2-dodecyl)-4-(n-octadecyl) phenoxy, 2,6-di(n-dodecyl)-4-(n-octadecyl)phenoxy, 2,6-dicyclohexyl-4-(n-octadecyl)phenoxy, 2,6-dimethyl-4-(tert-butyl)phenoxy, 2,6-diethyl-4-(tert-butyl)phenoxy, 2,6-diisopropyl-4-(tert-butyl)phenoxy, 2,6-di(2-butyl)-4-(tert-butyl)phenoxy, 2,6-di-(n-butyl)-4-(tert-butyl)phenoxy, 2,6-di(2-hexyl)-4-(tert-butyl)phenoxy, 2,6-di(n-hexyl)-4-(tert-butyl)phenoxy, 2,6-di(2-dodecyl)-4-(tert-butyl)phenoxy, 2,6-di(n-dodecyl)-4-(tert-butyl)phenoxy, 2,6-dicyclohexyl-4-(tert-butyl)phenoxy, 2,6-diphenyl-4-(n-tert-butyl)phenoxy, 2,6-dimethyl-4-(tert-octyl)phenoxy, 2,6-diethyl-4-(tert-octyl)phenoxy, 2,6-diisopropyl-4-(tert-octyl)phenoxy, 2,6-di(2-butyl)-4-(tert-octyl)phenoxy, 2,6-di(n-butyl)-4-(tert-octyl)phenoxy, 2,6-di(2-hexyl)-4-(tert-octyl)phenoxy, 2,6-di(n-hexyl)-4-(tert-octyl)phenoxy, 2,6-di(2-dodecyl)-4-(tert-octyl)phenoxy, 2,6-di(n-dodecyl)-4-(tert-octyl)phenoxy, 2,6-dicyclohexyl-4-(tert-octyl)phenoxy and 2,6-diphenyl-4-(tert-octyl)phenoxy;

2,6-dimethylthiophenoxy, 2,6-diethylthiophenoxy, 2,6-diisopropylthiophenoxy, 2,6-di(2-butyl)thiophenoxy, 2,6-di(n-butyl)thiophenoxy, 2,6-di(2-hexyl)thiophenoxy, 2,6-di(n-hexyl)thiophenoxy, 2,6-di(2-dodecyl)thiophenoxy, 2,6-di(n-dodecyl)thiophenoxy, 2,6-dicyclohexylthiophenoxy, 2,6-diphenylthiophenoxy, 2,6-dimethyl-4-(n-butyl)thiophenoxy, 2,6-diethyl-4-(n-butyl)thiophenoxy, 2,6-diisopropyl-4-(n-butyl)thiophenoxy, 2,6-di(2-butyl)-4-(n-butyl)thiophenoxy, 2,4,6-tri(n-butyl)thiophenoxy, 2,6-di(2-hexyl)-4-(n-butyl) thiophenoxy, 2,6-di(n-hexyl)-4-(n-butyl)thiophenoxy, 2,6-di (2-dodecyl)-4-(n-butyl)thiophenoxy, 2,6-di(n-dodecyl)-4-(n-butyl)thiophenoxy, 2,6-dicyclohexyl-4-(n-butyl) thiophenoxy, 2,6-diphenyl-4-(n-butyl)thiophenoxy, 2,6-dimethyl-4-(n-nonyl)thiophenoxy, 2,6-diethyl-4-(n-nonyl) thiophenoxy, 2,6-diisopropyl-4-(n-nonyl)thiophenoxy, 2,6-di(2-butyl)-4-(n-nonyl)thiophenoxy, 2,6-di(2-butyl)-4-(n-nonyl)thiophenoxy, 2,6-di(2-hexyl)-4-(n-nonyl) thiophenoxy, 2,6-di(n-hexyl)-4-(n-nonyl)-thiophenoxy, 2,6-di(2-dodecyl)-4-(n-nonyl)thiophenoxy, 2,6-di(n-dodecyl)-4-(n-nonyl)-thiophenoxy, 2,6-dicyclohexyl-4-(n-nonyl) thiophenoxy, 2,6-diphenyl-4-(n-nonyl)thiophenoxy, 2,6-(dimethyl)-4-(n-octadecyl)thiophenoxy, 2,6-(diethyl)-4-(n-octadecyl)thiophenoxy, 2,6-diisopropyl-4-(n-octadecyl) thiophenoxy, 2,6-di(2-butyl)-4-(n-octadecyl)thiophenoxy, 2,6-di(2-butyl)-4-(n-octadecyl)thiophenoxy, 2,6-di(2-hexyl)-4-(n-octadecyl)thiophenoxy, 2,6-di(n-hexyl)-4-(n-octadecyl)thiophenoxy, 2,6-di(2-dodecyl)-4-(n-octadecyl) thiophenoxy, 2,6-di(n-dodecyl)-4-(n-octadecyl) thiophenoxy, 2,6-dicyclohexyl-4-(n-octadecyl)thiophenoxy, 2,6-dimethyl-4-(tert-butyl)thiophenoxy, 2,6-diethyl-4-(tert-butyl)thiophenoxy, 2,6-diisopropyl-4-(tert-butyl)thiophenoxy, 2,6-di(2-butyl)-4-(tert-butyl)thiophenoxy, 2,6-di-(n- butyl)-4-(tert-butyl)thiophenoxy, 2,6-di(2-hexyl)-4-(tert-butyl)thiophenoxy, 2,6-di(n-hexyl)-4-(tert-butyl)thiophenoxy, 2,6-di(2-dodecyl)-4-(tert-butyl)thiophenoxy, 2,6-di(n-dodecyl)-4-(tert-butyl)thiophenoxy, 2,6-dicyclohexyl-4-(tert-butyl)thiophenoxy, 2,6-diphenyl-4-(tert-butyl)thiophenoxy, 2,6-dimethyl-4-(tert-octyl)thiophenoxy, 2,6-diethyl-4-(tert-octyl)thiophenoxy, 2,6-diisopropyl-4-(tert-octyl)thiophenoxy, 2,6-di(2-butyl)-4-(tert-octyl)thiophenoxy, 2,6-di-(n-butyl)-4-(tert-octyl)thiophenoxy, 2,6-di(2-hexyl)-4-(tert-octyl)thiophenoxy, 2,6-di(n-hexyl)-4-(tert-octyl)thiophenoxy, 2,6-di(2-dodecyl)-4-(tert-octyl)thiophenoxy, 2,6-di(n-dodecyl)-4-(tert-octyl)thiophenoxy, 2,6-dicyclohexyl-4-(tert-octyl)thiophenoxy and 2,6-diphenyl-4-(tert-octyl)thiophenoxy.

Specific examples of the R, R', $R^{II}$, $R^{III}$, $R^{IV}$, $R^1$ to $R^4$ radicals mentioned in the formulae and their substituents include:

methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above terms isooctyl, isononyl, isodecyl and isotridecyl are trivial terms and stem from the alcohols obtained by the oxo process);

2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxamidecyl and 3,6,9,12-tetra-oxatetradecyl;

2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethyl-thiobutyl, 2- and 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiamidecyl and 3,6,9,12-tetrathiatetradecyl;

2-monomethyl- and 2-monoethylaminoethyl, 2-dimethylaminoethyl, 2- and 3-dimethyl-aminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazamidecyl and 3,6,9,12-tetramethyl-3,6,9,12-tetraazamidecyl;

(1-ethylethylidene)aminoethylene, (1-ethylethylidene)aminopropylene, (1-ethylethylidene)aminobutylene, (1-ethylethylidene)aminodecylene and (1-ethylethylidene)aminododecylene;

propan-2-on-1-yl, butan-3-on-1-yl, butan-3-on-2-yl and 2-ethylpentan-3-on-1-yl;

2-methylsulfoxidoethyl, 2-ethylsulfoxidoethyl, 2-propylsulfoxidoethyl, 2-isopropylsulfoxidoethyl, 2-butylsulfoxidoethyl, 2- and 3-methylsulfoxidopropyl, 2- and 3-ethylsulfoxidopropyl, 2- and 3-propylsulfoxidopropyl, 2- and 3-butylsulfoxidopropyl, 2- and 4-methylsulfoxidobutyl, 2- and 4-ethylsulfoxidobutyl, 2- and 4-propylsulfoxidobutyl and 4-butylsulfoxidobutyl;

2-methylsulfonylethyl, 2-ethylsulfonylethyl, 2-propylsulfonylethyl, 2-isopropylsulfonyl-ethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonyl-butyl, 2- and 4-ethylsulfonylbutyl, 2- and 4-propylsulfonylbutyl and 4-butylsulfonylbutyl; carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxy-tetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

2-hydroxyethyl, 2- and 3-hydroxypropyl, 1-hydroxyprop-2-yl, 3- and 4-hydroxybutyl, 1-hydroxybut-2-yl and 8-hydroxy-4-oxaoctyl;

2-cyanoethyl, 3-cyanopropyl, 3- and 4-cyanobutyl, 2-methyl-3-ethyl-3-cyanopropyl, 7-cyano-7-ethylheptyl and 4,7-dimethyl-7-cyanoheptyl;

2-chloroethyl, 2- and 3-chloropropyl, 2-, 3- and 4-chlorobutyl, 2-bromoethyl, 2- and 3-bromopropyl and 2-, 3- and 4-bromobutyl;

2-nitroethyl, 2- and 3-nitropropyl and 2-, 3- and 4-nitrobutyl;
methoxy, ethoxy, propoxy, isopropoxy, butoxy, isobutoxy, sec-butoxy, tert-butoxy, pentoxy, isopentoxy, neopentoxy, tert-pentoxy and hexoxy;

methylthio, ethylthio, propylthio, isopropylthio, butylthio, isobutylthio, sec-butylthio, tert-butylthio, pentylthio, isopentylthio, neopentylthio, tert-pentylthio and hexylthio;

ethynyl, 1- and 2-propynyl, 1-, 2- and 3-butynyl, 1-, 2-, 3- and 4-pentynyl, 1-, 2-, 3-, 4- and 5-hexynyl, 1-, 2-, 3-, 4-, 5-, 6-, 7-, 8- and 9-decynyl, 1-, 2-, 3-, 4-, 5-, 6-, 7-, 8-, 9-, 10- and 1'-dodecynyl and 1-, 2-, 3-, 4-, 5-, 6-, 7-, 8-, 9-, 10-, 11-, 12-, 13-, 14-, 15-, 16- and 17-octadecynyl;

ethenyl, 1- and 2-propenyl, 1-, 2- and 3-butenyl, 1-, 2-, 3- and 4-pentenyl, 1-, 2-, 3-, 4- and 5-hexenyl, 1-, 2-, 3-, 4-, 5-, 6-, 7-, 8- and 9-decenyl, 1-, 2-, 3-, 4-, 5-, 6-, 7-, 8-, 9-, 10- and 11-dodecenyl and 1-, 2-, 3-, 4-, 5-, 6-, 7-, 8-, 9-, 10-, 11-, 12-, 13-, 14-, 15-, 16- and 17-octadecenyl;

methylamino, ethylamino, propylamino, isopropylamino, butylamino, isobutylamino, pentylamino, hexylamino, dimethylamino, methylethylamino, diethylamino, dipropylamino, diisopropylamino, dibutylamino, diisobutylamino, dipentylamino, dihexylamino, dicyclopentylamino, dicyclohexylamino, dicycloheptylamino, diphenylamino and dibenzylamino;

formylamino, acetylamino, propionylamino and benzoylamino;

carbamoyl, methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, decylaminocarbonyl and phenylaminocarbonyl;

aminosulfonyl, N,N-dimethylaminosulfonyl, N,N-diethylaminosulfonyl, N-methyl-N-ethylaminosulfonyl, N-methyl-N-dodecylaminosulfonyl, N-dodecylaminosulfonyl, (N,N-dimethylamino)ethylaminosulfonyl, N,N-(propoxyethyl)dodecylaminosulfonyl, N,N-diphenylaminosulfonyl, N,N-(4-tert-butylphenyl)octadecylaminosulfonyl and N,N-bis(4-chlorophenyl)aminosulfonyl;

methoxycarbonyl, ethoxycarbonyl, propoxycarbonyl, isopropoxycarbonyl, hexoxycarbonyl, dodecyloxycarbonyl, octadecyloxycarbonyl, phenoxycarbonyl, (4-tert-butyl-phenoxy)carbonyl and (4-chlorophenoxy)carbonyl;

methoxysulfonyl, ethoxysulfonyl, propoxysulfonyl, isopropoxysulfonyl, butoxysulfonyl, isobutoxysulfonyl, tert-butoxysulfonyl, hexoxysulfonyl, dodecyloxysulfonyl, octadecyloxysulfonyl, phenoxysulfonyl, 1- and 2-naphthyloxysulfonyl, (4-tert-butylphenoxy)sulfonyl and (4-chlorophenoxy)sulfonyl;

chlorine, bromine and iodine;

phenylazo, 2-naphthylazo, 2-pyridylazo and 2-pyrimidylazo;

cyclopropyl, cyclobutyl, cyclopentyl, 2- and 3-methylcyclopentyl, 2- and 3-ethylcyclo-pentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methyl-cycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl and 3-, 4- and 5-propylcyclooctyl; 3- and 4-hydroxycyclohexyl, 3- and 4-nitrocyclohexyl and 3- and 4-chlorocyclohexyl;

1-, 2- and 3-cyclopentenyl, 1-, 2-, 3- and 4-cyclohexenyl, 1-, 2- and 3-cycloheptenyl and 1-, 2-, 3- and 4-cyclooctenyl;

2-dioxanyl, 1-morpholinyl, 1-thiomorpholinyl, 2- and 3-tetrahydrofuryl, 1-, 2- and 3-pyrrolidinyl, 1-piperazyl, 1-diketopiperazyl and 1-, 2-, 3- and 4-piperidyl;

phenyl, 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 5-isoquinolyl;

1-, 2-, 3-, 4-, 5-, 6- and 7-indolyl, 1-, 2-, 3-, 4-, 5-, 6- and 7-isoindolyl, 5-(4-methylisoindolyl), 5-(4-phenylisoindolyl), 1-, 2-, 4-, 6-, 7- and 8-(1,2,3,4-tetrahydroisoquinolinyl), 3-(5-phenyl)-(1,2,3,4-tetrahydroisoquinolinyl), 5-(3-dodecyl-(1,2,3,4-tetrahydro-isoquinolinyl), 1-, 2-, 3-, 4-, 5-, 6-, 7- and 8-(1,2,3,4-tetrahydroquinolinyl) and 2-, 3-, 4-, 5-, 6-, 7- and 8-chromanyl, 2-, 4- and 7-quinolinyl, 2-(4-phenylquinolinyl) and 2-(5-ethylquinolinyl);

2-, 3- and 4-methylphenyl, 2,4-, 3,5- and 2,6-dimethylphenyl, 2,4,6-trimethylphenyl, 2-, 3- and 4-ethylphenyl, 2,4-, 3,5- and 2,6-diethylphenyl, 2,4,6-triethylphenyl, 2-, 3- and 4-propylphenyl, 2,4-, 3,5- and 2,6-dipropylphenyl, 2,4,6-tripropylphenyl, 2-, 3- and 4-isopropylphenyl, 2,4-, 3,5- and 2,6-diisopropylphenyl, 2,4,6-triisopropylphenyl, 2-, 3- and 4-butylphenyl, 2,4-, 3,5- and 2,6-dibutylphenyl, 2,4,6-tributylphenyl, 2-, 3- and 4-isobutylphenyl, 2,4-, 3,5- and 2,6-diisobutylphenyl, 2,4,6-triisobutylphenyl, 2-, 3- and 4-sec-butylphenyl, 2,4-, 3,5- and 2,6-di-sec-butylphenyl and 2,4,6-tri-sec-butylphenyl; 2-, 3- and 4-methoxyphenyl, 2,4-, 3,5- and 2,6-dimethoxyphenyl, 2,4,6-trimethoxyphenyl, 2-, 3- and 4-ethoxyphenyl, 2,4-, 3,5- and 2,6-diethoxyphenyl, 2,4,6-triethoxyphenyl, 2-, 3- and 4-propoxyphenyl, 2,4-, 3,5- and 2,6-dipropoxyphenyl, 2-, 3- and 4-isopropoxyphenyl, 2,4- and 2,6-diisopropoxyphenyl and 2-, 3- and 4-butoxyphenyl;

2-, 3- and 4-chlorophenyl and 2,4-, 3,5- and 2,6-dichlorophenyl; 2-, 3- and 4-hydroxyphenyl and 2,4-, 3,5- and 2,6-dihydroxyphenyl; 2-, 3- and 4-cyanophenyl; 3- and 4-carboxyphenyl; 3- and 4-carboxamidophenyl, 3- and 4-N-methylcarboxamidophenyl and 3- and 4-N-ethylcarboxamidophenyl; 3- and 4-acetylaminophenyl, 3- and 4-propionylaminophenyl and 3- and 4-butyrylaminophenyl; 3- and 4-N-phenylaminophenyl, 3- and 4-N-(o-tolyl)aminophenyl, 3- and 4-N-(m-tolyl)aminophenyl and 3- and 4-(p-tolyl)aminophenyl; 3- and 4-(2-pyridyl)aminophenyl, 3- and 4-(3-pyridyl)aminophenyl, 3- and 4-(4-pyridyl)aminophenyl, 3- and 4-(2-pyrimidyl)aminophenyl and 4-(4-pyrimidyl)aminophenyl;

4-phenylazophenyl, 4-(1-naphthylazo)phenyl, 4-(2-naphthylazo)phenyl, 4-(4-naphthyl-azo)phenyl, 4-(2-pyridylazo)phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl; phenoxy, phenylthio, 2-naphthoxy, 2-naphthylthio, 2-, 3- and 4-pyridyloxy, 2-, 3- and 4-pyridylthio, 2-, 4- and 5-pyrimidyloxy and 2-, 4- and 5-pyrimidylthio.

The dibenzorylenetetracarboximides I can advantageously be prepared by the process according to the invention by Suzuki coupling of the corresponding peri-(dioxaborolan-2-yl)rylenedicarboximides II

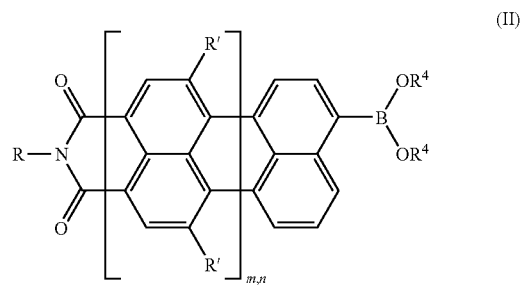

(II)

with 5,11-dibromotetracene (III) (step a)), first cyclodehydrogenation of the tetracene-5,11-bis(rylenedicarboximide) IV formed (step b)) and further cyclodehydrogenation of the bisrylene derivative V formed (step c)).

The preparation of the dibenzorylenetetracarboximides Ib with asymmetrical ring skeleton differs from the preparation of the symmetric benzorylenetetracarboximides Ia merely in that the Suzuki coupling in step a) is effected in two stages by successive reaction of 5,11-dibromotetracene III with the two peri-(dioxaborolan-2-yl)rylenedi-carboximides IIb1 and IIb2.

The two-stage process variant in step a) should of course also be employed analogously for dibenzorylenetetracarboximides Ia with symmetric ring skeleton which comprise different R and/or R' radicals.

The Suzuki coupling in step a) is performed in the presence of an organic solvent, if desired in a mixture with water, and of a transition metal catalyst and of a base.

The peri-(dioxaborolan-2-yl)rylenedicarboximides II used here as the rylene reactant are, like 5,11-dibromotetracene (III), known and are described, for example, in WO-A-05/70894 and the prior German patent application 102005018241.0.

The molar ratio of II to III is generally from 1.7:1 to 2.3:1, preferably from 1.9:1 to 2.1:1. When two different dioxaborolanylrylene derivatives II are used, the molar ratio of II to III is in each case typically from 0.7:1 to 1.3:1, preferably from 0.9:1 to 1.1:1.

Suitable solvents for step a) are all solvents in which the dioxaborolanylrylene derivatives II and dibromotetracene III dissolve fully at reaction temperature and the catalysts and bases used at least partially, so that largely homogeneous reaction conditions are present. It is possible to use either nonpolar aprotic or polar aprotic solvents, preference being given to the nonpolar aprotic solvents.

Examples of preferred nonpolar aprotic solvents are solvents having a boiling point of >100° C. from the following groups: aliphatics (especially $C_8$-$C_{18}$-alkanes), unsubstituted, alkyl-substituted and fused cycloaliphatics (especially unsubstituted $C_7$-$C_{10}$-cycloalkanes, $C_6$-$C_8$-cycloalkanes which are substituted by from one to three $C_1$-$C_6$-alkyl groups, polycyclic saturated hydrocarbons having form 10 to 18 carbon atoms), alkyl- and cycloalkyl-substituted aromatics (especially benzene which is substituted by from one to three $C_1$-$C_6$-alkyl groups or one $C_5$-$C_8$-cycloalkyl radical) and fused aromatics which may be alkyl-substituted and/or part-hydrogenated (especially naphthalene which is substituted by from one to four $C_1$-$C_6$-alkyl groups), and also mixtures of these solvents.

Specific examples of particularly preferred solvents include: octane, isooctane, nonane, isononane, decane, isodecane, undecane, dodecane, hexadecane and octadecane; cycloheptane, cyclooctane, methylcyclohexane, dimethylcyclohexane, trimethylcyclo-hexane, ethylcyclohexane, diethylcyclohexane, propylcyclohexane, isopropylcyclo-hexane, dipropylcyclohexane, butylcyclohexane, tert-butylcyclohexane, methylcyclo-heptane and methylcyclooctane; toluene, o-, m- and p-xylene, 1,3,5-trimethylbenzene (mesitylene), 1,2,4- and 1,2,3-trimethylbenzene, ethylbenzene, propylbenzene, isopropylbenzene, butylbenzene, isobutylbenzene, tert-butylbenzene and cyclohexylbenzene; naphthalene, decahydronaphthalene (decalin), 1- and 2-methyl-naphthalene and 1- and 2-ethylnaphthalene; combinations of the aforementioned solvents, as can be obtained from the high-boiling, partly or fully hydrogenated fractions of thermal and catalytic cracking processes in crude oil or naphtha processing, for example mixtures of the Exxsol® type and alkylbenzene mixtures of the Solvesso® type.

Very particularly preferred solvents are xylene (all isomers), mesitylene and in particular toluene.

Examples of suitable polar aprotic solvents are N,N-disubstituted aliphatic carboxamides (especially N,N-di-$C_1$-$C_4$-alkyl-$C_1$-$C_4$-carboxamides), nitrogen heterocycles and aprotic ethers (especially cyclic ethers and di-$C_1$-$C_5$-alkyl ethers of monomeric and oligomeric $C_2$-$C_3$-alkylene glycols which may comprise up to 6 alkylene oxide units, in particular diethylene glycol di-$C_1$-$C_4$-alkyl ethers).

Specific examples of particularly suitable solvents from this group include: N,N-dimethylformamide, N,N-diethylformamide, N,N-dimethylacetamide and N,N-dimethylbutyramide; N-methyl-2-pyrrolidone, quinoline, isoquinoline, quinaldine, pyrimidine, N-methylpiperidine and pyridine; tetrahydrofuran, dioxane, diethylene glycol dimethyl ether and diethylene glycol diethyl ether.

The amount of solvent is typically from 10 to 1000 ml, preferably from 50 to 500 ml and more preferably from 75 to 250 ml per g of II.

Preference is given to using water, if appropriate together with a protic organic solvent, especially an aliphatic alcohol, especially a $C_1$-$C_5$-alcohol such as ethanol, as an additional solvent. In this case, generally from 10 to 1000 ml, especially from 15 to 500 ml and in particular from 20 to 250 ml of water and, if appropriate, protic organic solvent are used per I of aprotic (preferably nonpolar aprotic) solvent.

Suitable transition metal catalysts are in particular palladium complexes, such as tetrakis(triphenylphosphine)palladium(0), tetrakis(tris-o-tolylphosphine)palladium(0), [1,2-bis(diphenylphosphino)ethane]palladium(II) chloride, [1,1'-bis(diphenyl-phosphino)ferrocene]palladium(II) chloride, bis(triethylphosphine)palladium(II) chloride, bis(tricyclohexylphosphine)palladium(II) acetate, (2,2'-bipyridyl)palladium(II) chloride, bis(triphenylphosphine)palladium(II) chloride, tris(dibenzylideneacetone)-dipalladium(0), 1,5-cyclooctadienepalladium(II) chloride, bis(acetonitrile)palladium(II) chloride and bis(benzonitrile)palladium(II) chloride, preference being given to tris(dibenzylideneacetone) dipalladium(0), [1,1'-bis(diphenylphosphino)ferrocene]-palladium(II) chloride and tetrakis(triphenylphosphine) palladium(0).

Typically, the transition metal catalyst is used in an amount of from 1 to 20 mol %, in particular from 1.5 to 5 mol %, based on II.

The simultaneous presence of free ligand molecules, for example of tri(tert-butyl)phosphine, triphenylphosphine, tris (o-tolyl)phosphine, 1,1'-(2,2'-diphenylphosphino)binaphthalene or in particular bis(2-diphenylphosphino)phenyl ether, may be advantageous in some cases. Suitable amounts are from 80 to 500 mol %, preferably from 100 to 300 mol %, based on the transition metal catalyst.

The bases used are preferably the alkali metal salts, preferably the sodium salts and in particular the potassium salts, of weak organic and in particular weak inorganic acids, such as formates, acetates, propionates, hydrogencarbonates and preferably carbonates, such as sodium acetate, potassium acetate, sodium hydrogencarbonate, sodium carbonate, potassium hydrogencarbonate and potassium carbonate. Particular preferred bases are the carbonates, very particular preference being given to sodium carbonate and in particular to potassium carbonate.

In general, the amount of bases is from 1 to 100 mol, especially from 5 to 50 mol and in particular from 10 to 30 mol per mole of II.

When a two-stage coupling with two different dioxaborolanylrylene derivatives II is performed, it is advisable to isolate the product of the first coupling step together with the transition metal catalyst and to add the base gradually.

The reaction temperature is generally from 20 to 180° C., preferably from 40 to 150° C. and more preferably from 60 to 120° C. When water is used in step a), it is advisable not to undertake the reaction at temperatures above 100° C., since it would otherwise be necessary to work under pressure.

It is advisable to work under protective gas.

The reaction has ended typically within from 0.5 to 48 h, especially within from 3 to 24 h and in particular within from 5 to 20 h.

In terms of process technology, the procedure in step a) is appropriately as follows: dioxaborolanylrylene derivative II and dibromotetracene III and solvent are initially charged, transition metal catalyst and the base, preferably dissolved in water, are added, and the mixture is heated to the desired reaction temperature under protective gas for from 0.5 to 48 h. After cooling to room temperature, the organic phase is removed from the reaction mixture and the solvent is distilled off under reduced pressure.

The purity of the tetracene-5,11-bis(rylenedicarboximide) IV thus prepared is generally sufficient for further processing. If appropriate, the crude product may be purified further by washing with water and, if desired, a suitable organic solvent, especially a chlorinated aliphatic or aromatic hydrocarbon, or by column chromatography on silica gel with dichloromethane as the eluent.

Step b) of the preparation process according to the invention, the cyclo-dehydrogenation of the tetracene-5,11-bis (rylenedicarboximide) IV to the bisrylene derivative V, is undertaken under anhydrous conditions in the presence of an inert organic solvent and of a Lewis acid.

Suitable solvents are in principle all organic solvents which are inert under the reaction conditions, polar aprotic solvents being particularly suitable.

Preferred solvents are halogenated and nitrated aliphatic or aromatic hydrocarbons. In addition to the aromatic hydrocarbons such as chlorobenzene, di- and trichlorobenzene and nitrobenzene, in particular the corresponding aliphatic hydrocarbons, in particular the methanes and ethanes, should be emphasized. Specific examples of the particularly preferred solvents include: dichloro-, trichloro-, tribromo-, tetrachloro- and tetrabromomethane, nitromethane, 1,2-dichloro-, 1,1-dibromo- and 1,2-dibromoethane, 1,1,1-trichloro-, 1,1,2-trichloro-, 1,1,1-tribromo- and 1,1,2-tribromoethane and 1,1,1,2-tetrachloro-, 1,1,2,2-tetrachloro-, 1,1,1,2-tetrabromo- and 1,1,2,2-tetrabromoethane, very particular preference being given to dichloromethane (methylene chloride), trichloromethane (chloroform) and nitromethane.

The amount of solvent is generally from 10 to 100 ml, in particular from 20 to 40 ml per g of IV.

Suitable Lewis acids are in particular iron(III) halides such as iron(III) chloride and iron(III) bromide, and aluminum trihalides such as aluminum trichloride.

Typically, from 2 to 10 mol, preferably from 6 to 8 mol, of Lewis acid are used per mole of IV.

The cyclodehydrogenation in step b) is generally performed at temperatures around room temperature, i.e. heating of the reaction mixture is generally not required.

It is appropriate to perform the reaction with exclusion of light.

The reaction times are typically from about 0.5 to 5 h, in particular from 1 to 2 h.

In terms of process technology, the procedure in step b) is appropriately as follows:

tetracene derivative IV and solvent are initially charged, the Lewis acid, preferably dissolved in further solvent, is added, and the mixture is stirred and light exclusion at room temperature for from 1 to 10 h. Subsequently, the reaction mixture is added to a lower aliphatic alcohol such as methanol, and the precipitated product is isolated by filtering and drying.

The purity of the bisrylene derivative V thus prepared is generally sufficient for the second cyclodehydrogenation step c). If appropriate, the crude product can be purified further by column chromatography on silica gel with dichloromethane as the eluent.

The second cyclodehydrogenation to give the dibenzoryle-netetracarboximide I is performed in an organic reaction medium which has hydroxyl and amino functions and comprises an essentially undissolved base.

Suitable organic reaction media are in particular amino alcohols which have from 2 to 20, preferably from 2 to 10 carbon atoms. The carbon chain of these alcohols may be interrupted by oxygen atoms in ether function. Examples of particularly suitable solvents are ethanolamine, triethanolamine and diethanolamine, preference being given to ethanolamine. It is also possible to use mixtures of alcohols and amines, each of which have a boiling point of at least 70° C. and are liquid at the reaction temperature.

Typically from 1.5 to 150 ml, preferably from 5 to 50 ml of reaction medium are used per g of bisrylene derivative V.

In order to convert the bisrylene derivative V into solution, it may be appropriate to add small amounts of a polar aprotic solvent, especially of an N,N-disubstituted aliphatic carboxamide such as dimethylformamide.

Suitable amounts of this additional solvent are appropriately from about 1 to 10 ml, in particular from 3 to 5 ml of solvent per g of bisrylene derivative V. Suitable bases essentially undissolved in the reaction medium are the alkali metal bases used in step a), preference being given here too to the alkali metal carbonates, especially sodium carbonate and in particular potassium carbonate.

In general, the amount of bases is from 1 to 10 mol, preferably from 2 to 5 mol per mole of bisrylene derivative V.

The reaction temperature is generally from 40 to 200° C., in particular from 80 to 160° C.

The reaction has ended typically within from 0.5 to 24 h, preferably within from 1 to 12 h.

In process technology terms, the procedure in step c) is appropriately as follows:

a mixture of bisrylene derivative V, solvent and base is stirred at the desired reaction temperature for from 0.5 to 24 h and the product, after cooling to room temperature, is precipitated out of the reaction mixture by adding water or an alcohol such as ethanol, filtered off and washed with water, alcohols such as methanol, and/or dichloromethane.

The resulting dibenzorylenetetracarboximides I can be purified as follows:

catalyst residues can be removed by rapid filtration through silica gel with washing with a halogenated aliphatic hydrocarbon such as dichloromethane. Residues of unconverted perylene- or naphthalene-based reactants can be removed by column chromatography on silica gel with dichloromethane or mixtures of dichloromethane and nonpolar solvents such as petroleum ether as the eluent, or by extraction with chlorobenzene.

The inventive dibenzorylenetetracarboximides I exhibit strong absorption in the near infrared region at wavelengths of from 800 to 1100 nm and hence complement the spectral region accessible with the aid of the rylene compounds known to date in an advantageous manner. The absorption maximum of the different dibenzorylenetetracarboximides I is approximately within the following ranges: dibenzopentarylene derivatives Ia: 1000 to 1100 nm; dibenzoquaterrylene derivatives Ib: 900 to 950 nm; dibenzoterrylene derivatives Ia: 800 to 850 nm. The dibenzorylenetetracarboximides I can therefore be used particularly advantageously in combination with the commercial lasers which emit at from 940 to 980 and 1064 nm for the fusion treatment of plastics parts.

The inventive dibenzorylenetetracarboximides I are suitable for a series of further uses, such as the general coloring of organic and inorganic materials, for example of coatings, printing inks and plastics, for preparing aqueous polymer dispersions which absorb in the near infrared region of the electromagnetic spectrum, for obtaining markings and inscriptions which absorb infrared light but are invisible to the human eye, as infrared absorbers for heat management and as active components in photovoltaics.

The compounds of the formula (I) are particularly advantageously suitable for use in organic photovoltaics (OPVs). In principle, these compounds are suitable for use in dye-sensitized solar cells. However, preference is given to their use in solar cells which are characterized by diffusion of excited states (exciton diffusion). In this case, one or both of the semiconductor materials utilized is notable for a diffusion of excited states. Also suitable is the combination of at least one semiconductor material which is characterized by diffusion of excited states with polymers which permit conduction of the excited states along the polymer chain. In the context of the invention, such solar cells are referred to as excitonic solar cells. The direct conversion of solar energy to electrical energy in solar cells is based on the internal photo effect of a semiconductor material, i.e. the generation of electron-hole pairs by absorption of photons and the separation of the negative and positive charge carriers at a p-n transition or a Schottky contact. An exciton can form, for example, when a photon penetrates into a semiconductor and excites an electron to transfer from the valence band into the conduction band. In order to generate current, the excited state generated by the absorbed photons must, however, reach a p-n transition in order to generate a hole and an electron which then flow to the anode and cathode. The photovoltage thus generated can bring about a photocurrent in an external circuit, through which the solar cell delivers its power. The semiconductor can absorb only those photons which have an energy which is greater than its band gap. The size of the semiconductor band gap thus determines the proportion of sunlight which can be converted to electrical energy. The excitonic solar cells described consist normally of two absorbing materials with different band gaps in order to very effectively utilize the solar energy. Most organic semiconductors have exciton diffusion lengths of up to 10 nm. There is still a need here for organic semiconductors through which the excited state can be passed on over very large distances. It has now been found that, surprisingly, the compounds of the general formula I described above are particularly advantageously suitable for use in excitonic solar cells.

Suitable organic solar cells generally have a layer structure and generally comprise at least the following layers: anode, photoactive layer and cathode. These layers generally consist of a substrate customary therefor. The structure of organic solar cells is described, for example, in US 2005/0098726 A1 and US 2005/0224905 A1, which are fully incorporated here by reference.

Suitable substrates are, for example, oxidic materials (such as glass, quartz, ceramic, $SiO_2$, etc.), polymers (e.g. polyvinyl chloride, polyolefins such as polyethylene and polypropylene, polyesters, fluoropolymers, polyamides, polyurethanes, polyalkyl (meth)acrylates, polystyrene and mixtures and composites thereof) and combinations thereof.

Suitable electrodes (cathode, anode) are in principle metals (preferably of groups 8, 9, 10 or 11 of the Periodic Table, e.g. Pt, Au, Ag, Cu, Al, In, Mg, Ca), semiconductors (e.g. doped Si, doped Ge, indium tin oxide (ITO), gallium indium tin oxide (GITO), zinc indium tin oxide (ZITO), etc.), metal alloys (e.g. based on Pt, Au, Ag, Cu, etc., especially Mg/Ag alloys), semiconductor alloys, etc. The anode used is preferably a material essentially transparent to incident light. This includes, for example, ITO, doped ITO, ZnO, $TiO_2$, Ag, Au, Pt. The cathode used is preferably a material which essentially reflects the incident light. This includes, for example, metal films, for example of Al, Ag, Au, In, Mg, Mg/Al, Ca, etc.

For its part, the photoactive layer comprises at least one or consists of at least one layer which comprises, as an organic semiconductor material, at least one compound which is selected from compounds of the formulae I and II as defined above. In one embodiment, the photoactive layer comprises at least one organic acceptor material. In addition to the photoactive layer, there may be one or more further layers, for example a layer with electron-conducting properties (ETL, electron transport layer) and a layer which comprises a hole-conducting material (hole transport layer, HTL) which need not absorb, exciton- and hole-blocking layers (e.g. EBLs) which should not absorb, multiplication layers. Suitable exciton- and hole-blocking layers are described, for example, in U.S. Pat. No. 6,451,415.

Suitable exciton blocker layers are, for example, bathocuproins (BCPs), 4,4',4"-tris(N-(3-methylphenyl)-N-phenylamino)triphenylamine (m-MTDATA) or polyethylenedioxythiophene (PEDOT), as described in U.S. Pat. No. 7,026,041.

The inventive excitonic solar cells are based on photoactive donor-acceptor heterojunctions. When at least one compound of the formula (I) is used as the HTM, the corresponding ETM must be selected such that, after excitation of the compounds, a rapid electron transfer to the ETM takes place. Suitable ETMs are, for example, C60 and other fullerenes, perylene-3,4:9,10-bis(dicarboximides), PTCDIs, etc. When at least one compound of the formula (I) is used as the ETM, the complementary HTM must be selected such that, after excitation of the compound, a rapid hole transfer to the HTM takes place. The heterojunction may have a flat configuration (cf. Two layer organic photovoltaic cell, C. W. Tang, Appl. Phys. Lett., 48 (2), 183-185 (1986) or N. Karl, A. Bauer, J. Holzäpfel, J. Marktanner, M. Möbus, F. Stölzle, Mol. Cryst. Liq. Cryst., 252, 243-258 (1994).) or be implemented as a bulk heterojunction (or interpenetrating donor-acceptor network; cf., for example, C. J. Brabec, N. S. Sariciftci, J. C. Hummelen, Adv. Funct. Mater., 11 (1), 15 (2001). The photoactive layer based on a heterojunction between at least one compound of the formula (I) and an HTL or ETL can be used in solar cells with MiM, pin, pn, Mip or Min structure (M=metal, p=p-doped organic or inorganic semiconductor, n=n-doped organic or inorganic semiconductor, i=intrinsically conductive system of organic layers; cf., for example, J. Drechsel et al., Org. Eletron., 5 (4), 175 (2004) or Maennig et al., Appl. Phys. A 79, 1-14 (2004)). It can also be used in tandem cells, as described by P. Peumnas, A. Yakimov, S. R. Forrest in J. Appl. Phys, 93 (7), 3693-3723 (2003) (cf. U.S. Pat. No. 4,461,922, U.S. Pat. No. 6,198,091 and U.S. Pat. No. 6,198,092). It can also be used in tandem cells composed of two or more MiM, pin, Mip or Min diodes stacked on one another (cf. patent application DE 103 13 232.5) (J. Drechsel et al., Thin Solid Films, 451-452, 515-517 (2004)).

Thin layers of the compounds and of all other layers can be produced by vapor deposition under reduced pressure or in inert gas atmosphere, by laser ablation or by solution- or dispersion-processible methods such as spin-coating, knife-coating, casting methods, spraying, dip-coating or printing (e.g. inkjet, flexographic, offset, gravure; intaglio, nanoimprinting). The layer thicknesses of the M, n, i and p layers are typically from 10 to 1000 nm, preferably from 10 to 400 nm.

The substrates used are, for example, glass, metal foils or polymer films which are generally coated with a transparent conductive layer (for example $SnO_2$:F, $SnO_2$:In, ZnO:Al, carbon nanotubes, thin metal layers).

In addition to the compounds of the general formula (I), the following semiconductor materials are suitable for use in organic photovoltaics:

Acenes such as anthracene, tetracene, pentacene, each of which may be substituted or unsubstituted. Substituted acenes preferably comprise at least one substituent selected from electron-donating substituents (e.g. alkyl, alkoxy, ester, carboxylate or thioalkoxy), electron-withdrawing substituents (e.g. halogen, nitro or cyano) and combinations thereof. These include 2,9-dialkylpentacenes and 2,10-dialkylpentacenes, 2,10-dialkoxypentacenes, 1,4,8,11-tetraalkoxypentacenes and rubrene (5,6,11,12-tetraphenylnaphthacene). Suitable substituted pentacenes are described in US 2003/0100779 and U.S. Pat. No. 6,864,396, which are incorporated here by reference. A preferred acene is rubrene (5,6,11,12-tetraphenylnaphthacene).

Phthalocyanines, for example phthalocyanines which bear at least one halogen substituent, such as hexadecachlorophthalocyanines and hexadecafluorophthalocyanines, metal-free phthalocyanines or phthalocyanines comprising divalent metals or metal atom-containing groups, especially those of titanyloxy, vanadyloxy, iron, copper, zinc, etc. Suitable phthalocyanines are especially copper phthalocyanine, zinc phthalocyanine, metal-free phthalocyanine, copper hexadecachlorophthalocyanine, zinc hexadecachlorophthalocyanine, metal-free hexadecachlorophthalocyanine, copper hexadecafluorophthalocyanine, hexadecafluorophthalocyanine or metal-free hexadecafluorophthalocyanine.

Porphyrins, for example 5, 10,15,20-tetra(3-pyridyl)porphyrin (TpyP).

Liquid-crystalline (LC) materials, for example coronenes such as hexabenzocoronene (HBC-PhC12), coronenediimides, or triphenylenes such as 2,3,6,7,10,11-hexahexylthiotriphenylene (HTT6), 2,3,6,7,10,11-hexakis(4-n-nonylphenyl)-triphenylene (PTP9) or 2,3,6,7,10,11-hexakis (undecyloxy)triphenylene (HAT11). Particular preference is given to liquid-crystalline materials which are discotic.

Thiophenes, oligothiophenes and substituted derivatives thereof. Suitable oligothiophenes are quaterthiophenes, quinquethiophenes, sexithiophenes, $\alpha,\omega$-di($C_1$-$C_8$)alkyloligothiophenes such as $\alpha,\omega$-dihexylquaterthiophenes, $\alpha,\omega$-dihexylquinquethiophenes and $\alpha,\omega$-dihexylsexithiophenes, poly (alkylthiophenes) such as poly(3-hexylthiophene), bis (dithienothiophenes), anthradithiophenes and dialkylanthradithiophenes such as dihexylanthradithiophene, phenylene-thiophene (P-T) oligomers and derivatives thereof, especially $\alpha,\omega$-alkyl-substituted phenylene-thiophene oligomers.

Also suitable are compounds of the $\alpha,\alpha'$-bis(2,2-dicyanovinyl)quinquethiophene (DCV5T) type, (3-(4-octylphenyl)-2,2'-bithiophene) (PTOPT), poly(3-(4'-(1,4,7-trioxaoctyl)phenyl)thiophene) (PEOPT), poly(3-(2'-methoxy-5'-octylphenyl)thiophene) (POMeOPT), poly(3-octylthiophene) (P3OT), poly(pyridopyrazinevinylene)-polythiophene blends, such as EHH-PpyPz, PTPTB copolymers, BBL, F8BT, PFMO; see Brabec C., Adv. Mater., 2996, 18, 2884, (PCPDTBT) poly[2,6-(4,4-bis(2-ethylhexyl)-4H-cyclopenta[2,1-b; 3,4-b']dithiophene)-4,7-(2,1,3-benzothiadiazole)]. Paraphenylenevinylene and paraphenylenevinylene-comprising oligomers and polymers, for example polyparaphenylenevinylene, MEH-PPV (poly(2-methoxy-5-(2'-ethylhexyloxy)-1,4-phenylenevinylene)), M DMO-PPV (poly(2-methoxy-5-(3',7'-dimethyloctyloxy)-1, 4-phenylenevinylene)), PPV, CN-PPV (with various alkoxy derivatives).

Phenyleneethynylene/phenylenevinylene (PPE-PPV) hybrid polymers.

Polyfluorenes and alternating polyfluorene copolymers, for example with 4,7-dithien-2'-yl-2,1,3-benzothiadiazole; also suitable are poly(9,9'-dioctylfluorene-co-benzothiadiazole) ($F_8BT$), poly(9,9'-dioctylfluorene-co-bis-N,N'-(4-butylphenyl)-bis-N,N'-phenyl-1,4-phenylenediamine) (PFB).

Polycarbazoles, i.e. carbazole-comprising oligomers and polymers, such as (2,7) and (3,6).

Polyanilines, i.e. aniline-comprising oligomers and polymers, such as (2,7) and (3,6).

Triarylamines, polytriarylamines, polycyclopentadienes, polypyrroles, polyfurans, polysiloles, polyphospholes, TPD, CBP, spiro-MeOTAD.

Fullerenes, especially C60 and derivatives thereof such as PCBM (=[6,6]-phenyl-C61-butyric acid methyl ester). In such cells, the fullerene derivative is a hole conductor.

Copper(I) iodide, copper(I) thiocyanate.

p-n-Mixed materials, i.e. donor and acceptor in one material, polymer, block polymer, polymers with C60s, C60 azo dyes, triad carotenoid-porphyrin-quinoid LC donor/acceptor systems, as described by S. Kelly in Adv. Mater. 2006, 18, 1754.

All aforementioned semiconductor materials may also be doped. Examples of dopants for p-semiconductors: 2,3,5,6-tetrafluoro-7,7,8,8-tetracyanoquinodimethane ($F_4$-TCNQ), etc.

The inventive (novel) compounds (I) are also suitable particularly advantageously as organic semiconductors. They function generally as n-semiconductors. When the compounds of the formula (I) used in accordance with the invention are combined with other semiconductors and the position of the energy levels causes the other semiconductors to function as n-semiconductors, the compounds (I) can also function as p-semiconductors in exceptional cases. This is the case, for example, for the combination with cyano-substituted perylenetetracarboximides. The compounds of the formula (I) are notable for their air stability. They also possess a high charge transport mobility and have a high on/off ratio. They are suitable in a particularly advantageous manner for organic field-effect transistors. The inventive compounds are advantageously suitable for preparing integrated circuits (ICs) for which the n-channel MOSFETs (metal oxide semiconductor field-effect transistors) customary to date are used. These are CMOS-like semiconductor units, for example for microprocessors, microcontrollers, static RAM and other digital logic units. For the production of semiconductor materials, the processes according to the invention can be processed further by one of the following processes: printing (offset, flexographic, gravure, screen, inkjet, electrophotography), evaporation, laser transfer, photolithography, dropcasting. They are suitable in particular for use in displays (especially large-area and/or flexible displays) and RFID tags.

The inventive compounds are also suitable particularly advantageously for data storage, in diodes, especially in OLEDs, in photovoltaics, as UV absorbers, as optical brighteners, as invisible labels and as fluorescent labels for biomolecules such as proteins, DNA, sugars and combinations thereof.

The inventive compounds are also suitable particularly advantageously as a fluorescent dye in a display based on fluorescence conversion; in a light-collecting plastics part which, if appropriate, is combined with a solar cell; as a pigment dye in electrophoretic displays; as a fluorescent dye in an application based on chemoluminescence (for example in glow sticks).

The inventive compounds are also particularly advantageously suitable as a fluorescent dye in a display based on fluorescence conversion. Such displays generally comprise a transparent substrate, a fluorescent dye disposed on the substrate and a radiation source. Customary radiation sources transmit blue (color-by-blue) or UV light (color-by-uv). The dyes absorb either the blue or the UV light and are used as green emitters. In these displays, for example, the red light is generated by virtue of the red emitter being excited by a blue or UV light-absorbing green emitter. Suitable color-by-blue displays are described, for example, in WO 98/28946. Suitable color-by-uv displays are described, for example, by W. A. Crossland, I. D. Sprigle and A. B. Davey in Photoluminescent LCDs (PL-LCD) using phosphors Cambridge University and Screen Technology Ltd., Cambridge, UK.

The inventive compounds are also particularly suitable as fluorescence emitters in OLEDs, in which they are excited either by electroluminescence or by an appropriate phosphorescence emitter via Förster energy transfer (FRET).

The inventive compounds are also particularly suitable in displays which switch colors on and off based on an electrophoretic effect via charged pigment dyes. Such electrophoretic displays are described, for example, in US 2004/0130776.

The inventive compounds are also particularly suitable for use in a light-collecting plastics part which absorbs light over a large surface and at whose edges the light is emitted after multiple refraction (so-called LISAs). Such LISAs may have, at the edges, solar cells, for example silicon solar cells or organic solar cells, which convert the concentrated light to electrical energy. A combination of light-collecting plastics with solar cells is described, for example, in U.S. Pat. No. 4,110,123.

The inventive compounds are also particularly suitable in chemoluminescence applications. These include so-called "glow sticks". They can be produced by dissolving at least one compound of the formula (I), for example in an alkyl phthalate. The chemoluminescence can be induced by mixing an oxalic ester with hydrogen peroxide, for example after these two initially separate components have been mixed by breaking a piece of glass. The resulting reaction energy leads to the excitation and fluorescence of the dyes. Such glow sticks can be used as emergency light, for example for angling, in lifejackets for emergency sea rescue or other safety applications.

The invention further provides organic field-effect transistors comprising a substrate comprising at least one gate structure, a source electrode and a drain electrode and at least one compound of the formula I as defined above as an n-semiconductor. The invention further provides substrates comprising a multitude of organic field-effect transistors, wherein at least some of the field-effect transistors comprise at least one compound of the formula I as defined above as an n-semiconductor. The invention also provides semiconductor units which comprise at least one such substrate.

A specific embodiment is a substrate with a pattern (topography) of organic field-effect transistors, each transistor comprising
an organic semiconductor disposed on the substrate;
a gate structure for controlling the conductivity of the conductive channel; and
conductive source and drain electrodes at the two ends of the channel,
the organic semiconductor consisting of at least one compound of the formula (I) or comprising a compound of the formula (I). In addition, the organic field-effect transistor generally comprises a dielectric.

A further specific embodiment is a substrate having a pattern of organic field-effect transistors, each transistor forming an integrated circuit or being part of an integrated circuit and at least some of the transistors comprising at least one compound of the formula (I).

Suitable substrates are in principle the materials known for this purpose. Suitable substrates comprise, for example, metals (preferably metals of groups 8, 9, 10 or 11 of the Periodic Table, such as Au, Ag, Cu), oxidic materials (such as glass, quartz, ceramics, $SiO_2$), semiconductors (e.g. doped Si, doped Ge), metal alloys (for example based on Au, Ag, Cu, etc.), semiconductor alloys, polymers (e.g. polyvinyl chloride, polyolefins such as polyethylene and polypropylene, polyesters, fluoropolymers, polyamides, polyimides, polyurethanes, polyalkyl (meth)acrylates, polystyrene and mixtures and composites thereof), inorganic solids (e.g. ammonium chloride), paper and combinations thereof. The substrates may be flexible or inflexible, and have a curved or planar geometry, depending on the desired use.

A typical substrate for semiconductor units comprises a matrix (for example a quartz or polymer matrix) and, optionally, a dielectric top layer.

Suitable dielectrics are $SiO_2$, polystyrene, poly-α-methylstyrene, polyolefins (such as polypropylene, polyethylene, polyisobutene), polyvinylcarbazole, fluorinated polymers (e.g. Cytop, CYMM), cyanopullulans, polyvinylphenol, poly-p-xylene, polyvinyl chloride, or polymers crosslinkable thermally or by atmospheric moisture. Specific dielectrics are "self-assembled nanodielectrics", i.e. polymers which are obtained from monomers comprising SiCl functionalities, for example $Cl_3SiOSiCl_3$, $Cl_3Si$—$(CH_2)$—$_6$—$SiCl_3$, $Cl_3Si$—$(CH_2)_{12}$—$SiCl_3$, and/or which are crosslinked by atmospheric moisture or by addition of water diluted with solvents (see, for example, Faccietti Adv. Mat. 2005, 17, 1705-1725). Instead of water, it is also possible for hydroxyl-containing polymers such as polyvinylphenol or polyvinyl alcohol or copolymers of vinylphenol and styrene to serve as crosslinking components. It is also possible for at least one further polymer to be present during the crosslinking operation, for example polystyrene, which is then also crosslinked (see Faciett, US patent application 2006/0202195).

The substrate may additionally have electrodes, such as gate, drain and source electrodes of OFETs, which are normally localized on the substrate (for example deposited onto or embedded into a nonconductive layer on the dielectric). The substrate may additionally comprise conductive gate electrodes of the OFETs, which are typically arranged below the dielectric top layer (i.e. the gate dielectric).

In a specific embodiment, an insulator layer (gate insulating layer) is present on at least part of the substrate surface. The insulator layer comprises at least one insulator which is preferably selected from inorganic insulators such as $SiO_2$, SiN, etc., ferroelectric insulators such as $Al_2O_3$, $Ta_2O_5$, $La_2O_5$, $TiO_2$, $Y_2O_3$, etc., organic insulators such as polyimides, benzocyclobutene (BCB), polyvinyl alcohols, polyacrylates, etc., and combinations thereof.

Suitable materials for source and drain electrodes are in principle electrically conductive materials. These include metals, preferably metals of groups 8, 9, 10 or 11 of the Periodic Table, such as Pd, Au, Ag, Cu, Al, Ni, Cr, etc. Also suitable are conductive polymers such as PEDOT (=poly(3, 4-ethylenedioxythiophene)); PSS (=poly(styrenesulfonate)), polyaniline, surface-modified gold, etc. Preferred electrically conductive materials have a specific resistance of less than $10^{-3}$ ohm x meter, preferably less than $10^{-4}$ ohm x meter, especially less than $10^{-6}$ or $10^{-7}$ ohm x meter.

In a specific embodiment, drain and source electrodes are present at least partly on the organic semiconductor material. It will be appreciated that the substrate may comprise further components as used customarily in semiconductor materials or ICs, such as insulators, resistors, capacitors, conductor tracks, etc.

The electrodes may be applied by customary processes, such as evaporation, lithographic processes or another structuring process.

The semiconductor materials may also be processed with suitable auxiliaries (polymers, surfactants) in disperse phase by printing.

In a first preferred embodiment, the deposition of at least one compound of the general formula I (and if appropriate further semiconductor materials) is carried out by a gas phase deposition process (physical vapor deposition, PVD). PVD processes are performed under high-vacuum conditions and comprise the following steps: evaporation, transport, deposition. It has been found that, surprisingly, the compounds of the general formula I are suitable particularly advantageously for use in a PVD process, since they essentially do not decompose and/or form undesired by-products. The material deposited is obtained in high purity. In a specific embodiment, the deposited material is obtained in the form of crystals or comprises a high crystalline content. In general, for the PVD, at least one compound of the general formula I is heated to a temperature above its evaporation temperature and deposited on a substrate by cooling below the crystallization temperature. The temperature of the substrate in the deposition is preferably within a range from about 20 to 250° C., more preferably from 50 to 200° C. It has been found that, surprisingly, elevated substrate temperatures in the deposition of the compounds of the formula I can have advantageous effects on the properties of the semiconductor elements achieved.

The resulting semiconductor layers generally have a thickness which is sufficient for ohmic contact between source and drain electrodes. The deposition can be effected under an inert atmosphere, for example under nitrogen, argon or helium.

The deposition is effected typically at ambient pressure or under reduced pressure. A suitable pressure range is from about $10^{-7}$ to 1.5 bar.

The compound of the formula (I) is preferably deposited on the substrate in a thickness of from 10 to 1000 nm, more preferably from 15 to 250 nm. In a specific embodiment, the compound of the formula I is deposited at least partly in crystalline form. For this purpose, especially the above-described PVD process is suitable. Moreover, it is possible to use previously prepared organic semiconductor crystals. Suitable processes for obtaining such crystals are described by R. A. Laudise et al. in "Physical Vapor Growth of Organic Semi-Conductors", Journal of Crystal Growth 187 (1998), pages 449-454, and in "Physical Vapor Growth of Centimeter-sized Crystals of x-Hexathiophene", Journal of Crystal Growth 1982 (1997), pages 416-427, which are incorporated here by reference.

The compounds of the general formula (I) can also particularly advantageously be processed from solution. In a second preferred embodiment, the deposition of at least one compound of the general formula (I) (and if appropriate further semiconductor materials) is therefore effected by spin-coating. The compounds of the formula (I) should also be suitable for producing semiconductor elements, especially OFETs or based on OFETs, by a printing process. It is possible for this purpose to use customary printing processes (inkjet, flexographic, offset, gravure; intaglio printing, nanoprinting). Preferred solvents for the use of the compounds of the formula (I) in a printing process are aromatic solvents such as toluene, xylene, etc. It is also possible to add thickening substances such as polymers, for example polystyrene, etc., to these "semiconductor inks". In this case, the dielectrics used are the aforementioned compounds.

In a preferred embodiment, the inventive field-effect transistor is a thin-film transistor (TFT). In a customary construction, a thin-film transistor has a gate electrode disposed on the substrate, a gate insulator layer disposed thereon and on the substrate, a semiconductor layer disposed on the gate insulator layer, an ohmic contact layer on the semiconductor layer, and a source electrode and a drain electrode on the ohmic contact layer.

In a preferred embodiment, the surface of the substrate, before the deposition of at least one compound of the general formula (I) (and if appropriate of at least one further semiconductor material), is subjected to a modification. This modification serves to form regions which bind the semiconductor materials and/or regions on which no semiconductor materials can be deposited. The surface of the substrate is preferably modified with at least one compound (C1) which is suitable for binding to the surface of the substrate and to the compounds of the formula (I). In a suitable embodiment, a portion of the surface or the complete surface of the substrate is coated with at least one compound (C1) in order to enable improved deposition of at least one compound of the general formula (I) (and if appropriate further semiconductive compounds). A further embodiment comprises the deposition of a pattern of compounds of the general formula (C1) on the substrate by a corresponding production process. These include the mask processes known for this purpose and so-called "patterning" processes, as described, for example, in U.S. Ser. No. 11/353,934, which is incorporated here fully by reference.

Suitable compounds of the formula (C1) are capable of a binding interaction both with the substrate and with at least one semiconductor compound of the general formula I. The term "binding interaction" comprises the formation of a chemical bond (covalent bond), ionic bond, coordinative interaction, van der Waals interactions, e.g. dipole-dipole interactions etc., and combinations thereof. Suitable compounds of the general formula (C1) are:

silanes, phosphonic acids, carboxylic acids, hydroxamic acids, such as alkyltrichlorosilanes, e.g. n-octadecyltrichlorosilane; compounds with trialkoxysilane groups, e.g. alkyltrialkoxysilanes such as n-octadecyltrimethoxy-silane, n-octadecyltriethoxysilane, n-octadecyltri(n-propyl)oxysilane, n-octadecyltri(isopropyl)oxysilane; trialkoxyaminoalkylsilanes such as triethoxyaminopropylsilane and N-[(3-triethoxysilyl)propyl]ethylenediamine; trialkoxyalkyl 3-glycidyl ether silanes such as triethoxypropyl 3-glycidyl ether silane; trialkoxyallylsilanes such as allyltrimethoxysilane; trialkoxy(isocyanato-alkyl)silanes; trialkoxysilyl(meth)acryloyloxyalkanes and trialkoxysilyl(meth)-acrylamidoalkanes such as 1-triethoxysilyl-3-acryloyloxypropane.

amines, phosphines and sulfur-comprising compounds, especially thiols.

The compound (C1) is preferably selected from alkyltrialkoxysilanes, especially n-octadecyltrimethoxysilane, n-octadecyltriethoxysilane; hexaalkyldisilazanes, and especially hexamethyldisilazane (HMDS); $C_8$-$C_{30}$-alkylthiols, especially hexadecanethiol; mercaptocarboxylic acids and mercaptosulfonic acids, especially mercaptoacetic acid, 3-mercaptopropionic acid, mercaptosuccinic acid, 3-mercapto-1-propanesulfonic acid and the alkali metal and ammonium salts thereof.

Various semiconductor architectures comprising the inventive semiconductors are also conceivable, for example top contact, top gate, bottom contact, bottom gate, or else a vertical construction, for example a VOFET (vertical organic field-effect transistor), as described, for example, in US 2004/0046182.

The layer thicknesses are, for example, from 10 nm to 5 µm in semiconductors, from 50 nm to 10 µm in the dielectric; the electrodes may, for example, be from 20 nm to 1 µm thick. The OFETs may also be combined to form other components such as ring oscillators or inverters.

A further aspect of the invention is the provision of electronic components which comprise a plurality of semiconductor components, which may be n- and/or p-semiconductors. Examples of such components are field-effect transistors (FETs), bipolar junction transistors (BJTs), tunnel diodes, converters, light-emitting components, biological and chemical detectors or sensors, temperature-dependent detectors, photodetectors such as polarization-sensitive photodetectors, gates, AND, NAND, NOT, OR, TOR and NOR gates, inverters, registers, switches, timer units, static or dynamic stores and other dynamic or sequential, logical or other digital components including programmable circuits.

EXAMPLES

The 5,11-dibromotetracene used as reactant III in the examples was prepared as follows:

A solution of 708 mg (4 mmol) of N-bromosuccinimide in 40 ml of dimethylformamide was added to a solution, heated to 60° C., of 456 mg (2 mmol) of tetracene in 200 ml of chloroform. The resulting solution was stirred at 60° C. for 5 h and then cooled to room temperature. After the chloroform had been evaporated under reduced pressure and water had been added, the precipitate formed was filtered off, dried and recrystallized from toluene. 710 mg of 5,11-dibromotetracene (III) were obtained in the form of an orange solid, which corresponds to a yield of 92%.

Example 1

N,N'-bis(2,6-diisopropylphenyl)-9,10;21,22-dibenzopentarylene-3,4;15,16-tetracarboximide Ia1

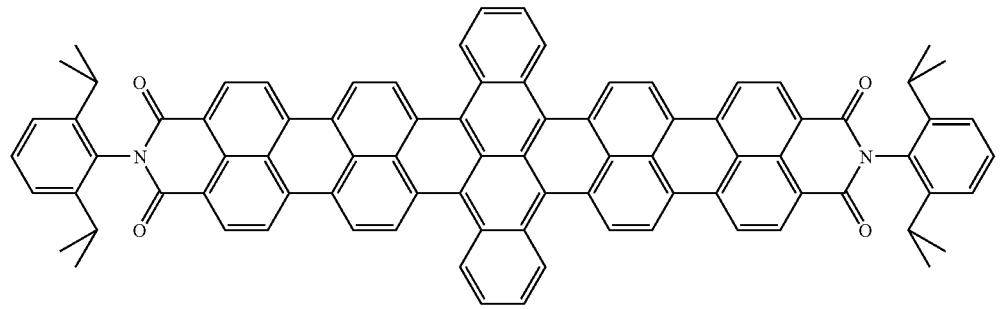

a) Preparation of 5,11-bis[N-(2,6-diisopropylphenyl)-3,4-dicarboximideperylen-9-yl)tetracene IVa1

Under protective gas, 20 mg (13 μmol) of tris(dibenzylideneacetone)dipalladium, 40 mg (80 μmol) of bis(2-diphenylphosphino)phenyl ether and 2 ml of a 2M solution of potassium carbonate (4 mmol) in water were added to a solution of 193 mg (0.5 mmol) of 5,11-dibromotetracene and 608 mg (1 mmol) of N-(2,6-diisopropylphenyl)-9-(4,4,5,5-tetramethyl-1,3,2-dioxaboran-2-yl)perylene-3,4-dicarboximide in 30 ml of toluene and 2 ml of ethanol. The mixture was heated to 95° C. for 15 h.

After cooling to room temperature, the organic phase was washed repeatedly with water and dried over magnesium sulfate. The crude product obtained after removal of the organic solvent under reduced pressure was subjected to column chromatography on silica gel with dichloromethane as the eluent.

424 mg of IVa1 were obtained in the form of a deep red solid, which corresponds to a yield of 71%.

Analytical Data:

$R_f(CH_2Cl_2)=0.5$;

Absorption: $(CHCl_3)$: $\lambda_{max}(\varepsilon)=524$ (97 100), 355 (8500) nm (l/mol cm).

b) Cyclodehydrogenation

A solution of 260 mg (2 mmol) of anhydrous iron(III) chloride in 3 ml of nitromethane was added slowly to a solution of 120 mg (0.1 mmol) of IVa1 in 10 ml of dry dichloromethane. The mixture was then stirred with exclusion of light at room temperature for 4 h.

The precipitate formed after precipitating the reaction mixture in 50 ml of methanol was filtered off, dried under reduced pressure and then heated in 3 ml of ethanolamine in the presence of 2 g of potassium carbonate to 120° C. for 2 h.

The crude product precipitated by adding water after cooling to room temperature was filtered off, washed with methanol and dichloromethane and then purified by extraction with chlorobenzene.

68 mg of Ia1 were obtained in the form of a violet solid, which corresponds to a yield of 58%.

Analytical Data:

Absorption (chlorobenzene): $\lambda_{max}=1018$, 542, 318 nm.

Example 2

N,N'-bis(2,6-diisopropylphenyl)-1,6,13,18-tetra[(4-tert-octyl)phenoxy]-9,10;21,22-dibenzopentarylene-3,4; 15,16-tetracarboximide Ia2

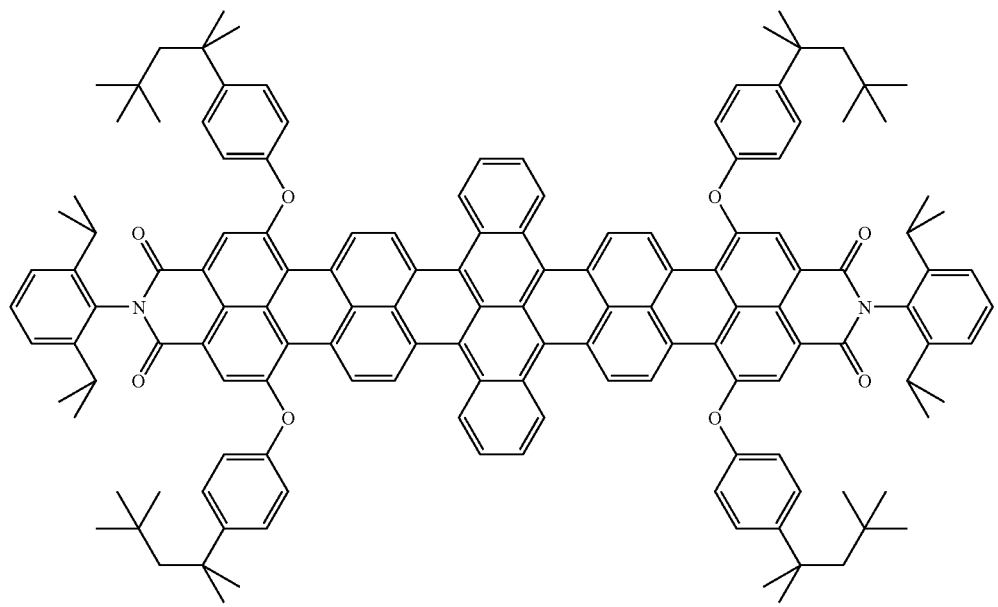

a) 5,11-bis[N-(2,6-diisopropylphenyl)-1,6-bis((4-tert-octyl)phenoxy)-3,4-dicarboximide-perylen-9-yl] tetracene IVa2

Under protective gas, 610 mg (0.6 mmol) of N-(2,6-diisopropylphenyl)-1,6-bis((4-tert-octyl)phenoxy)-9-(4,4,5,5-tetramethyl-1,3,2-dioxaboran-2-yl)perylene-3,4-dicarboximide and 116 mg (0.3 mmol) of 5,11-dibromotetracene were dissolved in 40 ml of toluene and 4 ml of ethanol while heating to 80° C. Subsequently, 16 mg (12 µmol) of tris(dibenzylideneacetone)dipalladium, 30 mg (60 µmol) of bis(2-diphenylphosphino)phenyl ether and 2.5 ml of a 2M solution of potassium carbonate (0.1 mmol) in water were added. The mixture was heated to 85° C. for 15 h.

After cooling to room temperature, the organic phase was washed repeatedly with water and dried over magnesium sulfate. The crude product obtained after removing the organic solvent under reduced pressure was subjected to column chromatography on silica gel with toluene as the eluent.

354 mg of IVa2 were obtained in the form of a deep red solid, which corresponds to a yield of 59%.

Analytical Data:

$R_f$(toluene)=0.62;

Absorption (CHCl$_3$): $\lambda_{max}$(∈)=530 (94 860), 420 (16 960) nm (l/mol cm).

b) Cyclodehydrogenation

A solution of 260 mg (2 mmol) of anhydrous iron(III) chloride in 3 ml of nitromethane was added slowly to a solution of 200 mg (0.1 mmol) of IVa2 in 10 ml of dry dichloromethane. The mixture was then stirred with exclusion of light at room temperature for 3 h.

The precipitate formed after precipitation of the reaction mixture in 50 ml of methanol was filtered off, dried under reduced pressure, then dissolved in 1 ml of dimethyl-formamide and heated together with 3 ml of ethanolamine and 2 g of potassium carbonate to 120° C. for 2 h.

The crude product precipitated by adding water after cooling to room temperature was filtered off, dried and then purified to a column chromatography on silica gel with a 1:1 mixture of petroleum ether and dichloromethane.

105 mg of Ia2 were obtained in the form of a violet solid, which corresponds to a yield of 53%.

Analytical Data:

$R_f$(toluene)=0.63;

Absorption (CH$_2$Cl$_2$): $\lambda_{max}$(∈)=1037 (149 500), 567 (46 700), 321 nm (84 500) nm (l/mol cm);

Absorption (PMMA): $\lambda_{max}$=571, 1054 nm.

Example 3

N,N'-bis(N-(1-heptyloctyl)-9, 10:21,22-dibenzopentarylene-3,4:15,16-bis(dicarboximide)

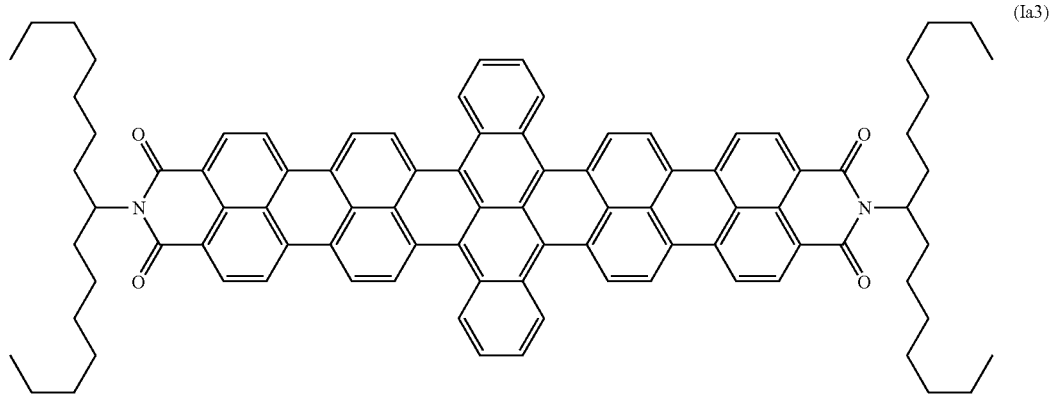

(Ia3)

a) Preparation of N-(1-heptyloctyl)-9-bromoperylene-3,4-dicarboximide IVa3

Under protective gas, a mixture of 3 g (7.48 mmol) of 9-bromoperylene-3,4-dicarboxylic anhydride and 8 g (35 mmol) of 1-heptyloctylamine in 150 ml of N-methylpyrrolidone and 3 ml of acetic acid was heated to 135° C. for 20 h.

After cooling to room temperature, the reaction mixture was precipitated in 500 ml of water. The precipitate was filtered off, washed with water and methanol and dried under reduced pressure. The resulting crude product was purified by column chromatography on silica gel with dichloromethane as the eluent. 2.9 g (63%) of the title compound were obtained in the form of a red solid with a melting point of 163° C.

Analytical Data:

$R_f$(toluene)=0.66;

$^1$H NMR (500 MHz, CD$_2$Cl$_2$, 25° C.): δ=8.63 (d, 1H, J=8.2 Hz), 8.61 (d, 1H, J=8.2 Hz), 8.45 (d, 1H, J=8.2 Hz), 8.42 (d, 1H, J=8.2 Hz), 8.36 (d, 1H, J=7.6 Hz), 8.27 (d, 1H, J=8.2 Hz), 8.20 (d, 1H, J=8.2 Hz), 7.87 (d, 1H, J=8.2 Hz), 7.70 (t, 1H, J=7.6 Hz), 5.17-5.05 (m, 1H), 2.23-2.16 (m, 2H), 1.89-1.81 (m, 2H), 1.27-1.20 (m, 20H), 0.82-0.77 (m, 6H).

$^{13}$C NMR (Spinecho, 125 MHz, CD$_2$Cl$_2$, 25° C.): δ=165.16, 164.12, 136.16, 132.73, 132.01, 131.26, 129.90, 129.73, 129.47, 128.93, 128.20, 126.14, 126.08, 124.38, 123.67, 122.06, 121.31, 120.75, 120.48, 54.69, 32.65, 32.15, 29.90, 29.59, 27.40, 22.98, 14.53.

IR (KBr) ν=2924, 2853, 2365, 1697, 1653, 1594, 1572, 1450, 1460, 1408, 1355, 1292, 1244, 1172, 1136, 1109, 840, 810, 754 cm$^{-1}$;

UV-Vis (CHCl$_3$) $\lambda_{max}$ (∈): 514 (51000), 489 nm (52000 M$^{-1}$ cm$^{-1}$);

fluorescence (CHCl$_3$) $\lambda_{max}$: 571, 544 nm;

MS (FD): [M$^+$] calculated for C$_{37}$H$_{40}$BrN$_2$O$_2$, 610.64; found: 611.1 (100%).

b) Preparation of N-(1-heptyloctyl)-9-(4,4,5,5-tetramethyl-1,3,2-dioxaborolan-2-yl)perylene-3,4-dicarboximide IIIa3

A mixture of 1.2 g (2 mmol) of N-(1-heptyloctyl)-9-bromoperylene-3,4-dicarboximide IVa3, 558 mg (2.5 mmol) of bis(pinacolato)diboron, 44 mg (0.1 mmol) of PdCl$_2$(dppf) (dppf=Ph$_2$PC$_5$H$_4$FeC$_5$H$_4$PPh$_2$) and 588 mg (5.3 mmol) of potassium acetate in 20 ml of dioxane was stirred at 70° C. under an argon atmosphere for 16 h. Thereafter, the reaction mixture was allowed to cool to room temperature.

After cooling to room temperature, the reaction mixture was extracted with dichloromethane and washed twice with water. The organic phase was removed and dried over MgSO$_4$. The resulting crude product was purified by column chromatography on silica gel with dichloromethane as the eluent. 1.0 g (78%) of IIIa3 was obtained in the form of a red solid with the melting point of 213° C.
Analytical Data:
R$_f$(toluene)=0.26;
$^1$H NMR (300 MHz, THF-d$_8$, 25° C.): δ=8.87 (d, 1H, J=7.7 Hz), 8.55-8.47 (m, 6H), 8.15 (d, 1H, J=7.7 Hz), 7.59 (t, 1H, J=7.7 Hz), 5.27-5.17 (m, 1H), 2.40-2.28 (m, 2H), 1.84-1.77 (m, 2H), 1.44 (s, 12H), 1.34-1.24 (m, 20H), 0.85-0.81 (t, 6H, J=6.8 Hz);
$^{13}$C NMR (75 MHz, THF-d$_8$, 25° C.): δ=165.24, 164.33, 139.04, 137.83, 137.28, 132.81, 132.20, 131.45, 130.64, 130.02, 128.60, 127.81, 127.40, 124.38, 123.34, 123.25, 122.04, 121.90, 121.28;
IR (KBr) ν=: 2925, 2854, 2362, 2337, 1691, 1653, 1592, 1507, 1461, 1416, 1376, 1332, 1272, 1246, 1209, 1142, 1113, 1068, 966, 858, 811, 754, 674 cm$^{-1}$;
UV-Vis (CHCl$_3$) λ$_{max}$ (∈): 514 (47000), 489 nm (45000 M$^{-1}$ cm$^{-1}$);
fluorescence (CHCl$_3$) λ$_{max}$: 577, 546 nm;
MS (FD): [M$^+$] calculated for C$_{43}$H$_{52}$BN$_2$O$_4$, 657.71; found: 657.9 (100%).

c) Preparation of 5,11-bis[N-(1-heptyloctyl)-3,4-dicarboximideperylen-9-yl)tetracene IIa3

Under protective gas, a mixture of 25 ml of toluene and 1.5 ml of ethanol was added to 96 mg (0.25 mmol) of 5,11-dibromotetracene and 360 mg (0.5 mmol) of N-(1-heptyloctyl)-9-(4,4,5,5-tetramethyl-1,3,2-dioxaborolan-2-yl) perylene-3,4-dicarboximide. The mixture was stirred at 80° C. for 20 min and then 15 mg of tris(di-benzylideneacetone) dipalladium, 30 mg of bis(2-diphenylphosphinophenyl)ether and 1.5 ml of a 2M solution of K$_2$CO$_3$ in water were added. The reaction mixture was stirred at 85° C. under a protective gas atmosphere for 15 h. After cooling to room temperature, the organic phase was washed repeatedly with water and extracted with toluene. The crude product obtained after removing the organic solvents under reduced pressure was subjected to column chromatography on silica gel with dichloromethane as the eluent. 260 mg (81%) of the title compound were obtained in the form of a deep red solid.
Analytical Data:
R$_f$(toluene)=0.32;
UV-Vis (CHCl$_3$) λ$_{max}$ (rel. int.): 521 (1.0), 489 (0.7);
MS (FD): [M+], calculated for C$_{92}$H$_{90}$N$_2$O$_4$ 1287.75; found: 1288.9 (100%), M$^+$.

d) Cyclodehydrogenation

To a solution of 100 mg (0.078 mmol) of 5,11-bis(N-(1-heptyloctyl)perylene-dicarboximid-9-yl)tetracene 11a3 in 10 ml of dry dichloromethane was added slowly, under a protective gas atmosphere, a solution of 200 mg (1.2 mmol) of anhydrous iron(III) chloride in dry nitromethane (1.5 ml). The mixture was then stirred with exclusion of light at room temperature for 12 h and then poured onto 50 ml of methanol. The precipitate was filtered off, washed with methanol and dried at room temperature under reduced pressure.

The dry precipitate was dissolved in 1 ml of dry dimethylformamide, and 2 g of anhydrous potassium carbonate and 3 ml of ethanolamine were added. The reaction mixture was stirred at 120° C. for 4 h. After cooling to room temperature, 25 ml of water were added to the reaction mixture. The precipitate formed was filtered off, washed with water, methanol and dichloromethane and dried under reduced pressure. The purification of the crude product by column chromatography on silica gel with dichloromethane as the eluent gave 51 mg (51%) of the title compound.
Analysis:
R$_f$=0.72 (dichloromethane);
UV-Vis (CH$_2$Cl$_2$) λ$_{max}$ (rel. int.): 1001 (1.0), 539 (0.34).
MS (FD): [M+], calculated for C$_{92}$H$_{86}$N$_2$O$_4$ 1283.72; found: 1284.4 (100%), M$^+$.

The invention claimed is:
1. A dibenzorylenetetracarboximide of formula I

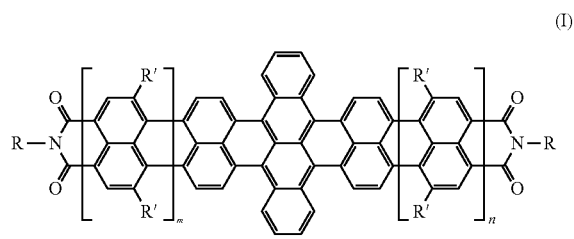

in which R, R', m, and n are each defined as follows:
R' are identical or different radicals:
  hydrogen;
  aryloxy, arylthio, hetaryloxy or hetarylthio, to each of which may be fused further saturated or unsaturated 5- to 7-membered rings whose carbon skeleton may be interrupted by one or more —O—, —S—, —NR$^1$—, —N═CR$^1$—, —CO—, —SO— and/or —SO$_2$— moieties, where the entire ring system may be mono- or polysubstituted by the radicals (i), (ii), (iii), (iv) and/or (v):
  (i) C$_1$-C$_{30}$-alkyl whose carbon chain may be interrupted by one or more —O—, —S—, —NR$^1$—, —N═CR$^1$—, —C≡C—, —CR$^1$═CR$^1$—, —CO—, —SO— and/or —SO$_2$— moieties and which may be mono- or polysubstituted by: C$_1$-C$_{12}$-alkoxy, C$_1$-C$_6$-alkylthio, —C≡CR$^1$, —CR$^1$═CR$^1_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, aryl and/or saturated or unsaturated C$_4$-C$_7$-cycloalkyl whose carbon skeleton may be interrupted by one or more —O—, —S—, —NR$^1$—, —N═CR$^1$—, —CR$^1$═CR$^1$—, —CO—, —SO— and/or —SO$_2$— moieties, where the aryl and cycloalkyl radicals may each be mono- or polysubstituted by C$_1$-C$_{18}$-alkyl and/or the above radicals specified as substituents for alkyl;
  (ii) C$_3$-C$_8$-cycloalkyl whose carbon skeleton may be interrupted by one or more —O—, —S—, —NR$^1$—, —N═CR$^1$—, —CR$^1$═CR$^1$—, —CO—, —SO— and/or —SO$_2$— moieties and to which may be fused further saturated or unsaturated 5- to 7-membered rings whose carbon skeleton may be interrupted by one or more —O—, —S—, —NR$^1$—, —N═CR$^1$═CR$^1$—, —CO—, —SO— and/or —SO₂— moieties, where the entire ring system may be mono- or polysubstituted by: $C_1$-$C_{18}$-alkyl, $C_1$-$C_{12}$-alkoxy, $C_1$-$C_6$-alkylthio, —C≡$CR^1$, —$CR^1$=$CR^1_2$, hydroxyl, mercapto, halogen, cyano, nitro, —$NR^2R^3$, —$NR^2COR^3$, —$CONR^2R^3$, —$SO_2NR^2R^3$, —$COOR^2$ and/or —$SO_3R^2$;

(iii) aryl or hetaryl, to which may be fused further saturated or unsaturated 5- to 7-membered rings whose carbon skeleton may be interrupted by one or more —O—, —S—, —$NR^1$—, —N=$CR^1$—, —$CR^1$=$CR^1$—, —CO—, —SO— and/or —$SO_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡$CR^1$, —$CR^1$=$CR^1_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, aryl and/or hetaryl, each of which may be mono- or polysubstituted by $C_1$-$C_{18}$-alkyl, $C_1$-$C_{12}$-alkoxy, hydroxyl, mercapto, halogen, cyano, nitro, —$NR^2R^3$, —$NR^2COR^3$, —$CONR^2R^3$, —$SO_2NR^2R^3$, —$COOR^2$ and/or —$SO_3R^2$;

(iv) a —U— aryl radical which may be mono- or polysubstituted by the above radicals specified as substituents for the aryl radicals (iii), where U is an —O—, —S—, —$NR^1$—, —CO—, —SO— or —$SO_2$— moiety;

(v) $C_1$-$C_{12}$-alkoxy, $C_1$-$C_6$-alkylthio, —C≡$CR^1$, —$CR^1$=$CR^1_2$, hydroxyl, mercapto, halogen, cyano, nitro, —$NR^2R^3$, —$NR^2COR^3$, —$CONR^2R^3$, —$SO_2NR^2R^3$, —$COOR^2$ or —$SO_3R^2$;

R are identical or different radicals:
hydrogen;
$C_1$-$C_{30}$-alkyl whose carbon chain may be interrupted by one or more —O—, —S—, —$NR^1$—, —N=$CR^1$—, —C≡C—, —$CR^1$=$CR^1$—, —CO—, —SO— and/or —$SO_2$— moieties and which may be mono- or polysubstituted by the (ii), (iii), (iv) and/or (v) radicals specified as substituents for the $R^1$ radicals;
$C_3$-$C_8$-cycloalkyl, to which may be fused further saturated or unsaturated 5- to 7-membered rings whose carbon skeleton may be interrupted by one or more —O—, —S—, —$NR^1$—, —N=$CR^1$—, —$CR^1$=$CR^1$—, —CO—, —SO— and/or —$SO_2$— moieties, where the entire ring system may be mono- or polysubstituted by the (i), (ii), (iii), (iv) and/or (v) radicals specified as substituents for the R' radicals;
aryl or hetaryl, to each of which may be fused further saturated or unsaturated 5- to 7-membered rings whose carbon skeleton may be interrupted by one or more —O—, —S—, —$NR^1$—, —N=$CR^1$—, —$CR^1$=$CR^1$—, —CO—, —SO— and/or —$SO_2$— moieties, where the entire ring system may be mono- or polysubstituted by the (i), (ii), (iii), (iv), (v) radicals specified as substituents for the R' radicals, and/or aryl- and/or hetarylazo, each of which may be mono- or polysubstituted by $C_1$-$C_{10}$-alkyl, $C_1$-$C_6$-alkoxy and/or cyano;

$R^1$ is hydrogen or $C_1$-$C_{18}$-alkyl, where the $R^1$ radicals may be the same or different when they occur more than once;

$R^2$, $R^3$ are each independently:
hydrogen;
$C_1$-$C_{18}$-alkyl whose carbon chain may be interrupted by one or more —O—, —S—, —CO—, —SO— and/or —$SO_2$— moieties and which may be mono- or polysubstituted by $C_1$-$C_{12}$-alkoxy, $C_1$-$C_6$-alkylthio, hydroxyl, mercapto, halogen, cyano, nitro, aryl and/or —$COOR^1$;
aryl or hetaryl, to each of which may be fused further saturated or unsaturated 5- to 7-membered rings whose carbon skeleton may be interrupted by one or more —O—, —S—, —CO— and/or —$SO_2$— moieties, where the entire ring system may be mono- or polysubstituted by $C_1$-$C_{12}$-alkyl and/or the above radicals specified as substituents for alkyl;
$C_3$-$C_8$-cycloalkyl to which may be fused further saturated or unsaturated 5- to 7-membered rings whose carbon skeleton may be interrupted by one or more —O—, —S—, —$NR^1$—, —N=$CR^1$—, —$CR^1$=$CR^1$—, —CO—, —SO— and/or —$SO_2$— moieties, where the entire ring system may be mono- or polysubstituted by $C_1$-$C_{12}$-alkyl and/or the above radicals specified as substituents for alkyl;
m, n are each independently 0 or 1.

2. A The dibenzorylenetetracarboximide according to claim 1, in which R, R', m, and n are each defined as follows:
R' are identical or different radicals:
hydrogen;
phenoxy or thiophenoxy, each of which may be mono- or polysubstituted by identical or different radicals (i), (ii), (iii), (iv) and/or (v):

(i) $C_1$-$C_{30}$-alkyl whose carbon chain may be interrupted by one or more —O—, —S—, —$NR^1$—, —$CR^1$=$CR^1$— and/or —CO— and/or —$SO_2$— moieties and which may be mono- or polysubstituted by: $C_1$-$C_{12}$-alkoxy, hydroxyl, halogen, cyano, and/or aryl which may be mono- or polysubstituted by $C_1$-$C_{18}$-alkyl or $C_1$-$C_6$-alkoxy;

(ii) $C_3$-$C_8$-cycloalkyl whose carbon skeleton may be interrupted by one or more —O—, —S—, —$NR^1$—, —$CR^1$=$CR^1$— and/or —CO— moieties and which may be mono- or polysubstituted by: $C_1$-$C_{18}$-alkyl, $C_1$-$C_{12}$-alkoxy and/or $C_1$-$C_6$-alkylthio;

(iii) aryl or hetaryl, to each of which may be fused further saturated or unsaturated 5- to 7-membered rings whose carbon skeleton may be interrupted by one or more —O—, —S—, —$NR^1$—, —$CR^1$=$CR^1$—, —CO—, —SO— and/or —$SO_2$— moieties, where the entire ring system may be mono- or polysubstituted by: $C_1$-$C_{18}$-alkyl, $C_1$-$C_{12}$-alkoxy, —C≡$CR^1$, —$CR^1$=$CR^1_2$, hydroxyl, halogen, cyano, —$NR^2R^3$, —$NR^2COR^3$, —$CONR^2R^3$, —$SO_2NR^2R^3$, —$COOR^2$, —$SO_3R^2$, aryl and/or hetaryl, each of which may be mono- or polysubstituted by $C_1$-$C_{18}$-alkyl, $C_1$-$C_{18}$-alkoxy and/or cyano;

(iv) a —U— aryl radical which may be mono- or polysubstituted by the above radicals specified as substituents for the aryl radicals (iii), where U is an —O—, —S—, —$NR^1$—, —CO—, —SO— or —$SO_2$— moiety;

(v) $C_1$-$C_{12}$-alkoxy, $C_1$-$C_6$-alkylthio, —C≡$CR^1$=$CR^1_2$, hydroxyl, mercapto, halogen, cyano, nitro, —$NR^2R^3$, —$NR^2COR^3$, —$CONR^2R^3$, —$SO_2NR^2R^3$, —$COOR^2$ or —$SO_3R^2$;

R are identical or different radicals:
$C_1$-$C_{30}$-alkyl whose carbon chain may be interrupted by one or more —O— and/or —CO— moieties and which may be mono- or polysubstituted by: $C_1$-$C_6$-alkoxy, cyano and/or aryl which may be substituted by $C_1$-$C_{18}$-alkyl or $C_1$-$C_6$-alkoxy; $C_5$-$C_8$-cycloalkyl which may be mono- or polysubstituted by $C_1$-$C_6$-alkyl; phenyl, naphthyl, pyridyl or pyrimidyl, each of which may be mono- or polysubstituted by: $C_1$-$C_{18}$-alkyl, $C_1$-$C_6$-alkoxy, halogen, cyano, nitro, —$CONR^2R^3$, —$SO_2NR^2R^3$ and/or phenyl- and/or naphthylazo, each of which may be mono- or polysubstituted by $C_1$-$C_{10}$-alkyl, $C_1$-$C_6$-alkoxy and/or cyano;

$R^1$ is hydrogen or $C_1$-$C_6$-alkyl;
$R^2$, $R^3$ are each independently:
hydrogen;
$C_1$-$C_{18}$-alkyl which may be mono- or polysubstituted by $C_1$-$C_6$-alkoxy, hydroxyl, halogen and/or cyano;

aryl or hetaryl, each of which may be mono- or polysubstituted by $C_1$-$C_6$-alkyl and/or the above radicals specified as substituents for alkyl;

m, n are each 0 or 1.

3. The dibenzorylenetetracarboximide according to claim 1, in which R, R', m, and n are each defined as follows:

R' are identical radicals:
  hydrogen;
  phenoxy which may be mono- or polysubstituted by identical or different radicals (i), (ii), (iii), (iv) and/or (v):
  (i) $C_1$-$C_{18}$-alkyl whose carbon chain may be interrupted by one or more —O—, —S—, —$NR^1$— and/or —CO— moieties and which may be mono- or polysubstituted by: $C_1$-$C_{12}$-alkoxy, hydroxyl and/or halogen;
  (ii) $C_3$-$C_8$-cycloalkyl which may be mono- or polysubstituted by $C_1$-$C_{18}$-alkyl and/or $C_1$-$C_{12}$-alkoxy;
  (iii) aryl or hetaryl which may be mono- or polysubstituted by $C_1$-$C_{18}$-alkyl, $C_1$-$C_{12}$-alkoxy, hydroxyl and/or halogen;
  (iv) a —U— aryl radical which may be mono- or polysubstituted by the above radicals specified as substituents for the aryl radicals (iii), where U is an —O—, —S— or —$NR^1$— moiety;
  (v) $C_1$-$C_{12}$-alkoxy, hydroxyl, halogen or cyano;

R are identical radicals:
  $C_1$-$C_{30}$-alkyl whose carbon chain may be interrupted by one or more —O— and/or —CO— moieties and which may be mono- or polysubstituted by: $C_1$-$C_6$-alkoxy, cyano and/or aryl which may be mono- or polysubstituted by $C_1$-$C_{18}$-alkyl or $C_1$-$C_6$-alkoxy;
  $C_5$-$C_8$-cycloalkyl which may be mono- or polysubstituted by $C_1$-$C_6$-alkyl;
  phenyl, naphthyl, pyridyl or pyrimidyl, each of which may be mono- or polysubstituted by: $C_1$-$C_{18}$-alkyl, $C_1$-$C_6$-alkoxy, halogen, cyano, nitro, —$CONR^2R^3$, —$SO_2NR^2R^3$ and/or phenyl- and/or naphthylazo, each of which may be mono- or polysubstituted by $C_1$-$C_{10}$-alkyl, $C_1$-$C_6$-alkoxy and/or cyano;

$R^1$ is hydrogen or $C_1$-$C_6$-alkyl;

$R^2$, $R^3$ are each independently:
  hydrogen;
  $C_1$-$C_{18}$-alkyl which may be mono- or polysubstituted by $C_1$-$C_6$-alkoxy, hydroxyl, halogen and/or cyano;
  aryl or hetaryl, each of which may be mono- or polysubstituted by $C_1$-$C_6$-alkyl and/or the above radicals specified as substituents for alkyl;

n, m are each 1.

4. The dibenzorylenetetracarboximide according to claim 1, where the R radicals are each independently selected from groups of the formulae II.1 to II.5:

(II.1)

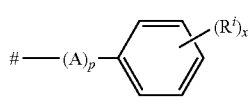
(II.2)

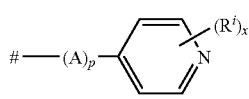
(II.3)

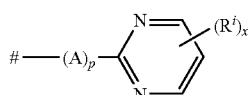
(II.4)

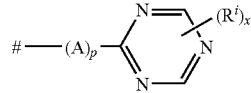
(II.5)

in which is the site of attachment to the imide nitrogen atom, p is 0 or 1, x is 2 or 3 in the compounds of the formula II.1, is 1, 2 or 3 in the compounds of the formulae II.2, II.3 and II.4, and is 1 or 2 in the compounds of the formula II.5, A, where present, is a $C_1$-$C_{10}$-alkylene group which may be interrupted by one or more nonadjacent groups selected from —O— and —S—, where, in the case that x is 2 in the compounds of the formula II.1, the carbon atom which comprises the $R^i$ radicals additionally comprises a hydrogen atom, the $R^i$ radicals are each independently selected from $C_1$-$C_{30}$-alkyl which may be interrupted by one or more nonadjacent oxygen atom(s), where at least one of the $R^i$ radicals in the compounds represented by formula II.1 may also be $C_1$-$C_{30}$-alkyloxy or $C_1$-$C_{30}$-alkylthio.

5. The dibenzorylenetetracarboximide according to claim 4, where x is 2 or 3.

6. The dibenzorylenetetracarboximide according to claim 4, where the $R^i$ radicals are each independently a selected from $C_3$-$C_{30}$-alkyl which may be interrupted by one or more nonadjacent oxygen atom(s), where at least one of the $R^i$ radicals in the compounds of the formula II.1 may also be $C_3$-$C_{30}$-alkyloxy or $C_3$-$C_{30}$-alkylthio.

7. The dibenzorylenetetracarboximide according to claim 1, where the R' radicals are both hydrogen.

8. The dibenzorylenetetracarboximide according to claim 1, where the R' radicals are selected from radicals of the formula:

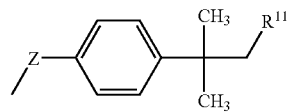

in which

Z is O or S, and $R^{11}$ is selected from the group consisting of hydrogen, $C_1$-$C_8$-alkyl whose carbon chain may be interrupted by one or more —O—, —S—, —$NR^1$—, —C(=O)— and/or —$SO_2$— moieties and which may be mono- or polysubstituted by $C_1$-$C_6$-alkoxy and/or a 5- to 7-membered heterocyclic radical which is bonded via a nitrogen atom and may comprise further heteroatoms and be aromatic, and $C_5$-$C_8$-cycloalkyl whose carbon skeleton may be interrupted by one or more —O—, —S—, —$NR^1$—, —C(=O)— and/or —$SO_2$— moieties and which may be mono- or polysubstituted by $C_1$-$C_6$-alkyl, where $R^1$ is hydrogen or $C_1$-$C_6$-alkyl.

9. A process for preparing dibenzorylenetetracarboximides of formula Ia

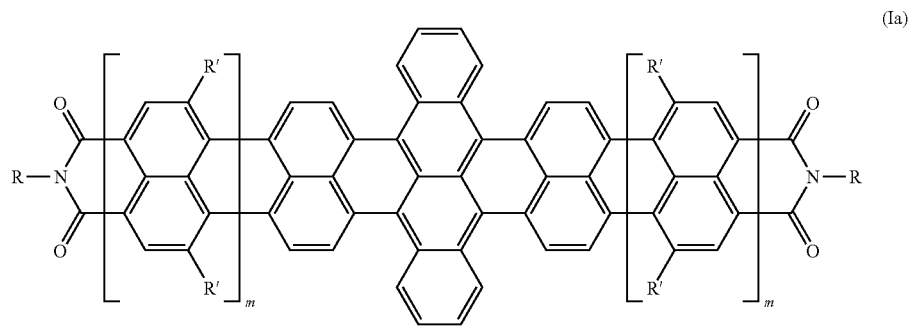

in which R, R' and m are each as defined in claim 1, which comprises
a) subjecting a peri-(dioxaborolan-2-yl)rylenedicarboximide of formula IIa

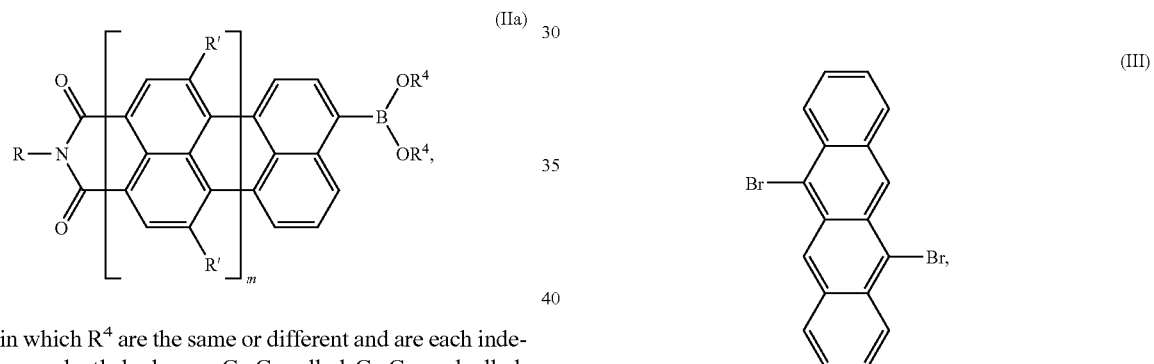

in which $R^4$ are the same or different and are each independently hydrogen, $C_1$-$C_{30}$-alkyl, $C_5$-$C_8$-cycloalkyl, aryl or heteroaryl, and where two $OR^4$ radicals bonded to the same boron atom together may also be —$OCH_2CH_2O$—, in which 1, 2, 3 or 4 hydrogen atoms may also be replaced by $C_1$-$C_{30}$-alkyl, $C_5$-$C_8$-cycloalkyl, aryl or heteroaryl groups, in the presence of an organic solvent and of a transition metal catalyst and of a base, to a Suzuki coupling reaction with 5,11-dibromotetracene of formula III

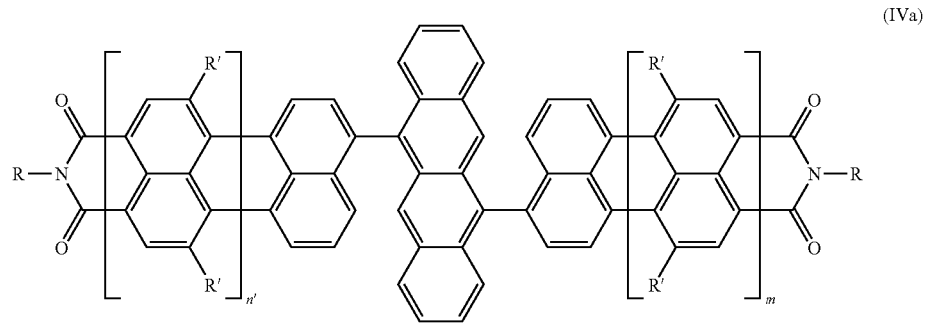

b) subjecting the tetracene-5,11-bis(rylenedicarboximide) of formula IVa formed in step a)

to a first cyclodehydrogenation in the presence of an inert organic solvent and of a Lewis acid and c) cyclodehydrogenating the bisrylene derivative of formula Va formed in step b)

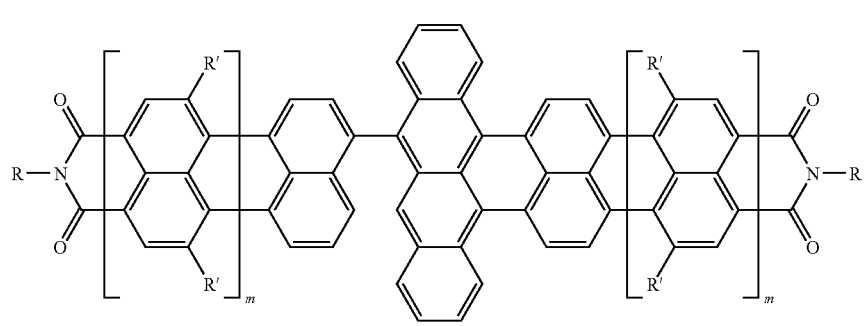

in an organic reaction medium which has hydroxyl and amino functions and comprises an undissolved base further to give the dibenzorylenetetracarboximide Ia.

10. A process for preparing dibenzorylenetetracarboximides of the general formula Ib

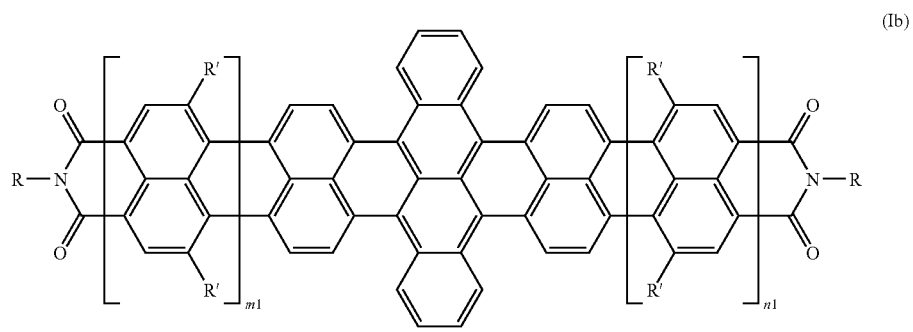

in which R and R' are each as defined in claim 1, m1 and n1 are different from one another and are each 0 or 1, which comprises a1) subjecting a peri-(dioxaborolan-2-yl)rylenedicarboximide of formula IIb1

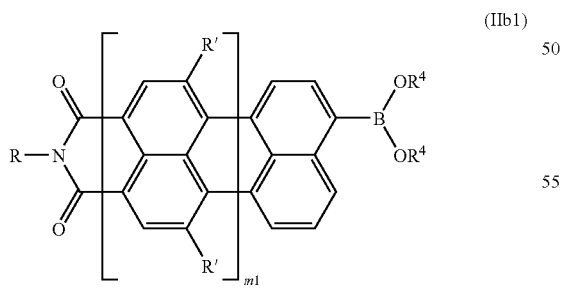

in which $R^4$ are the same or different and are each independently hydrogen, $C_1$-$C_{30}$-alkyl, $C_5$-$C_8$-cycloalkyl, aryl or heteroaryl, and where two $OR^4$ radicals bonded to the same boron atom together may also be —$OCH_2CH_2O$—, in which 1, 2, 3 or 4 hydrogen atoms may also be replaced by $C_1$-$C_{30}$-alkyl, $C_5$-$C_8$-cycloalkyl, aryl or heteroaryl groups, to a first Suzuki coupling reaction with 5,11-dibromotetracene and a2) subjecting the 5-bromotetracene-11-rylenedicarboximide of formula III' formed in step a1)

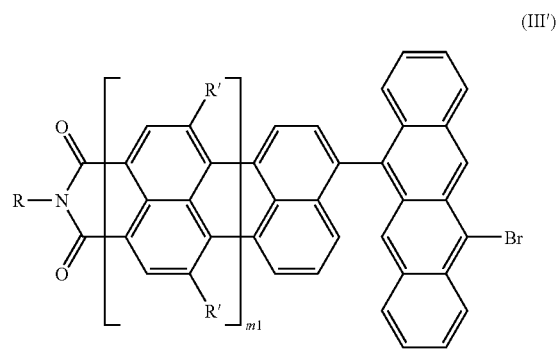

to a second Suzuki coupling reaction with a peri-(dioxaborolan-2-yl)rylenedicarboximide of formula IIb2

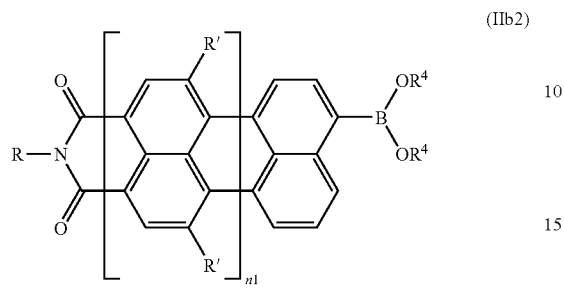
(IIb2)

in the presence of an organic solvent and of a transition metal catalyst and of a base, b) subjecting the tetracene-5,11-bis(rylenedicarboximide) of formula IVb formed in step a2)

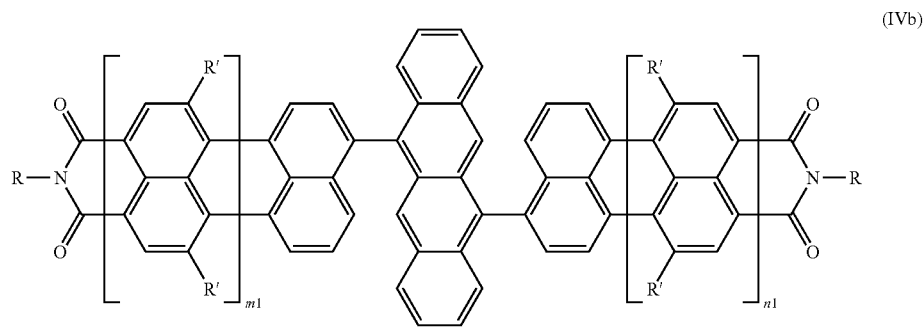
(IVb)

to a first cyclodehydrogenation in the presence of an inert organic solvent and of a Lewis acid and c) cyclodehydrogenating the bisrylene derivative of formula Vb formed in step b)

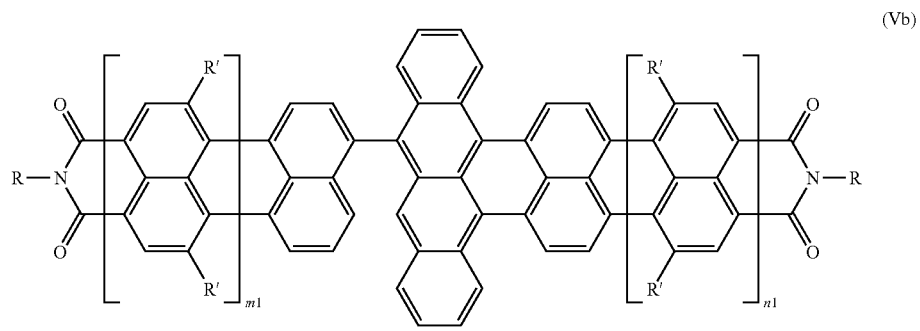
(Vb)

in an organic reaction medium which has hydroxyl and amino functions and comprises an undissolved base further to give the dibenzorylenetetracarboximide Ib.

11. A tetracene-5,11-bis(rylenedicarboximide) of formula IV

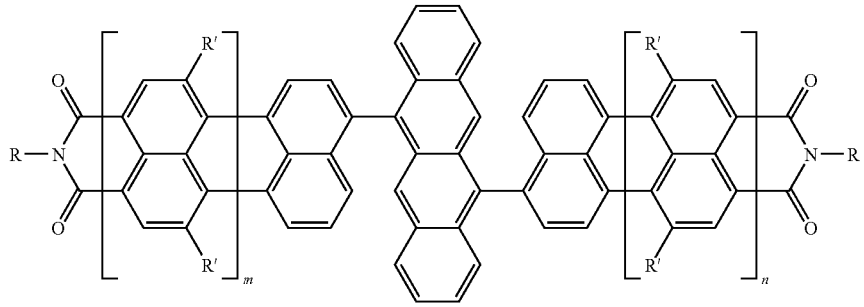

(IV)

in which R, R', m, and n are each defined as follows:
R' are identical or different radicals:
  hydrogen;
  aryloxy, arylthio, hetaryloxy or hetarylthio, to each of which may be fused further saturated or unsaturated 5- to 7-membered rings whose carbon skeleton may be interrupted by one or more —O—, —S—, —NR$^1$—, —N=CR$^1$—, —CO—, —SO— and/or —SO$_2$— moieties, where the entire ring system may be mono- or polysubstituted by the radicals (i), (ii), (iii), (iv) and/or (v):
  (i) $C_1$-$C_{30}$-alkyl whose carbon chain may be interrupted by one or more —O—, —S—, —NR$^1$—, —N=CR$^1$—, —C≡C—, —CR$^1$=CR$^1$—, —CO—, —SO— and/or —SO$_2$— moieties and which may be mono- or polysubstituted by: $C_1$-$C_{12}$-alkoxy, $C_1$-$C_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, aryl and/or saturated or unsaturated $C_4$-$C_7$-cycloalkyl whose carbon skeleton may be interrupted by one or more —O—, —S—, —NR$^1$—, —N=CR$^1$—, —CR$^1$=CR$^1$—, —CO—, —SO— and/or—SO$_2$— moieties, where the aryl and cycloalkyl radicals may each be mono- or polysubstituted by $C_1$-$C_{18}$-alkyl and/or the above radicals specified as substituents for alkyl;
  (ii) $C_3$-$C_8$-cycloalkyl whose carbon skeleton may be interrupted by one or more —O—, —S—, —NR$^1$—, —N=CR$^1$—, —CR$^1$=CR$^1$—, —CO—, —SO— and/or —SO$_2$— moieties and to which may be fused further saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$,—CONR$^2$R$^3$, —SO$_2$NR$^2$R$^3$, —COOR$^2$ and/or—SO$_3$R$^2$;
  (iii) aryl or hetaryl, to which may be fused further saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, aryl and/or hetaryl, each of which may be mono- or polysubstituted by $C_1$-$C_{18}$-alkyl, $C_1$-$C_{12}$-alkoxy, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$ and/or —SO$_3$R$^2$;
  (iv) a —U— aryl radical which may be mono- or polysubstituted by the above radicals specified as substituents for the aryl radicals (iii), where U is an —O—, —S—, —NR$^1$—, —CO—, —SO— or —SO$_2$— moiety;
  (v) $C_1$-$C_{12}$-alkoxy, $C_1$-$C_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$ or —SO$_3$R$^2$,
R are identical or different radicals:
  hydrogen;
  $C_1$-$C_{30}$-alkyl whose carbon chain may be interrupted by one or more —O—, —S—, —NR$^1$—, —N=CR$^1$—, —C≡C—, —CR$^1$=CR$^1$—, —CO—, —SO— and/or —SO$_2$— moieties and which may be mono- or polysubstituted by the (ii), (iii), (iv) and/or (v) radicals specified as substituents for the R' radicals;
  $C_3$-$C_8$-cycloalkyl, to which may be fused further saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties, where the entire ring system may be mono- or polysubstituted by the (i), (ii), (iii), (iv) and/or (v) radicals specified as substituents for the R' radicals;
  aryl or hetaryl, to which may be fused further saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties, where the entire ring system may be mono- or polysubstituted by the (i), (ii), (iii), (iv), (v) radicals specified as substituents for the R' radicals; and/or aryl- and/or hetarylazo, each of which may be mono- or polysubstituted by $C_1$-$C_{10}$-alkyl, $C_1$-$C_6$-alkoxy and/or cyano;
R' is hydrogen or $C_1$-$C_{18}$-alkyl, where the R' radicals may be the same or different when they occur more than once;
$R^2$, $R^3$ are each independently:
  hydrogen;
  $C_1$-$C_{18}$-alkyl whose carbon chain may be interrupted by one or more —O—, —S—, —CO—, —SO— and/or —SO$_2$— moieties and which may be mono- or polysubstituted by $C_1$-$C_{12}$-alkoxy, $C_1$-$C_6$-alkylthio, hydroxyl, mercapto, halogen, cyano, nitro, aryl and/or —COOR$^1$;

aryl or hetaryl, to each of which may be fused further saturated or unsaturated 5- to 7-membered rings whose carbon skeleton may be interrupted by one or more —O—, —S—, —CO— and/or —SO$_2$— moieties, where the entire ring system may be mono- or polysubstituted by C$_1$-C$_{12}$-alkyl and/or the above radicals specified as substituents for alkyl;

C$_3$-C$_8$-cycloalkyl to which may be fused further saturated or unsaturated 5- to 7-membered rings whose carbon skeleton may be interrupted by one or more —O—, —S—, —NR$^1$—, —NR$^{1a}$—, —N=CR$^1$—, —CR$^1$=CR$^1$—, —CO—, —SO— and/or —SO$_2$— moieties, where the entire ring system may be mono- or polysubstituted by C$_1$-C$_{12}$-alkyl and/or the above radicals specified as substituents for alkyl;

m, n are each independently 0 or 1.

12. A bisrylene derivative of formula V

—CR$^1$=CR$^1$—, —CO—, —SO— and/or —SO$_2$— moieties, where the entire ring system may be mono- or polysubstituted by: C$_1$-C$_{18}$-alkyl, C$_1$-C$_{12}$-alkoxy, C$_1$-C$_6$-alkylthio, —C≡CR$^1$, —CR$^1$=CR$^1$$_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$ and/or —SO$_3$R$^2$;

(iii) aryl or hetaryl, to which may be fused further saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties, where the entire ring system may be mono- or polysubstituted by: C$_1$-C$_{18}$-alkyl, C$_1$-C$_{12}$-alkoxy, C$_1$-C$_6$-alkylthio, —C≡CR$^1$, —CR$^1$=CR$^1$$_2$, hydroxyl, mercapto, halogen, cyano, nitro, —NR$^2$R$^3$, —NR$^2$COR$^3$, —CONR$^2$R$^3$, —SO$_2$NR$^2$R$^3$, (V)

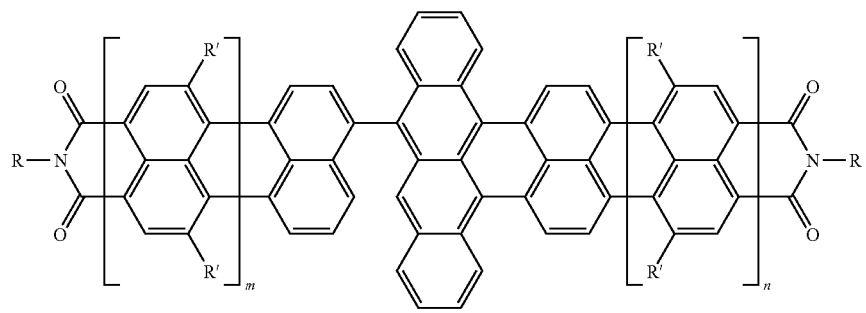

in which R, R', m, and n are each defined as follows:

R' are identical or different radicals:
hydrogen;
aryloxy, arylthio, hetaryloxy or hetarylthio, to each of which may be fused further saturated or unsaturated 5- to 7-membered rings whose carbon skeleton may be interrupted by one or more —O—, —S—, —NR$^1$—, —N=CR$^1$—, —CO—, —SO— and/or —SO$_2$— moieties, where the entire ring system may be mono- or polysubstituted by the radicals (i), (ii), (iii), (iv) and/or (v):

(i) C$_1$-C$_{30}$-alkyl whose carbon chain may be interrupted by one or more —O—, —S—, —NR$^1$—, —N=CR$^1$—, —CR$^1$=CR$^1$—, —CO—, —SO— and/or —SO$_2$— moieties and which may be mono- or polysubstituted by: C$_1$-C$_{12}$-alkoxy, C$_1$-C$_6$-alkylthio, —C≡CR$^1$, —CR$^1$=CR$^1$$_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, aryl and/or saturated or unsaturated C$_4$-C$_7$-cycloalkyl whose carbon skeleton may be interrupted by one or more —O—, —S—, —NR$^1$—, —N=CR$^1$—, —CR$^1$=CR$^1$—, —CO—, —SO— and/or —SO$_2$— moieties, where the aryl and cycloalkyl radicals may each be mono- or polysubstituted by C$_1$-C$_6$-alkyl and/or the above radicals specified as substituents for alkyl;

(ii) C$_3$-C$_8$-cycloalkyl whose carbon skeleton may be interrupted by one or more —O—, —S—, —NR$^1$—, —N=CR$^1$—, —CR$^1$=CR$^1$—, —CO—, —SO— and/or —SO$_2$— moieties and to which may be fused further saturated or unsaturated 5- to 7-membered rings whose carbon skeleton may be interrupted by one or more —O—, —S—, —NR$^1$—, —N=CR$^1$—, —COOR$^2$, —SO$_3$R$^2$, aryl and/or hetaryl, each of which may be mono- or polysubstituted by C$_1$-C$_{18}$-alkyl, C$_1$-C$_{12}$-alkoxy, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$ and/or —SO$_3$R$^2$;

(iv) a —U— aryl radical which may be mono- or polysubstituted by the above radicals specified as substituents for the aryl radicals (iii), where U is an —O—, —S—, —NR$^1$—, —CO—, —SO— or —SO$_2$— moiety;

(v) C$_1$-C$_{12}$-alkoxy, C$_1$-C$_6$-alkylthio, —C≡CR$^1$, —CR$^1$=CR$^1$$_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$ or —SO$_3$R$^2$, R are identical or different radicals:
hydrogen;
C$_1$-C$_{30}$-alkyl whose carbon chain may be interrupted by one or more —O—, —S—, —NR$^1$—, —N=CR$^1$—, —C≡C—, —CR$^1$=CR$^1$—, —CO—, —SO— and/or —SO$_2$— moieties and which may be mono- or polysubstituted by the (ii), (iii), (iv) and/or (v) radicals specified as substituents for the R' radicals;

C$_3$-C$_8$-cycloalkyl, to which may be fused further saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties, where the entire ring system may be mono- or polysubstituted by the (i), (ii), (iii), (iv) and/or (v) radicals specified as substituents for the R' radicals;

aryl or hetaryl, to each of which may be fused further saturated or unsaturated 5- to 7-membered rings whose carbon skeleton may be interrupted by one or more —O—, —S—, —NR$^1$—, —N=CR$^1$—, —$CR^1$=$CR^1$—, —CO—, —SO— and/or —$SO_2$— moieties, where the entire ring system may be mono- or polysubstituted by the (i), (ii), (iii), (iv), (v) radicals specified as substituents for the R' radicals; and/or aryl- and/or hetarylazo, each of which may be mono- or polysubstituted by $C_1$-$C_{10}$-alkyl, $C_1$-$C_6$-alkoxy and/or cyano;

$R^1$ is hydrogen or $C_1$-$C_{18}$-alkyl, where the $R^1$ radicals may be the same or different when they occur more than once;

$R^2$, $R^3$ are each independently:
hydrogen;
$C_1$-$C_{18}$-alkyl whose carbon chain may be interrupted by one or more —O—, —S—, —CO—, —SO— and/or —$SO_2$— moieties and which may be mono- or polysubstituted by $C_1$-$C_{12}$-alkoxy, $C_1$-$C_6$-alkylthio, hydroxyl, mercapto, halogen, cyano, nitro, aryl and/or —$COOR^1$;
aryl or hetaryl, to each of which may be fused further saturated or unsaturated 5- to 7-membered rings whose carbon skeleton may be interrupted by one or more —O—, —S—, —CO— and/or —$SO_2$— moieties, where the entire ring system may be mono- or polysubstituted by $C_1$-$C_{12}$-alkyl and/or the above radicals specified as substituents for alkyl;
$C_3$-$C_8$-cycloalkyl to which may be fused further saturated or unsaturated 5- to 7-membered rings whose carbon skeleton may be interrupted by one or more —O—, —S—, —$NR^1$—, —$NR^{1a}$—, —N=$CR^1$—, —$CR^1$=$CR^1$—, —CO—, —SO— and/or —$SO_2$— moieties, where the entire ring system may be mono- or polysubstituted by $C_1$-$C_{12}$-alkyl and/or the above radicals specified as substituents for alkyl;

m, n are each independently 0 or 1.

13. An organic field-effect transistor comprising
a substrate comprising
at least one gate structure,
a source electrode,
a drain electrode, and
at least one compound represented by formula I as defined in claim 1 as an n-semiconductor.

14. A substrate comprising
at least one organic field-effect transistor,
wherein said at least one field-effect transistor comprises at least one compound of formula I as defined in claim 1 as an n-semiconductor.

15. A semiconductor unit comprising at least one substrate as defined in claim 14.

16. The dibenzorylenetetracarboximide according to claim 5, where the $R^i$ radicals are each independently a selected from $C_3$-$C_{30}$-alkyl which may be interrupted by one or more nonadjacent oxygen atom(s), where at least one of the $R^i$ radicals in the compounds of the formula II.1 may also be $C_3$-$C_{30}$-alkyloxy or $C_3$-$C_{30}$-alkylthio.

17. The dibenzorylenetetracarboximide according to claim 4, where each $R^i$ radical is independently a $C_3$-$C_{30}$-alkyl which may be interrupted by one or more nonadjacent oxygen atom(s) and at least one $R^i$ radical in the compounds represented by formula II.1 can be a $C_3$-$C_{30}$-alkyloxy or a $C_3$-$C_{30}$-alkylthio.

18. The process according to claim 9, wherein a) occurs in the presence of organic solvent and water.

19. The process according to claim 10, wherein a2) occurs in the presence of organic solvent and water.

* * * * *